United States Patent
Barrett et al.

(10) Patent No.: US 11,242,394 B2
(45) Date of Patent: *Feb. 8, 2022

(54) ANTI-CD40 ANTIBODIES

(71) Applicant: Boehringer Ingelheim International GmbH, Ingelheim am Rhein (DE)

(72) Inventors: Rachel Rebecca Barrett, Bethel, CT (US); Scott Ronald Brodeur, New Hope, PA (US); Keith Canada, Woodbury, CT (US); Tobias Litzenburger, Mittelbiberach (DE); Sanjaya Singh, Sandy Hook, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 180 days.

This patent is subject to a terminal disclaimer.

(21) Appl. No.: 16/031,209

(22) Filed: Jul. 10, 2018

(65) Prior Publication Data

US 2019/0169301 A1 Jun. 6, 2019

Related U.S. Application Data

(60) Continuation of application No. 15/341,085, filed on Nov. 2, 2016, now abandoned, which is a continuation of application No. 15/098,388, filed on Apr. 14, 2016, now abandoned, which is a continuation of application No. 14/742,764, filed on Jun. 18, 2015, now abandoned, which is a continuation of application No. 14/046,121, filed on Oct. 4, 2013, now Pat. No. 9,090,696, which is a division of application No. 13/075,303, filed on Mar. 30, 2011, now Pat. No. 8,591,900.

(60) Provisional application No. 61/319,574, filed on Mar. 31, 2010.

(51) Int. Cl.
| A61K 39/395 | (2006.01) |
| C07K 16/28  | (2006.01) |
| A61K 9/00   | (2006.01) |
| C07K 1/22   | (2006.01) |
| A61K 39/00  | (2006.01) |

(52) U.S. Cl.
CPC ........ *C07K 16/2878* (2013.01); *A61K 9/0019* (2013.01); *C07K 1/22* (2013.01); *A61K 2039/505* (2013.01); *C07K 2317/24* (2013.01); *C07K 2317/33* (2013.01); *C07K 2317/51* (2013.01); *C07K 2317/515* (2013.01); *C07K 2317/53* (2013.01); *C07K 2317/565* (2013.01); *C07K 2317/71* (2013.01); *C07K 2317/73* (2013.01); *C07K 2317/732* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 8,293,237 B2   | 10/2012 | Burkly et al. |
| 8,591,900 B2   | 11/2013 | Barrett et al. |
| 9,090,696 B2   | 7/2015  | Barrett et al. |
| 2003/0059427 A1 | 3/2003 | Force et al. |
| 2003/0165499 A1 | 9/2003 | Chu et al. |
| 2004/0110226 A1 | 6/2004 | Lazar et al. |
| 2004/0120948 A1 | 6/2004 | Yama et al. |
| 2007/0148163 A1 | 6/2007 | Takahashi et al. |
| 2009/0304706 A1* | 12/2009 | Lu .............. A61P 1/16 424/144.1 |
| 2011/0243932 A1 | 10/2011 | Barrett et al. |
| 2013/0011405 A1 | 1/2013  | Long et al. |
| 2014/0004131 A1 | 1/2014  | Mueller et al. |

FOREIGN PATENT DOCUMENTS

| JP | 2010-521967 A    | 7/2010 |
| WO | WO-99/42075 A2   | 8/1999 |
| WO | WO-03/040170 A2  | 5/2003 |
| WO | WO-2006/073443 A2 | 4/2005 |
| WO | WO-2006/128103 A2 | 11/2006 |
| WO | WO-2007/124299 A2 | 11/2007 |
| WO | WO-2007/129895 A2 | 11/2007 |
| WO | WO-2011/123489 A2 | 10/2011 |
| WO | WO-2012/149356 A2 | 11/2012 |

OTHER PUBLICATIONS

D'Angelo et al., Many Routes to an Antibody Heavy-Chain CDR3: Necessary, Yet Insufficient, for Specific Binding; Frontiers in Immunology vol. 9, Article 395 Mar. 2018; doi:10.3389/fimmu.2018.00395. (Year: 2018).*
Piche-Nicholas et al., Changes in complementarity-determining regions significantly alter IgG binding to the neonatal Fc receptor (FcRN) and pharmacokinetics; MABS 2018, vol. 10, No. 1, 81-94, doi.org/10.1080/19420862.2017.1389355. (Year: 2018).*
Lupus Nephritis Case at Mayo Clinic, downloaded Oct. 24, 2017, pp. 1-4, mayoclinic.org/diseases_conditions/lupus-pehritix/care-at-mayo-clini/mac-20354388?p=1, 2017.
Almagro et al., "Humanization of antibodies," Frontiers in Bioscience (Landmark Edition), Frontiers in Bioscience, US, Jan. 1, 2008, 13:1619-1633.
Amit et al., "Three-Dimensional Structure of an Antigen-Antibody Complex at 2.8 Å Resolution," Science, 1986, 233:747-753.
Aoyagi et al., "A Human Anti-CD40 Monoclonal Antibody, 4D11, for Kidney Transplantation in Cynomolgus Monkeys: Induction and Maintenance Therapy," American Journal of Transplantation, 2009, 9:1732-1741.

(Continued)

*Primary Examiner* — Phillip Gambel
(74) *Attorney, Agent, or Firm* — Foley & Lardner LLP

(57) ABSTRACT

The present invention relates to new humanized antagonistic anti-CD40 antibodies and therapeutic and diagnostic methods and compositions for using the same.

43 Claims, 14 Drawing Sheets

Specification includes a Sequence Listing.

(56) References Cited

OTHER PUBLICATIONS

Batra et al., "Pharmacokinetics and biodistribution of genetically engineered antibodies," Pharmaceutical Biotechnology, 2002, 13(6):603-608.
Brown et al., "Tolerance to Single, but Not Mulitple, Amino Acid Replacements in Antibody Vh CDR2," The Journal of Immunology, 1996, vol. 156, No. 9, pp. 3285-3291.
Chen et al., "Enhancement and Destruction of Antibody Function by Somatic Mutation: Unequal Occurrence is Controlled by V Gene Combinatorial Associations," The EMBO Journal, 1995, 14(12):2784-2794.
Colman, P. M., "Effects of Amino Acid Sequence Changes on Antibody-Antigen Interactions," Research in Immunology, 1994, 145:33-36.
Davies et al., "Affinity improvement of single antibody VH domains: residues in all three hypervariable regions affect antigen binding," Immunotechnology, 1996, 2(3):169-179.
Giusti et al., "Somatic diversification of S107 from an antiphosphocholine to an anti-DNA autoantibody is due to a single base change in its heavy chain variable region," Proceedings of the National Academy of Sciences, 1987, vol. 84, pp. 2926-2930.
Holt et al., "Domain antibodies: proteins for therapy," Trends in Biotechnology, 2003, 21(11):484-490.
International Search Report and Written Opinion for PCT/US2011/030427 dated Sep. 29, 2011.
International Search Report and Written Opinion for PCT/US2016/049558 dated Nov. 17, 2016.
Jeffry et al., "Safety Evaluation of a Fully Human Antagonist Anti-CD40 Antibody, CHIR-12.12, in a Dose Range-Finding Study in Cynomolgus Monkeys," Blood (ASH Annual Meeting Abstracts), 2004, 104, Abstract No. 3282, 2 pages.
Kelley et al., "Preclinical pharmacokinetics, pharmacodynamics, and activity of a humanized anti-CD40 antibody (SGN-40) in rodents and non-human primates," British Journal of Pharmacology, 2006, 148(8):1116-1123.
Kontermann, Roland E., "Strategies to Extend Plasma Half-Lives of Recombinant Antibodies," BioDrugs, 2009, 23(2):93-109.
Kussie et al., "A Single Engineered Amino Acid Substitution Changes Antibody Fine Specificity," Journal of Immunology, 1994, 146-152.
Maynard et al., "Antibody Engineering," Annual Review of Biomedical Engineering, 2:339-376.
Miura et al., "Pharmacological and Toxicological Studies of a Fully Human Antibody (4D11) Against Human CD40 in Human Samples In Vitro and Non-Human Primates In Vivo," Preclinical Immunosuppression: Primate Studies, Abstract No. 1036, 420.
Mohan et al., "Interaction Between CD40 and its Ligand gp39 in the Development of Murine Lupus Nephritis," The Journal of Immunology, The American Association of Immunologists, 1995, 154(3): 1470-1480.
Pini et al., "Design and Use of a Phage Display Library: Human Anitbodies with Subnanomolar Affinity Against a Marker of Angiogenesis Eluted From a Two-Dimensional Gel," The Journal of Biological Chemistry, 1998, 273(34):21769-21776.
Ripoll et al., "CD40 Gene Silencing Reduces the Progression of Experimental Lupus Nephritis Modulating Local Milieu and Systemic Mechanisms," PLOS One, 2013 8(6):e65068, 13 pages.
Roopenian et al., "FcRn: the neonatal Fc receptor comes of age," Nature Reviews: Immunology, 2007, 7:715-725.
Rudikoff et al., "Single Amino Acid Substitution Altering Antigen-Binding Specificity," Proc Natl Acad Sci USA, 1982,79:1979-1983.
Schildbach et al., "Contribution of a single heavy chain residue to specificity of an anti-digoxin monoclonal antibody," Protein Science, 1994, 3:737-749.
Schildbach et al., "Heavy Chain Position 50 Is a Determinant of Affinity and Specificity for the Anti-digoxin Antibody 26-10," The Journal of Biological Chemistry, 1993, 269(29):21739-21747.
US Office Action in U.S. Appl. No. 15/252,308 dated Oct. 27, 2017.
Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.
Xiang et al., "Study of B72.3 combining sites by molecular modeling and site-directed mutagenesis," Protein Engineering, 2000, 13(5):339-344.
Zhihong et al., "Fine mapping of the antigen-antibody interaction of scFv215, a recombinant antibody inhibiting RNA polymerase II from *Drosophila melanogaster*," Journal of Molecular Recognition, 1999, 12:103-111.

\* cited by examiner

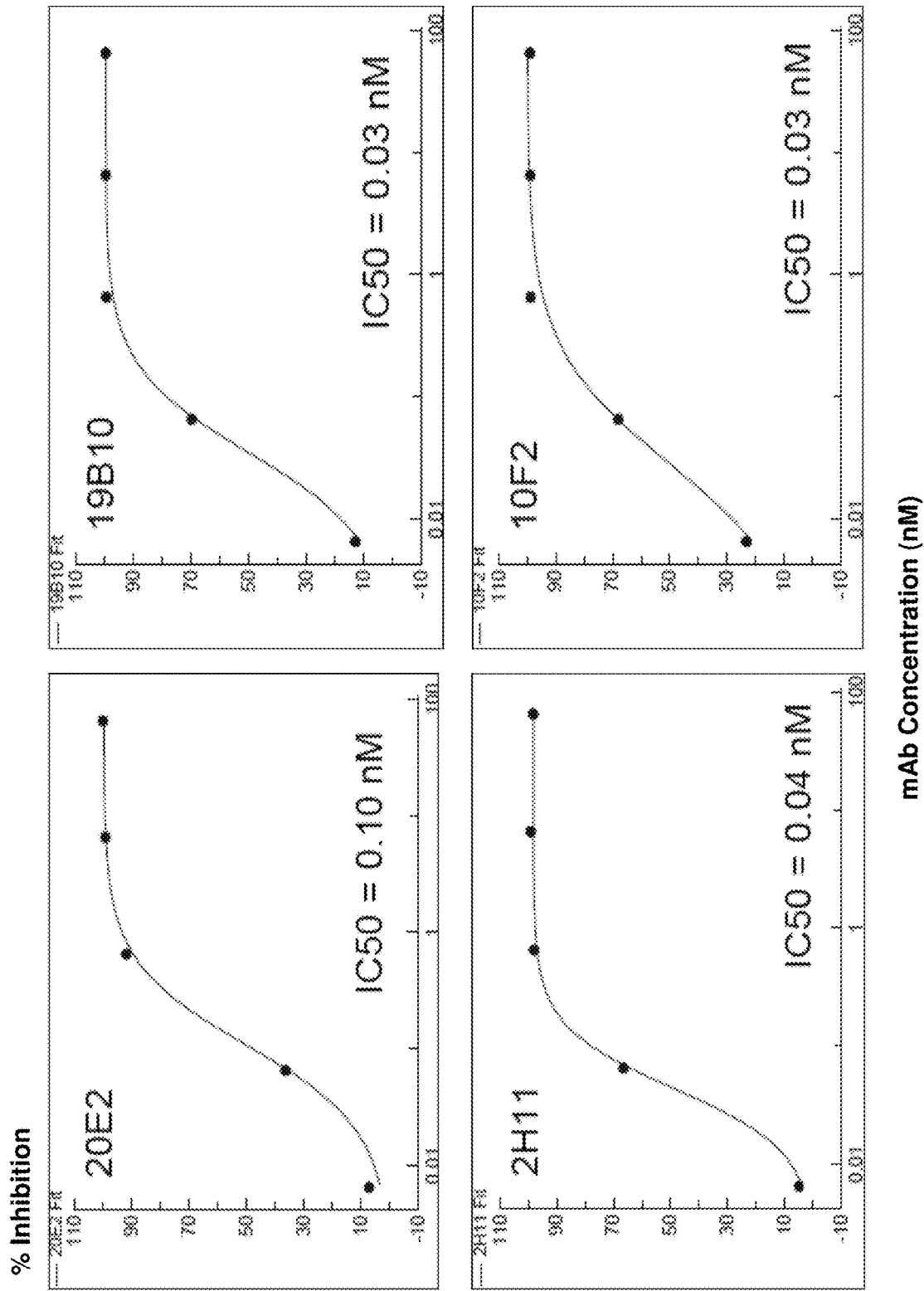

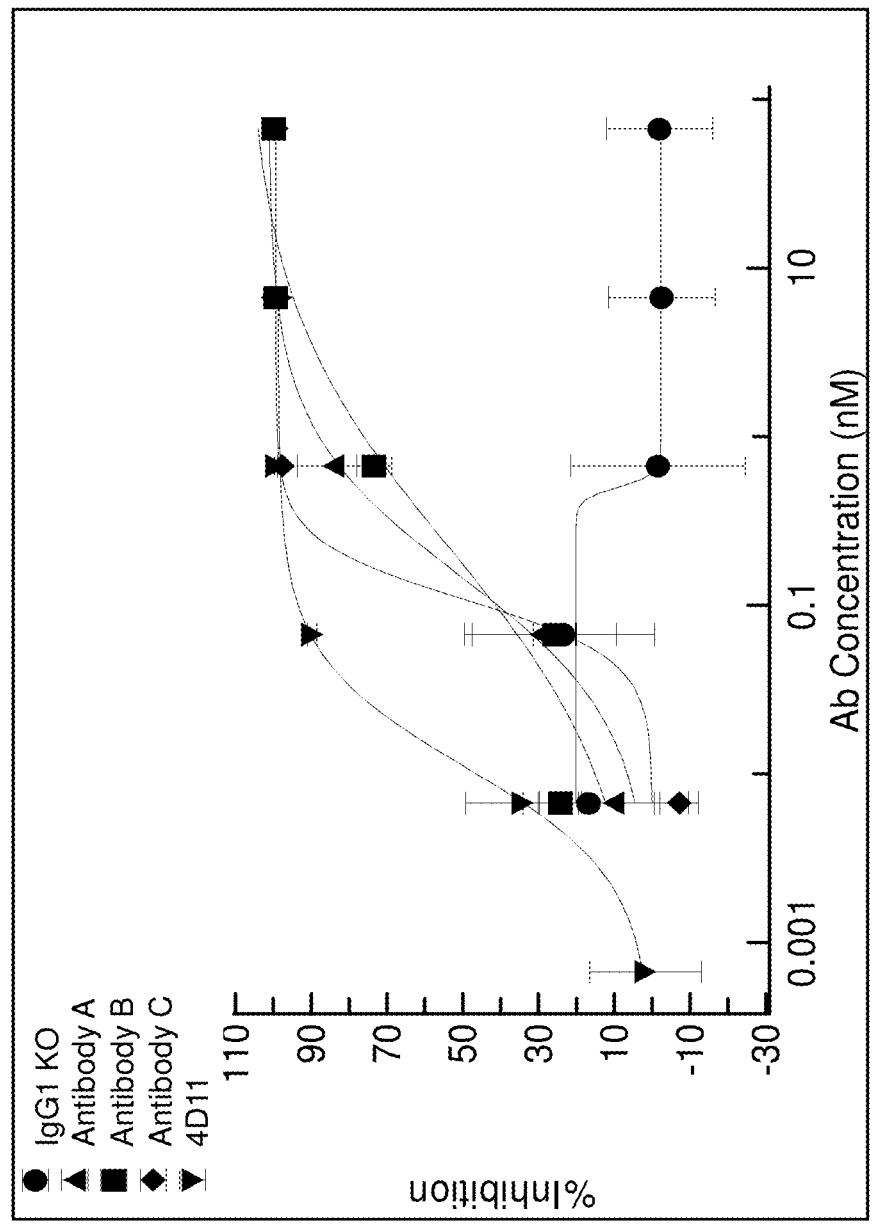

FIGURE 4

| Antibody Name | Isotype | Human B cell Proliferation Assay | |
|---|---|---|---|
| | | Antagonism | Agonism |
| | | Avg. IC50 nM ±SEM (n) | SI ±SEM (n) |
| Antibody B | hIgG1KO | 0.2±0.09 (n=3) | 1±0.3 (n=3) |
| Antibody A | hIgG1KO | 0.3±0.03 (n=3) | 1±0.13 (n=3) |
| Antibody C | hIgG1KO | 0.1±0.01 (n=3) | 1±0.06 (n=3) |
| 10F2 | hIgG1KO | 0.8±0.11 (n=3) | 1±0.09 (n=3) |
| 4D11 | hIgG4DM | 0.02±0.01 (n=3) | 1±0.11 (n=3) |
| G28.5 | mIgG1 | NT | 7±1.94 (n=3) |
| mu5D12 | hIgG4Pro | No Inhibition up to 67nM | 18±3.1 (n=3) |

NT=Not tested

A.

| mAb (isotype) | IC50 (nM +/- SEM) | | Fold Change |
|---|---|---|---|
| | Purified B cells | HWB | |
| Antibody B | 0.6 +/- 0.3 (n=4) | 1.3 +/- 0.7(n=4) | 2.2 |
| 4D11 (hIgG4 DM) | 0.03 +/- 0.01 (n=5) | 0.6 +/- 0.3 (n=4) | 20.0 |

B.

| mAb (isotype) | IC90 (nM +/- SEM) | | Fold Change |
|---|---|---|---|
| | Purified B cells | HWB | |
| Antibody B | 5.3 +/- 2.4 (n=4) | 4.3 +/- 2.1 (n=4) | 0.8 |
| 4D11 (hIgG4 DM) | 0.05 +/- 0.02 (n=5) | 1.3 +/- 0.64 (n=4) | 26 |

FIGURE 8
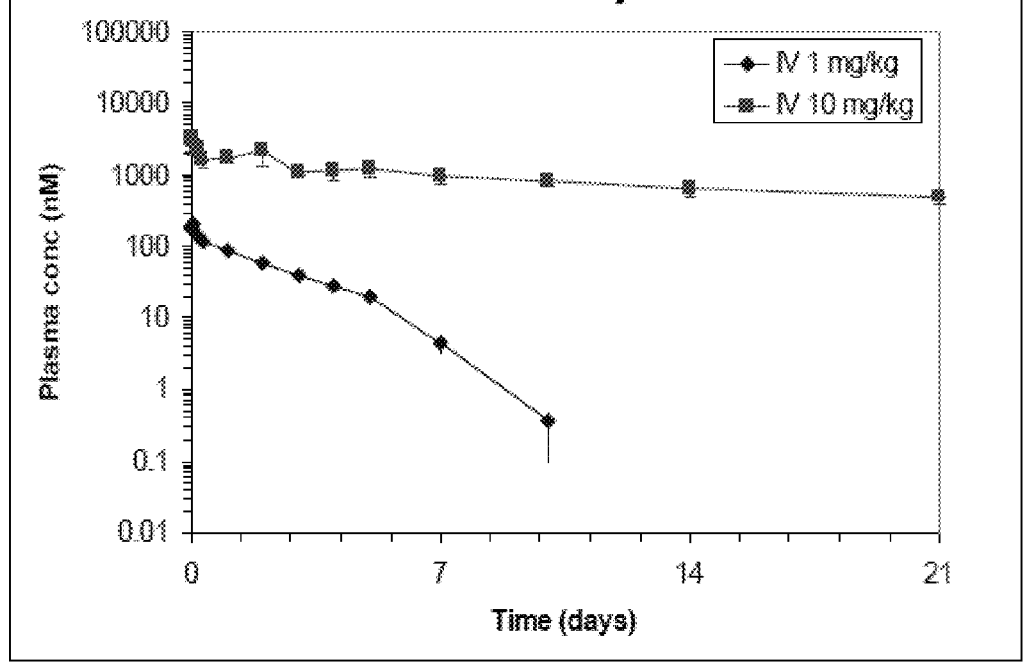
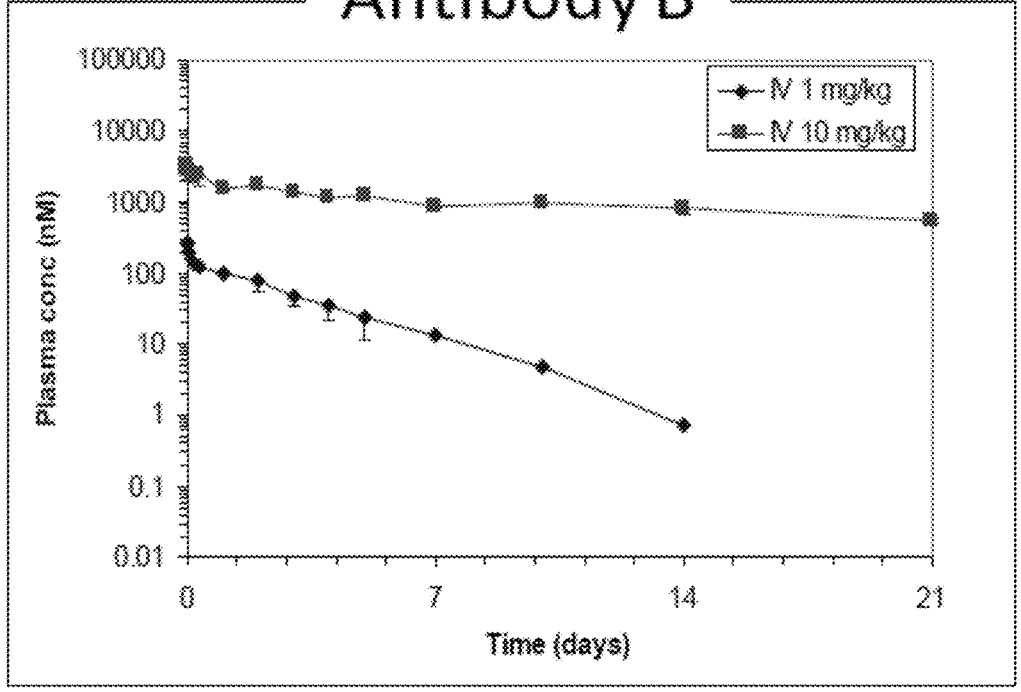

FIGURE 9A
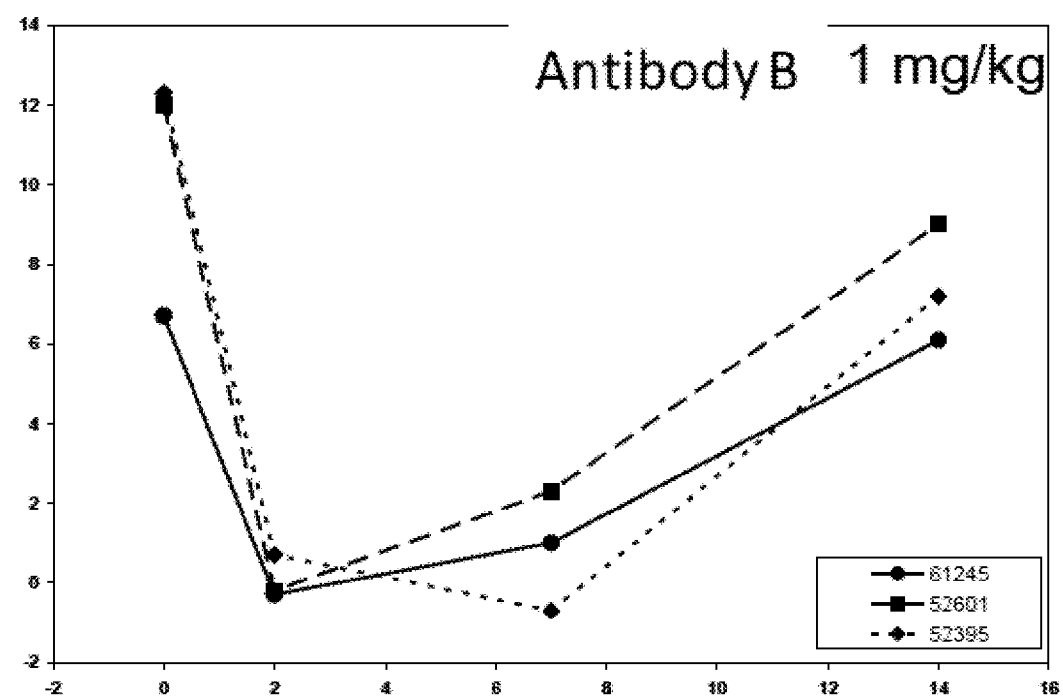
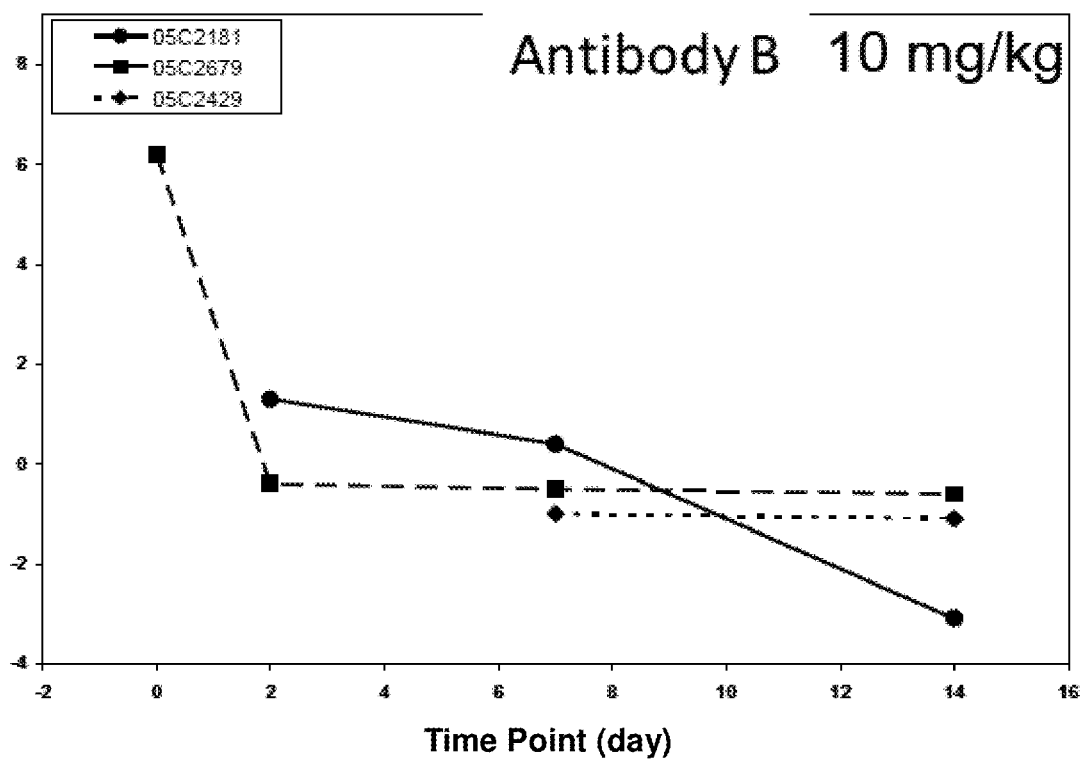
Time Point (day)

FIGURE 10
A.
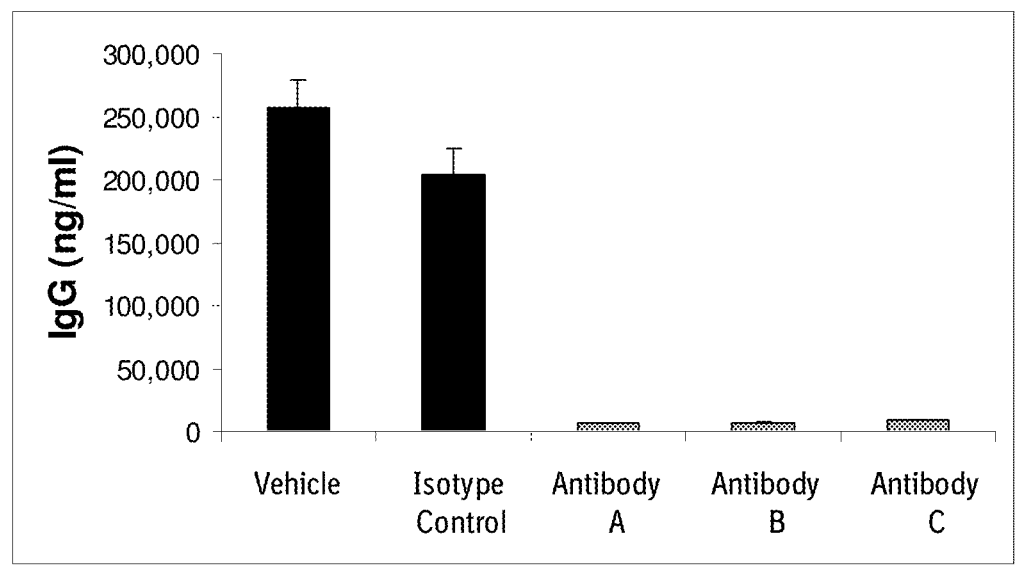
B.
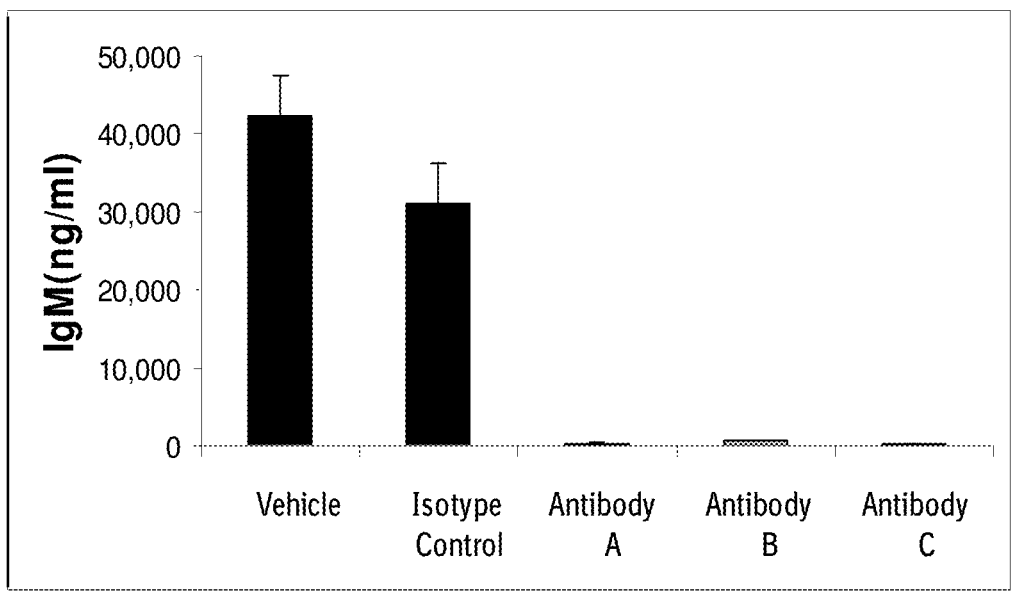

|  | EC50 nM (range) | |
|---|---|---|
|  | Antibody B | 4D11 |
| B cells |  |  |
| Human (n = 6) | 1.8 (1.2 to 2.3) | 0.3 (0.1 to 0.3) |
| Cynomolgus (n = 5) | 2.1 ( 1.4 to 2.9) | 0.7 (0.6 to 0.8) |
| Platelets |  |  |
| Human (n = 5) | 4.6 (2.5 to 5.8) | 0.7 (0.4 to 0.9) |
| Cynomolgus (n = 5) | 3.9 (2.7 to 6.2) | 1.2 (0.9 to 1.7) |

ANTI-CD40 ANTIBODIES

CROSS-REFERENCE TO RELATED APPLICATIONS

This application is a Continuation of U.S. application Ser. No. 15/341,085, filed Nov. 2, 2016, which is a Continuation of U.S. application Ser. No. 15/098,388, filed Apr. 14, 2016, which is a Continuation of U.S. application Ser. No. 14/742,764, filed Jun. 18, 2015, which is a Continuation of U.S. application Ser. No. 14/046,121, filed Oct. 4, 2013, which issued as U.S. Pat. No. 9,090,696, on Jul. 28, 2015, which is a Divisional of U.S. application Ser. No. 13/075,303, filed Mar. 30, 2011, which issued as U.S. Pat. No. 8,591,900, on Nov. 26, 2013, which claims priority to U.S. Provisional Application No. 61/319,574, filed Mar. 31, 2010.

The instant application contains a Sequence Listing which has been submitted in ASCII format via EFS-WEB and is hereby incorporated by reference in its entirety. Said ASCII copy, created on Jul. 6, 2018, is named sequence.txt and is 105 KB.

FIELD OF THE INVENTION

This invention generally relates to humanized anti-CD40 antibodies for diagnostic and therapeutic use. More specifically, humanized anti-CD40 antibodies and methods of use for the treatment of various diseases or disorders characterized by cells expressing CD40 are disclosed. Pharmaceutical compositions and kits comprising the humanized anti-CD40 antibody are also disclosed.

BACKGROUND OF THE INVENTION

CD40 is a 48 kDa type I integral membrane glycoprotein and a member of the tumor necrosis factor (TNF) receptor superfamily. CD40 is expressed on a variety of cell types including normal and neoplastic B cells, interdigitating cells, carcinomas, epithelial cells (e.g. keratinocytes), fibroblasts (e.g. synoviocytes) and platelets. It is also present on monocytes, macrophages, some endothelial cells, and follicular dendritic cells. CD40 is expressed early in B cell ontogeny, appearing on B cell precursors subsequent to the appearance of CD10 and CD19, but prior to expression of CD21, CD23, CD24, and appearance of surface immunoglobulin M (sIgM) (Uckun et al., 1990, Blood 15:2449). CD40 has also been detected on tonsil and bone marrow-derived plasma cells (Pellat-Decounynck et al., 1994, Blood 84:2597).

The ligand of CD40 is CD40L (also referred to as CD154, gp39, and TRAP), a TNF superfamily member. CD40L is a transmembrane protein expressed predominantly on activated CD4$^+$ T cells and a small subset of CD8+ T cells (Reviewed by (Van Kooten C. and Banchereau, 2000).

The interaction of CD40 with CD40L induces both humoral and cell-mediated immune responses. CD40 regulates this ligand-receptor pair to activate B cells and other antigen-presenting cells (APC) including dendritic cells (DCs) (Reviewed by (Toubi and Shoenfeld, 2004); (Kiener, et al., 1995). The function of CD40 on B cells has been studied extensively. Activation of CD40 on B cells induces proliferation, differentiation into antibody secreting cells and isotype switching in germinal centers of secondary lymphoid organs. In vitro studies have shown direct effects of CD40 activation on cytokine production (IL-6, IL-10, TNF-α, LT-α), expression of adhesion molecules and costimulatory receptors (ICAM, CD23, CD80 and CD86), and increased expression of MHC class I, MHC class II, and TAP transporter by B lymphocytes (Liu, et al., 1996). For most of these processes, CD40 acts in concert with either cytokines or other receptor-ligand interactions.

CD40 signaling on monocytes and DCs results in enhanced survival as well as secretion of cytokines (IL-1, IL-6, IL-8, IL-10, IL-12, TNF-α and MIP-1α). CD40 ligation on these APCs also leads to the up-regulation of costimulatory molecules such as (ICAM-1, LFA-3, CD80, and CD86). Activation of CD40 receptors is one of the critical signals that allow the full maturation of DC into efficient APCs driving T cell activation (Banchereau and Steinman, 1998) (Van Kooten C. and Banchereau, 2000).

Recent studies in mouse models showed that CD40 signaling on dendritic cells also plays an important role in the generation of TH17 cells which are considered as mediators of autoimmunity in diseases such as arthritis and multiple sclerosis (Iezzi, et al., 2009) (Perona-Wright, et al., 2009).

The availability of CD40 and CD40L knock-out mice as well as agonistic and antagonistic anti-mouse antibodies offered the possibility to study the role of CD40-CD40L interactions in several disease models. Administration of blocking anti-CD40L has been demonstrated to be beneficial in several models of autoimmunity including spontaneous diseases like lupus nephritis in SNF1 mice or diabetes in NOD mice or in experimentally induced forms of disease like collagen-induced arthritis (CIA) or experimental autoimmune encephalomyelitis (EAE) (Toubi and Shoenfeld, 2004). CIA in mice was inhibited by an anti-CD40L mAb which blocked the development of joint inflammation, serum antibody titers to collagen, the infiltration of inflammatory cells into the subsynovial tissue in addition to the erosion of cartilage and bone (Durie, et al., 1993). Both for lupus nephritis and EAE, it was demonstrated that anti-CD40L could also alleviate ongoing disease, confirming the role of CD40-CD40L in the effector phase of the disease (Kalled, et al., 1998); (Howard, et al., 1999).

The role for CD40-CD40L interactions in the development of EAE was also studied in CD40L-deficient mice that carried a transgenic T cell receptor specific for myelin basic protein. These mice failed to develop EAE after priming with antigen, and CD4+ T cells remained quiescent and produced no INF-γ (Grewal, et al., 1996).

Furthermore, inhibitory antibodies directed against CD40 showed beneficial effects in inflammatory disease models such as EAE. Lamann and colleagues demonstrated that the antagonistic mouse anti-human CD40 mAb mu5D12 and a chimeric version of this mAb effectively prevented clinical expression of chronic demyelinating EAE in outbred marmoset monkeys (Laman, et al., 2002); (Boon, et al., 2001). A follow-up study showed that therapeutic treatment with the chimeric anti-human CD40 antibody reduces MRI-detectable inflammation and delays enlargement of pre-existing brain lesions in the marmoset EAE model (Hart, et al., 2005).

Anti-CD40 antibodies with agonistic activity were tested in mouse models of arthritis with some conflicting results. As expected for an immunostimulatory agent, the agonistic anti-mouse CD40 mAb FGK45 was shown to exacerbate disease in the DBA/1 mouse model of CIA (Tellander, et al., 2000). However, in another chronic CIA model FGK45, and another agonistic anti-mouse CD40 mAb, 3/23, both exhibited positive therapeutic effects (Mauri, et al., 2000). It was postulated by this group that the agonistic antibodies in this therapeutic treatment regimen have a beneficial effect by inducing immune deviation towards a Th2 response with decreased levels of IFN-γ and increased levels of IL-4 and IL-10 (Mauri, et al., 2000).

The prevention of transplant rejection by blocking CD40/CD154 interactions has also been documented. The use of ch5D12, a chimeric anti-CD40 antagonist, in renal allograft studies in rhesus monkeys indicates that antagonism of CD40 is sufficient for disease modification and lengthening mean survival times past 100 days. When ch5D12 was combined with an anti-CD86 antibody and given only at the initiation of the allograft studies followed by prolonged treatment with cyclosporine, mean survival times greater than 4 years were achieved, indicating this combination can potentially induce tolerance (Haanstra, et al., 2005).

Thus, there are ample preclinical studies that provide evidence for the crucial role of the CD40-CD40L dyad in driving an efficient T cell-dependent immune response. Blocking of CD40 signaling is therefore recognized as a suitable and needed therapeutic strategy to suppress a pathogenic autoimmune response in diseases such as RA, multiple sclerosis or psoriasis. However, to date, there are no CD40 antibodies that have been approved for therapeutic intervention of such disorders due to the findings that anti-CD40 antibodies previously in development were shown to have significant side effects. Thus, there remains a significant need for therapeutic agents that can be used to intervene in the action of the CD40-CD40L and block CD40 signaling. This need could be addressed by new humanized anti-CD40 antibodies that specifically bind CD40 and which show the antigen binding specificity, affinity, and pharmacokinetic and pharmacodynamic properties that allow use thereof in therapeutic intervention of CD40 based disorders.

BRIEF SUMMARY OF THE INVENTION

The present invention provides a humanized monoclonal antibody wherein said antibody specifically binds to human CD40 having an antagonistic activity IC50 of less than 1 nM and has no agonism up to 100 μg/ml in B cell proliferation and wherein said antibody is further characterized in that the antibody has an in vivo half life in non-human primates that is at least 10 days.

The humanized monoclonal antibody may be further characterized in that the antibody has a half-life in cynomolgus monkeys of greater than 8 days at a dose of less than 30 mg/kg.

In exemplary embodiments, the antibody of the invention comprises a heavy chain sequence selected from the group consisting of any of SEQ ID NO:1 to SEQ ID NO:4 and a light chain sequence selected from the group consisting of any of SEQ ID NO:5 to SEQ ID NO:8.

In other embodiments, the antibody is a humanized antibody or antigen binding fragment of an antibody having the heavy chain variable region amino acid sequence of any of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, SEQ ID NO: 40, SEQ ID NO: 42, SEQ ID NO: 44, SEQ ID NO: 46, SEQ ID NO: 48, SEQ ID NO. 50 SEQ ID NO: 53, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

In other embodiments, the antibody is a humanized antibody or antigen binding fragment of an antibody that comprises a light chain variable domain amino acid sequence of SEQ ID NO: 5 to SEQ ID NO:8, SEQ ID NO:26, SEQ ID NO:31, SEQ ID NO:36, SEQ ID NO:41, SEQ ID NO:43, SEQ ID NO:45, SEQ ID NO:47, SEQ ID NO:49, SEQ ID NO:50, SEQ ID NO:51, SEQ ID NO:52, SEQ ID NO:54, SEQ ID NO:55, SEQ ID NO:56, SEQ ID NO:74, SEQ ID NO:75, or SEQ ID NO:76.

In specific embodiments, the monoclonal antibody described herein is characterized in that it comprises a heavy chain and a light chain, wherein the heavy chain CDR1 sequence selected from the group consisting of SEQ ID NO: 9 through SEQ ID NO:11, a heavy chain CDR2 sequence selected from the group consisting of SEQ ID NO:12 through SEQ ID NO:15 and a heavy chain CDR3 sequence selected from the group consisting of SEQ ID NO:16 through SEQ ID NO:17; and wherein the light chain CDR1 sequence has a sequence selected from the group consisting of SEQ ID NO:18 through SEQ ID NO:21, a light chain CDR2 sequence of SEQ ID NO:22 through SEQ ID NO:23 and a light chain CDR3 sequence selected from the group consisting of SEQ ID NO:24 through SEQ ID NO:25.

In specific embodiments, the monoclonal antibody described herein is characterized in that it comprises a heavy chain CDR1 sequence of SEQ ID NO: 10, a heavy chain CDR2 sequence of SEQ ID NO:13 and a heavy chain CDR3 sequence of SEQ ID NO:16; and wherein said antibody comprises a light chain CDR1 sequence of SEQ ID NO:19, a light chain CDR2 sequence of SEQ ID NO:22 and a light chain CDR3 sequence of SEQ ID NO:24.

In other specific embodiments, the monoclonal antibody described herein is characterized in that it comprises a heavy chain CDR1 sequence of SEQ ID NO: 9, a heavy chain CDR2 sequence of SEQ ID NO:14 and a heavy chain CDR3 sequence of SEQ ID NO:16; and wherein said antibody comprises a light chain CDR1 sequence of SEQ ID NO:20, a light chain CDR2 sequence of SEQ ID NO:22 and a light chain CDR3 sequence of SEQ ID NO:24.

In another specific embodiment, the monoclonal antibody described herein is characterized in that it comprises a heavy chain CDR1 sequence of SEQ ID NO: 9, a heavy chain CDR2 sequence of SEQ ID NO:14 and a heavy chain CDR3 sequence of SEQ ID NO:16; and wherein said antibody comprises a light chain CDR1 sequence of SEQ ID NO:20, a light chain CDR2 sequence of SEQ ID NO:22 and a light chain CDR3 sequence of SEQ ID NO:24.

In another specific embodiment, the monoclonal antibody described herein is characterized in that it comprises a heavy chain CDR1 sequence of SEQ ID NO: 11, a heavy chain CDR2 sequence of SEQ ID NO:15 and a heavy chain CDR3 sequence of SEQ ID NO:17; and wherein said antibody comprises a light chain CDR1 sequence of SEQ ID NO:21, a light chain CDR2 sequence of SEQ ID NO:23 and a light chain CDR3 sequence of SEQ ID NO:25.

Also described herein are individual sequences for heavy chains of the preferred antibodies of the invention. The invention, for example, relates to an anti-CD40 antibody comprising a heavy chain variable domain sequence of any one of SEQ ID NOs:1 to 4. The anti-CD40 antibody is further characterized as comprising a light chain variable domain sequence of any one of SEQ ID NOs: 5 to SEQ ID NO:8.

Also contemplated is a humanized antibody or antibody fragment having a heavy chain variable domain and a light chain variable region comprising the amino acid sequences of SEQ ID NO:27 and SEQ ID NO:26, respectively; SEQ ID NO:28 and SEQ ID NO:26, respectively; SEQ ID NO:29 and SEQ ID NO:26, respectively; SEQ ID NO:30 and SEQ ID NO:26, respectively; SEQ ID NO:32 and SEQ ID NO:31, respectively; SEQ ID NO:33 and SEQ ID NO:31, respectively; SEQ ID NO:34 and SEQ ID NO:31, respectively;

SEQ ID NO:35 and SEQ ID NO:31, respectively; SEQ ID NO:37 and SEQ ID NO:36, respectively; SEQ ID NO:38 and SEQ ID NO:36, respectively; SEQ ID NO:39 and SEQ ID NO:36, respectively; SEQ ID NO:40 and SEQ ID NO: 36, respectively.

In another embodiment, the invention relates to a humanized antibody or antibody fragment having a heavy chain variable domain and a light chain variable region comprising the amino acid sequences of SEQ ID NO:27 and SEQ ID NO:26, respectively.

In another embodiment, the invention relates to a humanized antibody or antibody fragment having a heavy chain variable domain and a light chain variable region comprising the amino acid sequences of SEQ ID NO:28 and SEQ ID NO:26, respectively.

In another embodiment, the invention relates to a humanized antibody or antibody fragment having a heavy chain variable domain and a light chain variable region comprising the amino acid sequences of SEQ ID NO:29 and SEQ ID NO:26, respectively.

In another embodiment, the invention relates to a humanized antibody or antibody fragment having a heavy chain variable domain and a light chain variable region comprising the amino acid sequences of SEQ ID NO:30 and SEQ ID NO:26, respectively.

In another embodiment, the invention relates to a humanized antibody or antibody fragment having a heavy chain variable domain and a light chain variable region comprising the amino acid sequences of SEQ ID NO:32 and SEQ ID NO:31, respectively.

In another embodiment, the invention relates to a humanized antibody or antibody fragment having a heavy chain variable domain and a light chain variable region comprising the amino acid sequences of SEQ ID NO:33 and SEQ ID NO:31, respectively.

In another embodiment, the invention relates to a humanized antibody or antibody fragment having a heavy chain variable domain and a light chain variable region comprising the amino acid sequences of SEQ ID NO:34 and SEQ ID NO:31, respectively.

In another embodiment, the invention relates to a humanized antibody or antibody fragment having a heavy chain variable domain and a light chain variable region comprising the amino acid sequences of SEQ ID NO:35 and SEQ ID NO:31, respectively.

In another embodiment, the invention relates to a humanized antibody or antibody fragment having a heavy chain variable domain and a light chain variable region comprising the amino acid sequences of SEQ ID NO:37 and SEQ ID NO:36, respectively.

In another embodiment, the invention relates to a humanized antibody or antibody fragment having a heavy chain variable domain and a light chain variable region comprising the amino acid sequences of SEQ ID NO:38 and SEQ ID NO:36, respectively.

In another embodiment, the invention relates to a humanized antibody or antibody fragment having a heavy chain variable domain and a light chain variable region comprising the amino acid sequences of SEQ ID NO:39 and SEQ ID NO:36, respectively.

In another embodiment, the invention relates to a humanized antibody or antibody fragment having a heavy chain variable domain and a light chain variable region comprising the amino acid sequences of SEQ ID NO:40 and SEQ ID NO: 36, respectively.

Another embodiment relates to an isolated antibody or antigen-binding fragment that specifically binds to human CD40, comprising a humanized heavy chain variable domain comprising a framework region having an amino acid sequence at least 90% identical to the amino acid sequence of the framework region of the human variable domain heavy chain amino acid sequence of SEQ ID NO: 27, SEQ ID NO:28, SEQ ID NO:29 or SEQ ID NO:30, and comprising a light chain amino acid sequence at least 90% identical to a corresponding light chain variable domain of SEQ ID NO:26.

Another embodiment relates to an isolated antibody or antigen-binding fragment that specifically binds to human CD40, comprising a humanized heavy chain variable domain comprising a framework region having an amino acid sequence at least 90% identical to the amino acid sequence of the framework region of the human variable domain heavy chain amino acid sequence of SEQ ID NO:32, SEQ ID NO:33, SEQ ID NO:34 or SEQ ID NO:35, and comprising a light chain amino acid sequence at least 90% identical to a corresponding light chain variable of SEQ ID NO:31.

In another aspect, the invention relates to the isolated antibody or antigen-binding fragment described in the embodiment immediately above, wherein the heavy chain amino acid sequence is SEQ ID NO:32; in another embodiment, the heavy chain amino acid sequence is SEQ ID NO:33; in another embodiment, the heavy chain amino acid sequence is SEQ ID NO:34; and in another embodiment, the heavy chain amino acid sequence is SEQ ID NO:35, Also contemplated is an isolated antibody or antigen-binding fragment that specifically binds to human CD40, comprising a humanized heavy chain variable domain comprising a framework region having an amino acid sequence at least 90% identical to the amino acid sequence of the framework region of the human variable domain heavy chain amino acid sequence of SEQ ID NO: 37, SEQ ID NO:38; SEQ ID NO:39 or SEQ ID NO: 40, and comprising a light chain amino acid sequence at least 90% identical to a corresponding light chain of SEQ ID NO:36.

In another aspect, the invention relates to the isolated antibody or antigen-binding fragment described in the embodiment immediately above, wherein the heavy chain amino acid sequence is SEQ ID NO:37; in another embodiment, the heavy chain amino acid sequence is SEQ ID NO:38; in another embodiment, the heavy chain amino acid sequence is SEQ ID NO:39; and in another embodiment, the heavy chain amino acid sequence is SEQ ID NO:40.

The antibodies of the present invention may be further characterized in that said antibodies fail to stimulate production of cytokines from B cells in that absence of CD40L.

The antibodies of the present invention may be further characterized in that said antibodies bind to human CD40 in the presence of 50% human serum with a reduction of on rate less than two fold.

The antibodies of the present invention may be further characterized in that said antibody produces inhibition of IgM and IgG production in a mammal at a concentration of 1 mg/kg.

The antibodies of the present invention may be used in various therapeutic, prophylactic, diagnostic and other methods. For example, the present invention describes a method of blocking the function of human CD40 in a mammal comprising administering to said mammal a composition comprising an antibody of the invention in an amount sufficient to block a CD40 mediated immune response in said mammal.

Also contemplated herein is a method of treating or ameliorating graft vs host disease in a mammal comprising administering to said mammal a composition comprising an antibody of the invention in an amount sufficient to decrease one or more of the symptoms of graft vs. host disease in said animal.

By way of example, the autoimmune or inflammatory disease may include but is not limited to rheumatoid arthritis, multiple sclerosis, proliferative lupus glomerulonephritis, inflammatory bowel disease (IBD), psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis. In exemplary embodiments, the mammal has rheumatoid arthritis.

The methods of the invention may further comprise administering a second therapeutic agent selected from the group consisting of a TNF-antagonist, a disease-modifying antirheumatic drug, a CTLA4-antagonist, an anti-IL-6 receptor mAb and an anti-CD20 mAb.

In specific embodiments, the inflammatory disease or autoimmune disease is an inflammatory disease or autoimmune disease that is associated with cells expressing both CD40 and CD20.

In specific methods the treatment involves administering the antibody composition by a parenteral route of administration.

In specific methods the treatment involves administering the antibody composition intravenously or subcutaneously.

Additional methods of the invention comprise inhibiting antibody production by B cells in a human patient comprising administering to said human patient an effective amount of an anti-CD40 antibody of the invention.

More specifically, the human patient has an inflammatory disease or autoimmune disease that is associated with CD40-expressing cells.

In exemplary embodiments the human patient is suffering from an autoimmune disease selected from the group consisting of autoimmune or inflammatory disease selected from the group consisting of rheumatoid arthritis, multiple sclerosis, proliferative lupus glomerulonephritis, inflammatory bowel disease (IBD), psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

Another method of the invention relates to inhibiting the growth of cells expressing human CD40 antigen, comprising administering the antibody or antigen-binding fragment of the invention to the cells, which antibody or antigen-binding fragment specifically binds to the human cell surface CD40 antigen, wherein the binding of the antibody or antigen-binding fragment to the CD40 antigen inhibits the growth or differentiation of the cells.

Also contemplated is a method of treating a subject having a CD40-associated disorder, comprising administering to the subject the antibody or antigen-binding fragment of the invention, which antibody or antigen-binding fragment specifically binds to human CD40, wherein the binding of the antibody or antigen-binding fragment to CD40 inhibits the growth or differentiation of cells of the CD40-associated disorder. The cells may be but are not limited to B lymphoblastoid cells, pancreatic, lung cells, breast cells, ovarian cells, colon cells, prostate cells, skin cells, head and neck cells, bladder cells, bone cells or kidney cells.

The treatment method for inhibiting growth or differentiation of cells may be useful in the treatment for chronic lymphocytic leukemia, Burkitt's lymphoma, multiple myeloma, a T cell lymphoma, Non-Hodgkin's Lymphoma, Hodgkin's Disease, Waldenstrom's macroglobulinemia or Kaposi's sarcoma.

Also contemplated is a method for inducing depletion of peripheral B cells, comprising administering to the cells the antibody or antigen-binding fragment of the invention, which antibody or antigen-binding fragment specifically binds to a human cell surface CD40 antigen, wherein the binding of the antibody or antigen-binding fragment to the CD40 antigen induces depletion of the cells.

In specific embodiments, the antibody or antigen-binding fragment is administered to a subject having an immune disorder. For example, the immune disorder is rheumatoid arthritis or systemic lupus erythematosus.

Also contemplated is a method of treating rheumatoid arthritis in a subject comprising administering to said subject an antibody of the invention, wherein said antibody is an antagonistic antibody that blocks the function of CD40 in said subject.

Preferably, the antibody is administered in an amount effective to inhibit B cell differentiation and antibody isotype switching in said subject.

In other embodiments, the antibody is administered in an amount effective to inhibit cytokine and chemokine production and up-regulation of adhesion molecules in T-cells and macrophages in said subject. Preferably, the antibody is administered in an amount effective to inhibit activation of dendritic cells in said subject.

In other embodiments, the method is further characterized in that the antibody is administered in an amount effective to inhibit production of proinflammatory cytokines, chemokines, matrix metalloproteinases, prostaglandins, and down-regulate adhesion molecules in non-immune cells in said subject.

In specific embodiments, the antibody is administered in combination with a regimen comprising methotrexate administration and/or administration of Enbrel/Humira.

The subject for receiving the therapy is one that has rheumatoid arthritis and has been non-responsive to methotrexate treatment alone.

In specific embodiments, the method comprises treating said subject with a regimen comprising methotrexate administration and/or administration of Enbrel/Humira.

The method of the invention may be further characterized wherein treatment of said subject with said antagonistic anti-CD40 antibody has a superior efficacy to treatment with methotrexate alone, Enbrel alone, a combination of Enbrel+methotrexate.

The method of the invention may be further characterized wherein treatment of said subject with said antagonistic anti-CD40 antibody has a superior efficacy to treatment with Enbrel+MTX in patients who have had an inadequate response to methotrexate.

In specific embodiments, the antibody is administered in combination with a regimen comprising an anti-TNF agent.

In specific embodiments, subject is characterized as one who has rheumatoid arthritis and has been non-responsive to treatment with an anti-TNF agent alone. In such embodiments, the method may comprise treating said subject with a regimen comprising treatment with an anti-TNF agent in combination with said antagonistic anti-CD40 antibody.

In specific embodiments, the treatment of said subject with said antagonistic anti-CD40 antibody has a superior efficacy to treatment with an anti-TNF agent.

In still other embodiments, the method is characterized in that the treatment of said subject with said antagonistic anti-CD40 antibody has a superior efficacy to treatment with Orencia or Rituxan in patients who have had an inadequate response to an anti-TNF agent alone.

The present invention further contemplates a pharmaceutical composition comprising: (i) the antibody or antigen-binding fragment as described herein; and (ii) a pharmaceutically acceptable excipient. In such compositions, the antibody or antigen binding fragment thereof may advantageously be conjugated to a second agent, such as for example, a cytotoxic agent, a PEG-carrier, an enzyme or a marker.

Also contemplated herein is an isolated polynucleotide encoding a heavy chain variable region amino acid sequence of any of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, SEQ ID NO: 40, SEQ ID NO: 42, SEQ ID NO: 44, SEQ ID NO: 46, SEQ ID NO: 48, SEQ ID. NO. 50, SEQ ID NO: 53, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

Also contemplated herein is an isolated polynucleotide encoding a light chain variable region amino acid sequence of any of SEQ ID NO: 5 to SEQ ID NO:8, SEQ ID NO:26, SEQ ID NO:31, SEQ ID NO:36, SEQ ID NO:41, SEQ ID NO:43, SEQ ID NO:45, SEQ ID NO:47, SEQ ID NO:49, SEQ ID NO:50, SEQ ID NO:51, SEQ ID NO:52, SEQ ID NO:54, SEQ ID NO:55, SEQ ID NO:56, SEQ ID NO:74, SEQ ID NO:75, or SEQ ID NO:76.

The invention further relates to the use of the antibodies described herein for the manufacture of a medicament for blocking the function of human CD40 in a mammal wherein the medicament blocks a CD40 mediated immune response in said mammal.

In an embodiment the invention relates to the manufacture of a medicament for treating or ameliorating graft vs host disease in a mammal.

In exemplary embodiments, the medicament is manufactured for the treatment of an autoimmune or inflammatory disease selected from the group consisting of rheumatoid arthritis, multiple sclerosis, proliferative lupus glomerulonephritis, inflammatory bowel disease (IBD), psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

In some embodiments, the medicament may further comprise a second therapeutic agent selected from the group consisting of a TNF-antagonist, a disease-modifying antirheumatic drug, a CTLA4-antagonist, an anti-IL-6 receptor mAb and an anti-CD20 mAb.

The medicament may be manufactured for use in a parenteral route of administration. The medicament may be manufactured for use intravenously or subcutaneously.

Another embodiment contemplates a use of the antibodies described herein for the manufacture of a medicament for the inhibition of antibody production by B cells in a human patient.

Another embodiment contemplates a use of the antibodies described herein for the manufacture of a medicament for inhibiting the growth and/or differentiation of cells expressing human CD40 antigen.

Another embodiment contemplates a use of the antibodies described herein for the manufacture of a medicament for the treatment of a subject having a CD40-associated disorder wherein the binding of the antibody or antigen-binding fragment in said medicament to CD40 inhibits the growth or differentiation of cells of the CD40-associated disorder.

The medicament may be manufactured for use in the treatment of cells of a CD40-associated disorder selected from B lymphoblastoid cells, pancreatic, lung cells, breast cells, ovarian cells, colon cells, prostate cells, skin cells, head and neck cells, bladder cells, bone cells or kidney cells.

The medicament may be manufactured for use in the treatment of chronic lymphocytic leukemia, Burkitt's lymphoma, multiple myeloma, a T cell lymphoma, Non-Hodgkin's Lymphoma, Hodgkin's Disease, Waldenstrom's macroglobulinemia or Kaposi's sarcoma.

Another embodiment contemplates a use of antibodies of the invention in the manufacture of a medicament for inducing depletion of peripheral B cells wherein the antibody or antigen-binding fragment of the medicament specifically binds to a human cell surface CD40 antigen, wherein the binding of the antibody or antigen-binding fragment to the CD40 antigen induces depletion of the cells.

The medicament may be manufactured for use in the treatment of a subject having an immune disorder.

The medicament may be manufactured for use in the treatment of rheumatoid arthritis or systemic lupus erythematosus.

Another embodiment contemplates a use of antibodies of the invention in the manufacture of a medicament for the treatment of rheumatoid arthritis in a subject.

The medicament may be manufactured for use in inhibition of B cell differentiation and antibody isotype switching in said subject.

The medicament may be manufactured for use in inhibition of cytokine and chemokine production and up-regulation of adhesion molecules in T-cells and macrophages in said subject.

The medicament may be manufactured for use in inhibition of activation of dendritic cells in said subject.

The medicament may be manufactured for use in inhibition of production of proinflammatory cytokines, chemokines, matrix metalloproteinases, prostaglandins, and down-regulation of adhesion molecules in non-immune cells in said subject.

In certain embodiments, the medicament is manufactured as a combination medicament to be administered in combination with a regimen comprising methotrexate administration and/or administration of Enbrel/Humira.

In other embodiments, the medicament is manufactured as a combination medicament and the medicament in addition to comprising the antibodies of the invention further comprises an anti-TNF agent.

BRIEF DESCRIPTION OF SEVERAL VIEWS OF THE DRAWINGS

FIG. 1A. Binding curves and corresponding EC50 values of humanized antibodies on CD40 transfected HEK-293 cells measured by flow cytometry. Antibody B (●=10E2-1 Data, ▲=hIgG1KO Data), Antibody A (●=20E2-12 Data, ▲=hIgG1KO Data), 19B10 (●=19B10-2H11-94-k Data, ▲=hIgG1KO Data), 10F2 (●=10F2-4G-1k Data, ▲=hIgG1KO Data), Antibody C (●=2H11-159-94 Data, ▲=hIgG1KO Data). FIG. 1B. Comparison of binding of Antibody A, Antibody B and Antibody C to CD40 transfected HEK cells measured by flow cytometry. Representative data for one experiment is shown.

FIGS. 3A and 3B: Testing of mouse and humanized antibodies for antagonistic activity in a human primary B cell proliferation assay. FIG. 3A shows representative antibody titration curves and resulting IC50 values is depicted for each mouse precursor antibody. Representative data for one donor is shown. FIG. 3B shows and overlay of inhibition curves depicting antagonism of various humanized anti-CD40 antibodies in comparison to 4D11.

FIG. 4: Summary of the results of testing the humanized antibodies for antagonistic (IC50) and agonistic (SI=stimulation index) activity in a human primary B cell proliferation assay. Various anti-CD40 antibodies, 4D11, G28.5 and 5D12, are shown for comparison.

FIG. 8: Plasma concentration time curves for Antibody A (left panel) and Antibody B (right panel) in cynomolgus monkey following administration of 1 and 10 mg/kg of each antibody. The data is the summary of administration into 3 animals for each antibody.

FIGS. 9A and 9B: Change of percentage of CD86-positive B cells from cynomolgus monkeys prior to administration of (Antibody B) and (Antibody A) and at 3 time points after treatment with each antibody. Antibody B (FIG. 9A) and Antibody A (FIG. 9B) were administered to 3 animals each with 1 mg/kg (left panels) or 10 mg/kg (right panels).

FIG. 10: (A) Human IgG and (B) human IgM levels in NSG mice at 2 weeks after injection of $1.25 \times 10^6$ human PBMC. Mice were treated with vehicle, an isotype control and antibodies Antibody A, Antibody B and Antibody C at a dose of 1 mg/kg one day before transfer of human PBMC

DETAILED DESCRIPTION OF THE INVENTION

Figure 1A:
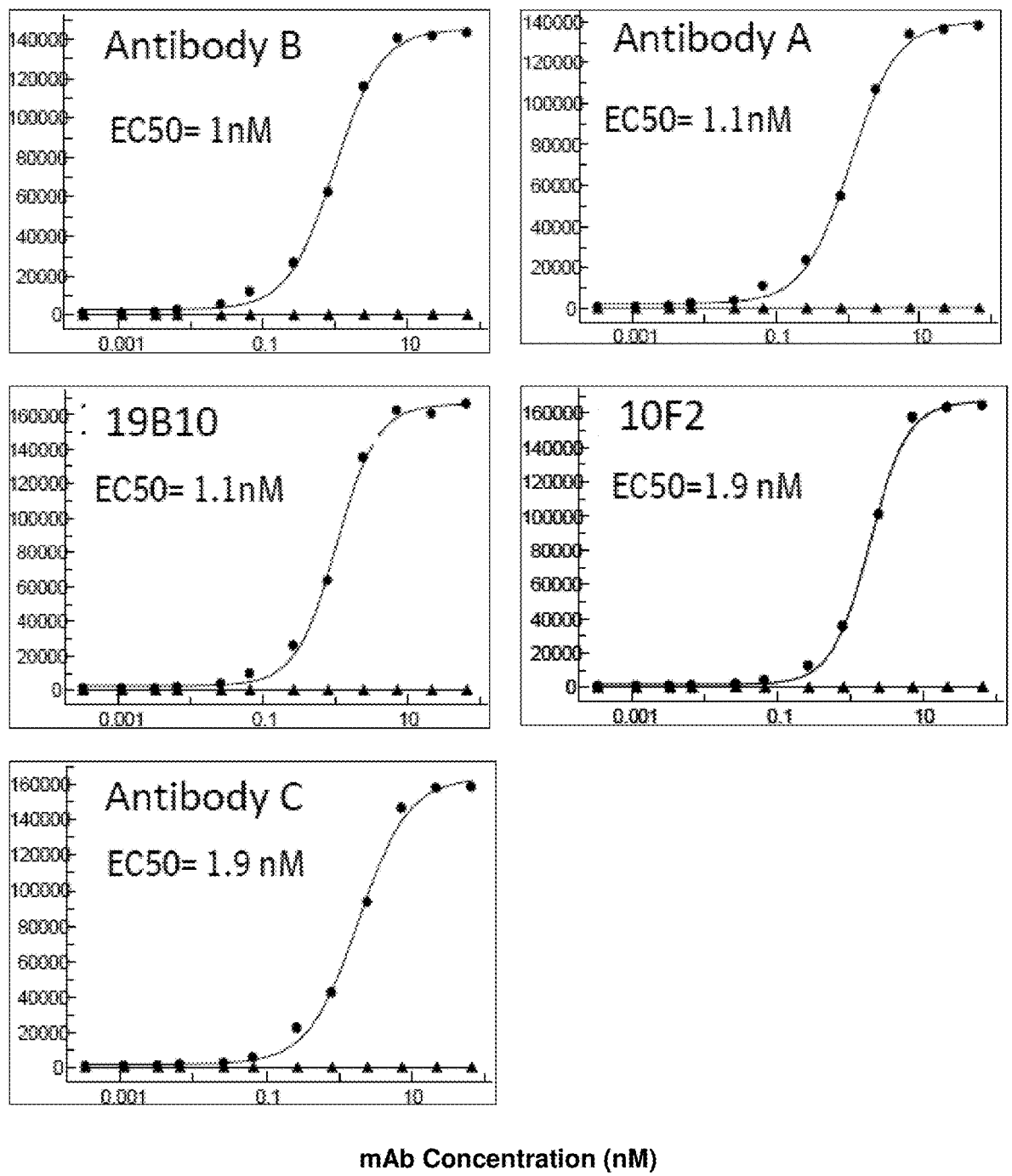
FIGS. 1A and 1B.

CD40 mediated signalling is now recognized as being involved in a variety of target disorders. Despite the availability of a variety of preclinical data showing that intervention in these disorders would be therapeutically beneficial, there remains a need for antagonistic anti-CD40 antibodies that can be used in the treatment of autoimmune diseases. The present invention in preferred embodiments relates to humanized antibodies that recognize CD40. In specific embodiments, the sequence of these humanized antibodies has been identified based on the sequences of certain lead mouse antibodies.

The terms "CD40" and "CD40 surface antigen" refer to an approximately 48 kD glycoprotein expressed on the surface of normal and neoplastic B cells, which acts as a receptor for signals involved in cellular proliferation and differentiation (Ledbetter et al., 1987, J. Immunol. 138:788-785). A cDNA molecule encoding CD40 has been isolated from a library prepared from the Burkitt lymphoma cell line Raji (Stamenkovic et al., 1989, EMBO J. 8:1403).

As used herein, a cell that endogenously expresses CD40 is any cell characterized by the surface expression of CD40, including, but not limited to, normal and neoplastic B cells, interdigitating cells, basal epithelial cells, carcinoma cells, macrophages, endothelial cells, follicular dendritic cells, tonsil cells, and bone marrow-derived plasma cells. In some embodiments, the CD40 molecule is a human CD40 molecule.

The antibodies of the invention specifically bind to human recombinant and native CD40. A humanized monoclonal antibody wherein said antibody specifically binds to human CD40 having an antagonistic activity IC50 of less than 1 nM and has no agonism up to 100 µg/ml in B cell proliferation and wherein said antibody is further characterized in that the antibody has an in vivo half life in non-human primates that is at least 10 days.

Preferably antibody specifically binds to CD40 in CD40-Fc conjugate with an EC50 of less than 1 nM and CD40 in CD40 expressing cells with an EC50 of less than 2.5 nM. The antagonistic properties of the antibody are defined in that it has a B cells or dendritic cell antagonistic activity IC50 of less than 1 nM. The antibody further has superior pharmacokinetic properties having an increased in vivo half life as compared to other anti-CD40 antibodies (e.g., anti-CD40 antibody 4D11).

As used herein, a cell that expresses CD40 is any cell characterized by the surface expression of CD40, including, but not limited to, normal and neoplastic B cells, interdigitating cells, basal epithelial cells, carcinoma cells, macrophages, endothelial cells, follicular dendritic cells, tonsil cells, and bone marrow-derived plasma cells. In some embodiments, the CD40 molecule is a human CD40 molecule.

The antibodies of the present invention recognize specific "CD40 antigen epitope" and "CD40 epitope". As used herein these terms refer to a molecule (e.g., a peptide) or a fragment of a molecule capable of immunoreactivity with an anti-CD40 antibody and, for example, include a CD40 antigenic determinant recognized by the any of the antibodies having a heavy chain/light chain sequence combination of light chain SEQ ID NO.26 with any of heavy chain SEQ ID NOs: 27, 28, 29 or 30; or light chain SEQ ID NO: 31 with any of heavy chain SEQ ID NOs 32, 33, 34 or 35; or light chain SEQ ID NO 36 with any of heavy chain SEQ ID NOs 37, 38, 39 or 40. CD40 antigen epitopes can be included in proteins, protein fragments, peptides or the like. The epitopes are most commonly proteins, short oligopeptides, oligopeptide mimics (i.e., organic compounds that mimic antibody binding properties of the CD40 antigen), or combinations thereof.

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5$^{th}$ Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody dependent cellular cytotoxicity (ADCC), complement dependent cytotoxicity (CDC) and antibody dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-CD40 antibody", "humanized anti-CD40 antibody", and "variant humanized anti-CD40 antibody" are used herein in the broadest sense and specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., CD40 binding.

The term "monoclonal antibody" (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germ line sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "anti-CD40 antibody fragment", "humanized anti-CD40 antibody fragment", "variant humanized anti-CD40 antibody fragment" refer to a portion of a full length anti-CD40 antibody, in which a variable region or a functional capability is retained, for example, specific CD40 epitope binding. Examples of antibody fragments include, but are not limited to, a Fab, Fab', F(ab')$_2$, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the CH1 domain of the heavy chain. Pepsin treatment yields a F(ab')$_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. F(ab')$_2$ antibody fragments are pairs of Fab' fragments linked by cysteine residues in the hinge region. Other chemical couplings of antibody fragments are also known.

"Fv" fragment is contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. The present invention describes specific humanized anti-CD40 antibodies which contain CDRs derived from the murine monoclonal antibodies shown in Tables 3 and 4 inserted between the FRs of human germline sequence heavy and light chain variable domains. It will be understood that certain murine FR residues may be important to the function of the humanized antibodies and therefore certain of the human germline sequence heavy and light chain variable domains residues are modified to be the same as those of the corresponding murine sequence.

In another aspect, a humanized anti-CD40 antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, all of the CDRs are murine sequences as detailed in Tables 1 through 4 herein below and all, or substantially all, of the FRs are those of a human immunoglobulin consensus or germline sequence. In another aspect, a humanized anti-CD40 antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-CD40 antibody can be selected from any class of immunoglobulins, including IgM, IgG, IgD, IgA and IgE, and any isotype, including IgG$_1$, IgG$_2$, IgG$_3$, IgG$_4$, IgA$_1$ and IgA$_2$. For example, the constant domain can be a complement fixing constant domain where it is desired that the humanized antibody exhibit cytotoxic activity, and the isotype is typically IgG$_1$. Where such cytotoxic activity is not desirable, the constant domain may be of another isotype, e.g., IgG$_2$. An alternative humanized anti-CD40 antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly, are IgG1 antibodies in which there is a knock-out of effector functions.

The FRs and CDRs, or HVLs, of a humanized anti-CD40 antibody need not correspond precisely to the parental sequences. For example, one or more residues in the import CDR, or HVL, or the consensus or germ line FR sequence may be altered (e.g., mutagenized) by substitution, insertion or deletion such that the resulting amino acid residue is no longer identical to the original residue in the corresponding position in either parental sequence but the antibody nevertheless retains the function of binding to CD40. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-CD40 antibodies. See, for example, U.S. Pat. Nos. 6,037,454 and 6,054,297.

Human germline sequences are found naturally in human population. A combination of those germline genes generates antibody diversity. Germline antibody sequences for the light chain of the antibody come from conserved human germline kappa or lambda v-genes and j-genes. Similarly the heavy chain sequences come from germ line v-, d- and j-genes (LeFranc, M-P, and LeFranc, G, "The Immunoglobulin Facts Book" Academic Press, 2001).

As used herein, "variant", "anti-CD40 variant", "humanized anti-CD40 variant", or "variant humanized anti-CD40" each refers to a humanized anti-CD40 antibody having at least a heavy chain variable murine CDR from any of the sequences of SEQ ID NO: 1 through 4 or a light chain murine CDR sequence derived from the murine monoclonal antibody as shown in any of SEQ ID NO:5 through SEQ ID NO:8 and FR sequences derived from human consensus sequences. Variants include those having one or more amino acid changes in one or both light chain or heavy chain variable domains, provided that the amino acid change does not substantially impair binding of the antibody to CD40. Exemplary humanized antibodies produced herein include those designated as Antibody A, Antibody B and Antibody C and the various heavy and light chain sequences of the same are shown in SEQ ID NOs 26 through SEQ ID NO:40.

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

The term "antibody performance" refers to factors that contribute to antibody recognition of antigen or the effectiveness of an antibody in vivo. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half life of the antibody.

The term "epitope tagged" when used herein, refers to an anti-CD40 antibody fused to an "epitope tag". An "epitope tag" is a polypeptide having a sufficient number of amino acids to provide an epitope for antibody production, yet is designed such that it does not interfere with the desired activity of the humanized anti-CD40 antibody. The epitope tag is usually sufficiently unique such that an antibody raised against the epitope tag does not substantially cross-react with other epitopes. Suitable tag polypeptides generally contain at least 6 amino acid residues and usually contain about 8 to 50 amino acid residues, or about 9 to 30 residues. Examples of epitope tags and the antibody that binds the epitope include the flu HA tag polypeptide and its antibody 12CA5 (Field et al., 1988 Mol. Cell. Biol. 8: 2159-2165; c-myc tag and 8F9, 3C7, 6E10, G4, B7 and 9E10 antibodies thereto (Evan et al., 1985, Mol. Cell. Biol. 5(12):3610-3616; and Herpes simplex virus glycoprotein D (gD) tag and its antibody (Paborsky et al. 1990, Protein Engineering 3(6): 547-553). In certain embodiments, the epitope tag is a "salvage receptor binding epitope". As used herein, the term "salvage receptor binding epitope" refers to an epitope of the Fc region of an IgG molecule (such as $IgG_1$, $IgG_2$, $IgG_3$, or $IgG_4$) that is responsible for increasing the in vivo serum half-life of the IgG molecule.

In some embodiments, the antibodies of the present invention may be conjugated to a cytotoxic agent. This is any substance that inhibits or prevents the function of cells and/or causes destruction of cells. The term is intended to include radioactive isotopes (such as $I^{131}$, $I^{125}$, $Y^{90}$, and $Re^{186}$), chemotherapeutic agents, and toxins such as enzymatically active toxins of bacterial, fungal, plant, or animal origin, and fragments thereof. Such cytotoxic agents can be coupled to the humanized antibodies of the present invention using standard procedures, and used, for example, to treat a patient indicated for therapy with the antibody.

A "chemotherapeutic agent" is a chemical compound useful in the treatment of cancer. There are numerous examples of chemotherapeutic agents that could be conjugated with the therapeutic antibodies of the present invention. Examples of such chemotherapeutic agents include alkylating agents such a thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatin, auristatins, (including analogues monomethyl-auristatin E and monomethyl-auristatin F); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phiI1, see for example, Agnew, Chem. Intl. Ed. Engl., 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, cam inomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™) raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above. Any one or more of these agents may be conjugated to the humanized antibodies of the present invention to provide a useful therapeutic agent for the treatment of various disorders.

The antibodies also may be conjugated to prodrugs. A "prodrug" is a precursor or derivative form of a pharmaceutically active substance that is less cytotoxic to tumor cells compared to the parent drug and is capable of being enzymatically activated or converted into the more active form. See, for example, Wilman, 1986, "Prodrugs in Cancer Chemotherapy", In Biochemical Society Transactions, 14, pp. 375-382, 615th Meeting Belfast and Stella et al., 1985, "Prodrugs: A Chemical Approach to Targeted Drug Delivery, In: "Directed Drug Delivery, Borchardt et al., (ed.), pp. 247-267, Humana Press. Useful prodrugs include, but are not limited to, phosphate-containing prodrugs, thiophosphate-containing prodrugs, sulfate-containing prodrugs peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

For diagnostic as well as therapeutic monitoring purposes, the antibodies of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to a humanized antibody of the present invention. The label may itself be detectable (e.g., radioisotope labels or fluorescent labels) or, in the case of an enzymatic label, may catalyze chemical alteration of a substrate compound or composition that is detectable. Labeled humanized anti-CD40 antibody can be prepared and used in various applications including in vitro and in vivo diagnostics.

The antibodies of the present invention may be formulated as part of a liposomal preparation in order to effect delivery thereof in vivo. A "liposome" is a small vesicle composed of various types of lipids, phospholipids, and/or surfactant. Liposomes are useful for delivery to a mammal of a compound or formulation, such as a humanized anti-CD40 antibody disclosed herein, optionally, coupled to or in combination with one or more pharmaceutically active agents and/or labels. The components of the liposome are commonly arranged in a bilayer formation, similar to the lipid arrangement of biological membranes.

Certain aspects of the present invention related to isolated nucleic acids that encode one or more domains of the humanized antibodies of the present invention. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is distinguished from the nucleic acid molecule as it exists in natural cells.

In various aspects of the present invention one or more domains of the humanized antibodies will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of humanized anti-CD40 antibody in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-CD40 antibody described herein. This includes chronic and acute disorders or diseases including those pathological conditions that predispose the mammal to the disorder in question. Non-limiting examples or disorders to be treated herein include cancer, hematological malignancies, benign and malignant tumors, leukemias and lymphoid malignancies and inflammatory, angiogenic, autoimmune and immunologic disorders.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia.

As used herein, the term "CD40-associated disorder" or "CD40-associated disease" refers to a condition in which modification or elimination of cells expressing CD40 is indicated. These include CD40-expressing cells demonstrating abnormal proliferation or CD40-expressing cells that are associated with cancerous or malignant growth. More particular examples of cancers that demonstrate abnormal expression of CD40 antigen include B lymphoblastoid cells, Burkitt's lymphoma, multiple myeloma, T cell lymphomas, Kaposi's sarcoma, osteosarcoma, epidermal and endothelial tumors, pancreatic, lung, breast, ovarian, colon, prostate, head and neck, skin (melanoma), bladder, and kidney cancers. Such disorders include, but are not limited to, leukemias, lymphomas, including B cell lymphoma and non-Hodgkin's lymphoma, multiple myeloma, Waldenstrom's macroglobulinemia; solid tumors, including sarcomas, such as osteosarcoma, Ewing's sarcoma, malignant melanoma, adenocarcinoma, including ovarian adenocarcinoma, Kaposi's sarcoma/Kaposi's tumor and squamous cell carcinoma.

A CD40-associated disorder also includes diseases and disorders of the immune system, such as autoimmune disorders and inflammatory disorders. Such conditions include, but are not limited to, rheumatoid arthritis (RA), systemic lupus erythematosus (SLE), scleroderma, Sjogren's syndrome, multiple sclerosis, psoriasis, inflammatory bowel disease (e.g., ulcerative colitis and Crohn's disease), pulmonary inflammation, asthma, and idiopathic thrombocytopenic purara (ITP).

The phrase "arrests the growth of" or "growth inhibitory" when used herein refers to inhibiting growth or proliferation of a cell, especially a neoplastic cell type expressing the CD40 antigen. Thus, growth inhibition, for example, significantly reduces the percentage of neoplastic cells in S phase.

The term "intravenous infusion" refers to introduction of an agent into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an active agent that relieves or ameliorates one or more of the symptoms of the disorder being treated. In doing so it is that amount that has a beneficial patient outcome, for example, a growth arrest effect or causes the deletion of the cell. In one aspect, the therapeutically effective amount has apoptotic activity, or is capable of inducing cell death. In another aspect, the therapeutically effective amount refers to a target serum concentration that has been shown to be effective in, for example, slowing disease progression. Efficacy can be measured in conventional ways, depending on the condition to be treated. For example, in neoplastic diseases or disorders characterized by cells expressing CD40, efficacy can be measured by assessing the time to disease progression, or determining the response rates.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the humanized CD40 antibody copmposition, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

Described and disclosed herein are humanized anti-CD40 antibodies, and compositions and articles of manufacture comprising one or more humanized anti-CD40 antibody of the present invention. Also described are binding agents that include an antigen-binding fragment of a humanized anti-CD40 antibody. The humanized anti-CD40 antibodies and binding agents can arrest the growth of cells, cause the deletion of cells expressing CD40 or otherwise induce or cause a cytotoxic or cytostatic effect on target cells. The humanized anti-CD40 antibodies and binding agents can be used in the treatment of a variety of diseases or disorders characterized by the proliferation of cells expressing the CD40 surface antigen. A humanized anti-CD40 antibody and a CD40 binding agent each includes at least a portion that specifically recognizes a CD40 epitope (i.e., an antigen-binding fragment).

In the initial characterization murine antibodies were selected based on CD40 binding characterization.

From these initial studies, murine antibodies were selected that had the following heavy chain variable regions shown in Table 1 and the light chain variable regions shown in Table 2:

TABLE 1
CD40 Murine Leads-VH Sequences

| 2H11 | EVQLQQSGAELVRPGASVKLSCTASGFNIKDYYVHWVKQRPEKGLEWIGR IDPEDGDSKYAPKFQGKATMTADTSSNTAYLHLSSLTSEDTAVYYCTTSY YVGTYGYWGQGTTLTVSS (SEQ ID NO: 1) |
|---|---|
| 10F2 | EVQLQQSGAELVRPGASVKLSCTASGFNIKDYYIHWVKQRPEKGLEWIGR IDPEDGDTKYDPKFQGKATMTADTSSNTAYLHLSSLTSEDTAVYYCTTSY YVGTYGYWGQGTTLTVSS (SEQ ID NO: 2) |
| 19B10 | EVQLQQSGAELVRPGASVQLSCTASGFNIKDYYVHWVKQRPEKGLEWIGR IDPEDGDTKFAPKFQGKATMTADTSSNTVYLHLSSLTSEDTAVYYCTTSY YVGTYGYWGQGTTLTVSS (SEQ ID NO: 3) |
| 20E2 | EVQLVESGGGLVKPGGSRKLSCAASGFTFSDYGMHWVRQAPEKGLEWVAY ISSGNRIIYYADTVKGRFTISRDNAKNTLFLQMTSLRSEDTALYYCARQD GYRYAMDYWGQGTSVTVSS (SEQ ID NO: 4) |

TABLE 2
CD40 Murine Leads-VK Sequences

| 2H11 | QIVLTQSPAIMSASPGEKVTITCSASSSVSYMLWFQQKPGTSPKLWIYST SNLASGVPARFGGSGSGTSYSLTISRMEAEDAATYYCQQRTFYPYTFGGG TKLEIK (SEQ ID NO: 5) |
|---|---|

```
10F2    QIVLTQSPTIMSASPGEKVIITCSATSSVSYILWFQQKPGTSPKLWIYST
        SNLASGVPARFSGSGSGASYSLTISRMEAEDAATYYCQQRTFYPYTFGGG
        TKLEIK (SEQ ID NO: 6)

19B10   QIVLTQSPAIMSASPGEKVTITCSASSSVSYMLWFQQKPGTSPKLWIYST
        SNLASGVPARFSGSGSGTSYSLTISRMEAEDAATYYCQQRTFYPYTFGGG
        TKLEIK (SEQ ID NO: 7)

20E2    DIVMTQSPSSLTVTAGEKVTMSCKSSQSLLNSGNQKNYLTWHQQKPGQPP
        KLLIYWTSTRESGVPDRFTGSGSGTDFTLTISNLQAEDLAVYYCQNDYTY
        PLTFGAGTKLELK (SEQ ID NO: 8)
```

Human framework sequences were selected for each of the mouse leads based on the framework homology, CDR structure, conserved canonical residues, conserved interface packing residues and other parameters.

The murine heavy chain and light chain CDRs of the various murine antibodies selected antibodies are shown in Table 3 and Table 4, respectively:

TABLE 3

HEAVY CHAIN CDR sequences

| Construct name | H-CDR1 | H-CDR2 | H-CDR3 |
|---|---|---|---|
| 2H11 | GFNIK*DYY*VH<br>SEQ ID NO: 9 | R*IDPEDGDSKYAPKFQG*<br>SEQ ID NO: 12 | *SYYVGTYGY*<br>SEQ ID NO: 16 |
| 10F2 | GFNIK*DYYIH*<br>SEQ ID NO: 10 | R*IDPEDGDTKYDPKFQG*<br>SEQ ID NO: 13 | *SYYVGTYGY*<br>SEQ ID NO: 16 |
| 19B10 | GFNIK*DYYVH*<br>SEQ ID NO: 9 | R*IDPEDGDTKFAPKFQG*<br>SEQ ID NO: 14 | *SYYVGTYGY*<br>SEQ ID NO: 16 |
| 20E2 | GFTFS*DYGMH*<br>SEQ ID NO: 11 | YI*SSGNRH*YYADTVKG<br>SEQ ID NO: 15 | *QDGYRYAMDY*<br>SEQ ID NO: 17 |

The H-CDR1 listed above is using the sequence using the Chothia numbering system (Al-Lazikani et al., (1997) JMB 273, 927-948). The Kabats numbering for the sequences is denoted by the bold italicized text and the IMGT numbering is shown by underlined text of the residues in the above table for CDR1 and CDR2. The sequences for the H-CDR3 for each of 2H11, 10F2 and 19B10 is TTSYYVGTYGY (SEQ ID NO:77) and for 20E2 is ARQDGYRYAMDY (SEQ ID NO:78).

Again, the Chothia numbering system is used in Table 4 with the Kabats numbering for the sequences being denoted by the bold, italicized text and the IMGT numbering is shown by underlined text.

Fabs that showed better or equal binding as compared to the chimeric parent Fab were selected for conversion to IgG. Clones from the 20E2 series were converted to two different IgG formats: a) IgG4DM (double mutant) has two mutations in the Fc/hinge region, Ser228Pro which reduces half-molecule formation and Leu235Glu which further reduces FcγR binding. b) IgG1KO (knock-out of effector functions) has two mutations in the Fc region, Leu234Ala and Leu235Ala, which reduce effector function such as FcγR and complement binding. Both IgG formats are described in the literature. Example 1 describes the humanization of three candidates in further detail. The results of such humanization resulted in humanized antibody sequences, which have the heavy and light chain sequences shown below:

TABLE 4

LIGHT CHAIN CDR sequences

| Construct name | L-CDR1 | L-CDR2 | L-CDR3 |
|---|---|---|---|
| 2H11 | SA*SSSVSYML*<br>SEQ ID NO: 18 | *STSNLAS*<br>SEQ ID NO: 22 | *QQRTFYPYT*<br>SEQ ID NO: 24 |
| 10F2 | SA*TSSVSYIL*<br>SEQ ID NO: 19 | *STSNLAS*<br>SEQ ID NO: 22 | *QQRTFYPYT*<br>SEQ ID NO: 24 |
| 19B10 | SA*SSSVSYML*<br>SEQ ID NO: 20 | *STSNLAS*<br>SEQ ID NO: 22 | *QQRTFYPYT*<br>SEQ ID NO: 24 |
| 20E2 | *KSSQSLLNSGNQKNYLT*<br>SEQ ID NO: 21 | *WTSTRES*<br>SEQ ID NO: 23 | *QNDYTYPLT*<br>SEQ ID NO: 25 |

| Identity | Sequence | SEQ ID NO: |
|---|---|---|
| Antibody A (Light Chain) | DIVMTQSPDSLAVSLGERATMSCKSSQSLLNSGNQKNYLTW HQQKPGQPPKLLIYWTSTRESGVPDRFSGSGSGTDFTLTIS SLQAEDVAVYYCQNDYTYPLTFGGGTKVEIKRTVAAPSVFI FPPSDEQLKSGTASVVCLLNNFYPREAKVQWKVDNALQSGN SQESVTEQDSKDSTYSLSSTLTLSKADYEKHKVYACEVTHQ GLSSPVTKSFNRGEC | 26 |
| Antibody A (Heavy Chain, IgG1KO) | EVQLVESGGGLVKPGGSLRLSCAASGFTFSDYGMHWVRQAP GKGLEWVAYISSGNRIIYYADTVKGRFTISRDNAKNSLYLQ MNSLRAEDTALYYCARQDGYRYAMDYWAQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPGK | 27 |
| Antibody A (Heavy Chain, IgG1) | EVQLVESGGGLVKPGGSLRLSCAASGFTFSDYGMHWVRQAP GKGLEWVAYISSGNRIIYYADTVKGRFTISRDNAKNSLYLQ MNSLRAEDTALYYCARQDGYRYAMDYWAQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPGK | 28 |
| Antibody A (Heavy Chain, IgG4DM) | EVQLVESGGGLVKPGGSLRLSCAASGFTFSDYGMHWVRQAP GKGLEWVAYISSGNRIIYYADTVKGRFTISRDNAKNSLYLQ MNSLRAEDTALYYCARQDGYRYAMDYWAQGTLVTVSSASTK GPSVFPLAPCSRSTSESTAALGCLVKDYFPEPVTVSWNSGA LTSGVHTFPAVLQSSGLYSLSSVVTVPSSSLGTKTYTCNVD HKPSNTKVDKRVESKYGPPCPPCPAPEFEGGPSVFLFPPKP KDTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLTCLVK GFYPSDIAVEWESNGQPENNYKTTPPVLDSDGSFFLYSRLT VDKSRWQEGNVFSCSVMHEALHNHYTQKSLSLSLGK | 29 |
| Antibody A (Heavy, IgG1KOb) | EVQLVESGGGLVKPGGSLRLSCAASGFTFSDYGMHWVRQAP GKGLEWVAYISSGNRITYYADTVKGRFTISRDNAKNSLYLQ MNSLRAEDTALYYCARQDGYRYAMDYWAQGTLVTVSSASTK GPSVFPLAPSSKSTSGGTAALGCLVKDYFPEPVTVSWNSGA TSGVHTFPAVLQSSGLYSLSSVVTVPSSSLGTQTYICNVN HKPSNTKVDKRVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSRDELTKNQVSLTC LVKGFYPSDIAVEWESNGQPENNYKTTPPVLDSDGSFFLYS KLTVDKSRWQQGNVFSCSVMHEALHNHYTQKSLSLSPGK | 30 |
| Antibody B (Light Chain) | DIVMTQSPDSLAVSLGEKVTINCKSSQSLLNSGNQKNYL TWHQQKPGQPPKLLIYHTSTRESGVPDRFSGSGSGTDFT LTISSLQAEDVAVYYCQNDYTYPLTFGGGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC | 31 |
| Antibody B (Heavy Chain, IgG1KO) | EVQLVESGGGLVKPGGSLRLSCAASGFTFSDYGMHWVRQAP GKGLEWVAYISSGNRITYYADTVKGRFTISRDNAKNSLYLQ MNSLRAEDTAVYYCARQDGYRYAMDYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPGK | 32 |
| Antibody B (Heavy Chain, IgG1) | EVQLVESGGGLVKPGGSLRLSCAASGFTFSDYGMHWVRQAP GKGLEWVAYISSGNRITYYADTVKGRFTISRDNAKNSLYLQ MNSLRAEDTAVYYCARQDGYRYAMDYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN | 33 |

| Identity | Sequence | SEQ ID NO: |
|---|---|---|
| | HKPSNTKVDKRVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSNK<br>ALPAPIEKTISKAKGQPREPQVYTLPPSREEMTKNQVSLTC<br>LVKGFYPSDIAVEWESNGQPENNYKTTPPVLDSDGSFFLYS<br>KLTVDKSRWQQGNVFSCSVMHEALHNHYTQKSLSLSPGK | |
| Antibody B (Heavy Chain, IgG4 DM) | EVQLVESGGGLVKPGGSLRLSCAASGFTFSDYGMHWVRQAP<br>GKGLEWVAYISSGNRITYYADTVKGRFTISRDNAKNSLYLQ<br>MNSLRAEDTAVYYCARQDGYRYAMDYWGQGTLVTVSSASTK<br>GPSVFPLAPCSRSTSESTAALGCLVKDYFPEPVTVSWNSGA<br>LTSGVHTFPAVLQSSGLYSLSSVVTVPSSSLGTKTYTCNVD<br>HKPSNTKVDKRVESKYGPPCPPCPAPEFEGGPSVFLFPPKP<br>KDTLMISRTPEVTCVVVDVSQEDPEVQFNWYVDGVEVHNAK<br>TKPREEQFNSTYRVVSVLTVLHQDWLNGKEYKCKVSNKGLP<br>SSIEKTISKAKGQPREPQVYTLPPSQEEMTKNQVSLTCLVK<br>GFYPSDIAVEWESNGQPENNYKTTPPVLDSDGSFFLYSRLT<br>VDKSRWQEGNVFSCSVMHEALHNHYTQKSLSLSLGK | 34 |
| Antibody B (Heavy Chain, IgG1KOb) | EVQLVESGGGLVKPGGSLRLSCAASGFTESDYGMHWVRQAP<br>GKGLEWVAYISSGNRITYYADTVKGRFTISRDNAKNSLYLQ<br>MNSLRAEDTAVYYCARQDGYRYAMDYWGQGTLVTVSSASTK<br>GPSVFPLAPSSKSTSGGTAALGCLVKDYFPEPVTVSWNSGA<br>LTSGVHTFPAVLQSSGLYSLSSVVTVPSSSLGTQTYICNVN<br>HKPSNTKVDKRVEPKSCDKTHTCPPCPAPEAAGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSNK<br>ALPAPIEKTISKAKGQPREPQVYTLPPSRDELTKNQVSLTC<br>LVKGFYPSDIAVEWESNGQPENNYKTTPPVLDSDGSFFLYS<br>KLTVDKSRWQQGNVFSCSVMHEALHNHYTQKSLSLSPGK | 35 |
| Antibody C (Light Chain) | DIQMTQSPSSLSASVGDRVTITCSASSSVSYMLWFQ<br>QKPGKAPKLLIYSTSNLASGVPSRFSGSGSGTDFTL<br>TISSLQPEDFATYYCQQRTFYPYTFGGGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC | 36 |
| Antibody C (Heavy Chain, IgG1KO) | QVQLVQSGAEVKKPGASVKVSCTASGFNIKDYYVHWVKQAP<br>GQGLEWMGRIDPEDGDSKYAPKFQGKATMTADTSTSTVYME<br>LSSLRSEDTAVYYCTTSYYVGTYGYWGQGTLVTVSSASTKG<br>PSVFPLAPSSKSTSGGTAALGCLVKDYFPEPVTVSWNSGAL<br>TSGVHTFPAVLQSSGLYSLSSVVTVPSSSLGTQTYICNVNH<br>KPSNTKVDKRVEPKSCDKTHTCPPCPAPEAAGGPSVFLFPP<br>KPKDTLMISRTPEVTCVVVDVSHEDPEVKFNWYVDGVEVHN<br>AKTKPREEQYNSTYRVVSVLTVLHQDWLNGKEYKCKVSNKA<br>LPAPIEKTISKAKGQPREPQVYTLPPSREEMTKNQVSLTCL<br>VKGFYPSDIAVEWESNGQPENNYKTTPPVLDSDGSFFLYSK<br>LTVDKSRWQQGNVFSCSVMHEALHNHYTQKSLSLSPGK | 37 |
| Antibody C (Heavy Chain, IgG1) | QVQLVQSGAEVKKPGASVKVSCTASGFNIKDYYVHWVKQAP<br>GQGLEWMGRIDPEDGDSKYAPKFQGKATMTADTSTSTVYME<br>LSSLRSEDTAVYYCTTSYYVGTYGYWGQGTLVTVSSASTKG<br>PSVFPLAPSSKSTSGGTAALGCLVKDYFPEPVTVSWNSGAL<br>TSGVHTFPAVLQSSGLYSLSSVVTVPSSSLGTQTYICNVNH<br>KPSNTKVDKRVEPKSCDKTHTCPPCPAPELLGGPSVFLFPP<br>KPKDTLMISRTPEVTCVVVDVSHEDPEVKFNWYVDGVEVHN<br>AKTKPREEQYNSTYRVVSVLTVLHQDWLNGKEYKCKVSNKA<br>LPAPIEKTISKAKGQPREPQVYTLPPSREEMTKNQVSLTCL<br>VKGFYPSDIAVEWESNGQPENNYKTTPPVLDSDGSFFLYSK<br>LTVDKSRWQQGNVFSCSVMHEALHNHYTQKSLSLSPGK | 38 |
| Antibody C (Heavy Chain, IgG4 DM) | QVQLVQSGAEVKKPGASVKVSCTASGFNIKDYYVHWVKQAP<br>GQGLEWMGRIDPEDGDSKYAPKFQGKATMTADTSTSTVYME<br>LSSLRSEDTAVYYCTTSYYVGTYGYWGQGTLVTVSSASTKG<br>PSVFPLAPCSRSTSESTAALGCLVKDYFPEPVTVSWNSGAL<br>TSGVHTFPAVLQSSGLYSLSSVVTVPSSSLGTKTYTCNVDH<br>KPSNTKVDKRVESKYGPPCPPCPAPEFEGGPSVFLFPPKPK<br>DTLMISRTPEVTCVVVDVSQEDPEVQFNWYVDGVEVHNAKT<br>KPREEQFNSTYRVVSVLTVLHQDWLNGKEYKCKVSNKGLPS<br>SIEKTISKAKGQPREPQVYTLPPSQEEMTKNQVSLTCLVKG<br>FYPSDIAVEWESNGQPENNYKTTPPVLDSDGSFFLYSRLTV<br>DKSRWQEGNVFSCSVMHEALHNHYTQKSLSLSLGK | 39 |
| Antibody C (Heavy Chain, IgG1KOb) | QVQLVQSGAEVKKPGASVKVSCTASGFNIKDYYVHWVKQAP<br>GQGLEWMGRIDPEDGDSKYAPKFQGKATMTADTSTSTVYME<br>LSSLRSEDTAVYYCTTSYYVGTYGYWGQGTLVTVSSASTKG | 40 |

-continued

| Identity | Sequence | SEQ ID NO: |
|---|---|---|
| | PSVFPLAPSSKSTSGGTAALGCLVKDYFPEPVTVSWNSGAL | |
| | TSGVHTFPAVLQSSGLYSLSSVVTVPSSSLGTQTYICNVNH | |
| | KPSNTKVDKRVEPKSCDKTHTCPPCPAPEAAGGPSVFLFPP | |
| | KPKDTLMISRTPEVTCVVVDVSHEDPEVKFNWYVDGVEVHN | |
| | AKTKPREEQYNSTYRVVSVLTVLHQDWLNGKEYKCKVSNKA | |
| | LPAPIEKTISKAKGQPREPQVYTLPPSRDELTKNQVSLTCL | |
| | VKGFYPSDIAVEWESNGQPENNYKTTPPVLDSDGSFFLYSK | |
| | LTVDKSRWQQGNVFSCSVMHEALHNHYTQKSLSLSPGK | |

In some embodiments, the antigen-binding fragment can, for example, block proliferation or otherwise arrest the growth of a cell or cause its depletion, death, or otherwise its deletion, for example, through binding the CD40 surface antigen. For example, in T and B cell malignancies, anti-tumor effects (e.g., growth arrest with or without cell deletion or apoptosis) often result when malignant cells are exposed to stimuli that lead to activation of normal lymphocytes. This activation-induced growth arrest has been observed with signals through either antigen receptors or costimulatory receptors (see, e.g., Ashwell et al., 1987, Science 237:61; Bridges et al., 1987, J. Immunol. 139:4242; Page and Defranco, 1988, J. Immunol. 140:3717; and Beckwith et al., 1990, J. Natl. Cancer Inst. 82:501). CD40 stimulation, as a result of specific binding by either antibody or soluble ligand, inhibits B cell lymphoma growth (see, e.g., Funakoshi et al., 1994, Blood 83:2787-2794). Agents that inhibit malignant cell growth in this way and that are directed against the CD40 surface antigen are examples of appropriate agents.

CD40 specific agents include an antigen-binding fragment of a humanized anti-CD40 antibody that binds to CD40 (e.g., human CD40 or a variant thereof). The CD40 specific agents and antibodies can be optionally conjugated with or fused to a cytotoxic or chemotherapeutic agent. In aspects where the humanized antibody binds to the CD40 surface antigen and causes depletion of the CD40 expressing cell types, binding is generally characterized by homing to the CD40 surface antigen cell in vivo. Suitable binding agents bind the CD40 antigen with sufficient affinity and/or avidity such that the CD40 specific agent is useful as a therapeutic agent by specifically targeting a cell expressing the antigen.

In some aspects, the humanized antibody decreases the binding of CD40 ligand to CD40 by at least 45%, by at least 50%, by at least 60% or by at least 75% or at least 80%, or at least 90%, or at least 95%.

In some embodiments, the humanized anti-CD40 antibodies, including antigen-binding fragments thereof, such as heavy and light chain variable domains, comprise an amino acid sequence of the residues derived from the CDRs Antibody A (heavy chain sequence=SEQ ID NO:27; SEQ ID NO:28; SEQ ID NO:29 or SEQ ID NO:30; light chain sequence=SEQ ID NO:26), Antibody B (heavy chain sequence=SEQ ID NO:32; SEQ ID NO:33; SEQ ID NO:34; or SEQ ID NO:35; light chain sequence=SEQ ID NO:31) and Antibody C (heavy chain sequence=SEQ ID NO:37; SEQ ID NO:38; SEQ ID NO:39 or SEQ ID NO:40; light chain sequence=SEQ ID NO:36) described herein above and amino acid residues derived from framework regions of a human immunoglobulin. The humanized anti-CD40 antibodies optionally include specific amino acid substitutions in the consensus or germline framework regions.

The specific substitution of amino acid residues in these framework positions can improve various aspects of antibody performance including binding affinity and/or stability, over that demonstrated in humanized antibodies formed by "direct swap" of CDRs or HVLs into the human germline framework regions, as shown in the examples below.

In some embodiments, the present invention describes other monoclonal antibodies with heavy chain (VH) sequences of SEQ ID NO:1 through SEQ ID NO:4 and light chain (VL) sequences of SEQ ID NO:5 to SEQ ID NO:8 (see Tables 1 and 2 above). The CDR sequence of these murine antibodies are shown in Tables 3 and 4 placing such CDRs into FRs of the human consensus heavy and light chain variable domains will yield useful humanized antibodies of the present invention.

In some specific embodiments, the humanized anti-CD40 antibodies disclosed herein comprise at least a heavy or light chain variable domain comprising the CDRs or HVLs of the murine monoclonal antibodies as shown in Tables 1 through 4 above and the FRs of the human germline heavy and light chain variable domains. In exemplary embodiments, the humanized antibodies created herein are: Antibody A, Antibody B and Antibody C and the various heavy and light chain sequences of the same are shown in SEQ ID NOs 26 through SEQ ID NO:40.

In specific embodiments, antibodies are contemplated that have a heavy chain sequence of any of SEQ ID NO: 27, SEQ ID NO:28, SEQ ID NO:29 or SEQ ID NO:30 in combination with a light chain sequence of SEQ ID NO:26. Alternative antibodies include those that have a heavy chain sequence of SEQ ID NO:32, SEQ ID NO:33, SEQ ID NO:34 or SEQ ID NO SEQ ID NO:35, in combination with a light chain sequence of SEQ ID NO:31. In still additional embodiments, there are provided humanized antibodies that have a heavy chain sequence of SEQ ID NO: 37, SEQ ID NO:38; SEQ ID NO:39 or SEQ ID NO: 40, in combination with a light chain sequence of SEQ ID NO:36.

The CDRs of these sequences are shown in Tables 3 and 4. In specific embodiments, it is contemplated that chimerical antibodies with switched CDR regions (i.e., for example switching one or two CDRs of Antibody A with the analogous CDR from Antibody C) between these exemplary immunoglobulins may yield useful antibodies.

In certain embodiments, the humanized anti-CD40 antibody is an antibody fragment. Various antibody fragments have been generally discussed above and there are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner.

Certain embodiments include an F(ab')$_2$ fragment of a humanized anti-CD40 antibody comprising a have a heavy chain sequence of any of SEQ ID NO:27, SEQ ID NO:28, SEQ ID NO:29 or SEQ ID NO:30 in combination with a light chain sequence of SEQ ID NO:26. Alternative antibodies include those that have a heavy chain sequence of SEQ ID NO:32, SEQ ID NO:33, SEQ ID NO:34 or SEQ ID NO:35, in combination with a light chain sequence of SEQ ID NO:31. In still additional embodiments, there are provided humanized antibodies that have a heavy chain sequence of SEQ ID NO: 37, SEQ ID NO:38; SEQ ID NO:39 or SEQ ID NO: 40, in combination with a light chain sequence of SEQ ID NO:36. Such embodiments can include an intact antibody comprising such an F(ab')$_2$.

In some embodiments, the antibody or antibody fragment includes a constant region that mediates effector function. The constant region can provide antibody-dependent cellular cytotoxicity (ADCC), antibody-dependent cellular phagocytosis (ADCP) and/or complement-dependent cytotoxicity (CDC) responses against a CD40-expressing target cell. The effector domain(s) can be, for example, an Fc region of an Ig molecule. Typically, the CD40 binding agent recruits and/or activates cytotoxic white blood cells (e.g., natural killer (NK) cells, phagocytotic cells (e.g., macrophages), and/or serum complement components).

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of IgM≈IgG$_1$≈IgG$_3$>IgG$_2$>IgG$_4$ and IgG$_1$≈IgG$_3$>IgG$_2$/IgM/IgG$_4$, respectively. Murine immunoglobulins mediate CDC and ADCC/ADCP generally in the order of murine IgM≈IgG$_3$>>IgG$_{2b}$>IgG$_{2a}$>>IgG$_1$ and IgG$_{2b}$>IgG$_{2a}$>IgG$_1$>>IgG$_3$, respectively. In another example, murine IgG$_{2a}$ mediates ADCC while both murine IgG$_{2a}$ and IgM mediate CDC.

Antibody Modifications

The humanized anti-CD40 antibodies and agents can include modifications of the humanized anti-CD40 antibody or antigen-binding fragment thereof. For example, it may be desirable to modify the antibody with respect to effector function, so as to enhance the effectiveness of the antibody in treating cancer. One such modification is the introduction of cysteine residue(s) into the Fc region, thereby allowing interchain disulfide bond formation in this region. The homodimeric antibody thus generated can have improved internalization capability and/or increased complement-mediated cell killing and/or antibody-dependent cellular cytotoxicity (ADCC). See, for example, Caron et al., 1992, J. Exp Med. 176:1191-1195; and Shopes, 1992, J. Immunol. 148:2918-2922. Homodimeric antibodies having enhanced anti-tumor activity can also be prepared using heterobifunctional cross-linkers as described in Wolff et al., 1993, Cancer Research 53: 2560-2565. Alternatively, an antibody can be engineered to contain dual Fc regions, enhancing complement lysis and ADCC capabilities of the antibody. See Stevenson et al., 1989, Anti-Cancer Drug Design 3: 219-230.

Antibodies with improved ability to support ADCC have been generated by modifying the glycosylation pattern of their Fc region. This is possible since antibody glycosylation at the asparagine residue, N297, in the C$_{H2}$ domain is involved in the interaction between IgG and Fcγ receptors prerequisite to ADCC. Host cell lines have been engineered to express antibodies with altered glycosylation, such as increased bisecting N-acetylglucosamine or reduced fucose. Fucose reduction provides greater enhancement to ADCC activity than does increasing the presence of bisecting N-acetylglucosamine. Moreover, enhancement of ADCC by low fucose antibodies is independent of the FcγRIIIa V/F polymorphism.

Modifying the amino acid sequence of the Fc region of antibodies is an alternative to glycosylation engineering to enhance ADCC. The binding site on human IgG$_1$ for Fcγ receptors has been determined by extensive mutational analysis. This led to the generation of humanized IgG$_1$ antibodies with Fc mutations that increase the binding affinity for FcγRIIIa and enhance ADCC in vitro. Additionally, Fc variants have been obtained with many different permutations of binding properties, e.g., improved binding to specific FcγR receptors with unchanged or diminished binding to other FcγR receptors.

Another aspect includes immunoconjugates comprising the humanized antibody or fragments thereof conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used to form useful immunoconjugates include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, the tricothecenes, and the like. A variety of radionuclides are available for the production of radioconjugated humanized anti-CD40 antibodies. Examples include $^{212}$Bi, $^{131}$I, $^{131}$In, $^{90}$Y, and $^{186}$Re.

Conjugates of the humanized anti-CD40 antibody and cytotoxic or chemotherapeutic agent can be made by known methods, using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., 1987, Science 238:1098. Carbon-14-labeled 1-isothiocyanatobenzyl-3-methyldiethylene triaminepentaacetic acid (MX-DTPA) is an exemplary chelating agent for conjugation of radionucleotide to the antibody. Conjugates also can be formed with a cleavable linker.

In another embodiment, the antibody may be conjugated to a "receptor" (such as streptavidin) for utilization in tumor pretargeting. In this procedure, the antibody-receptor conjugate is administered to a patient, followed by removal of unbound conjugate from the circulation using a clearing agent and then administration of a "ligand" that selectively binds the receptor (e.g., avidin), the ligand being conjugated to a cytotoxic agent (e.g., a radionuclide).

The humanized anti-CD40 antibodies disclosed herein can also be formulated as immunoliposomes. Liposomes containing the antibody are prepared by methods known in the art, such as described in Epstein et al., 1985, Proc. Natl. Acad. Sci. USA 82:3688; Hwang et al., 1980, Proc. Natl. Acad. Sci. USA 77:4030; and U.S. Pat. Nos. 4,485,045 and 4,544,545. Liposomes having enhanced circulation time are disclosed, for example, in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody disclosed herein can be conjugated to the liposomes as described in Martin et al., 1982, J. Biol. Chem. 257:286-288 via a disulfide interchange reaction. A chemotherapeutic agent (such as doxorubicin) is optionally contained within the liposome. See, e.g., Gabizon et al., 1989, J. National Cancer Inst. 81(19):1484.

The antibodies described and disclosed herein can also be used in ADEPT (Antibody-Directed Enzyme Prodrug Therapy) procedures by conjugating the antibody to a prodrug-activating enzyme that converts a prodrug (e.g., a peptidyl chemotherapeutic agent), to an active anti-cancer drug. See, for example, WO 81/01145, WO 88/07378, and U.S. Pat. No. 4,975,278. The enzyme component of the immunoconjugate useful for ADEPT is an enzyme capable of acting on a prodrug in such a way so as to covert it into its more active, cytotoxic form. Specific enzymes that are useful in ADEPT include, but are not limited to, alkaline phosphatase for converting phosphate-containing prodrugs into free drugs; arylsulfatase for converting sulfate-containing prodrugs into free drugs; cytosine deaminase for converting non-toxic 5-fluorocytosine into the anti-cancer drug, 5-fluorouracil; proteases, such as serratia protease, thermolysin, subtilisin, carboxypeptidases, and cathepsins (such as cathepsins B and L), for converting peptide-containing prodrugs into free drugs; D-alanylcarboxypeptidases, for converting prodrugs containing D-amino acid substituents; carbohydrate-cleaving enzymes such as β-galactosidase and neuraminidase for converting glycosylated prodrugs into free drugs; β-lactamase for converting drugs derivatized with β-lactams into free drugs; and penicillin amidases, such as penicillin V amidase or penicillin G amidase, for converting drugs derivatized at their amine nitrogens with phenoxyacetyl or phenylacetyl groups, respectively, into free drugs. Alternatively, antibodies having enzymatic activity ("abzymes") can be used to convert the prodrugs into free active drugs (see, for example, Massey, 1987, Nature 328: 457-458). Antibody-abzyme conjugates can be prepared by known methods for delivery of the abzyme to a tumor cell population, for example, by covalently binding the enzyme to the humanized anti-CD40 antibody/heterobifunctional crosslinking reagents discussed above. Alternatively, fusion proteins comprising at least the antigen binding region of an antibody disclosed herein linked to at least a functionally active portion of an enzyme as described above can be constructed using recombinant DNA techniques (see, e.g., Neuberger et al., 1984, Nature 312:604-608).

In certain embodiments, it may be desirable to use a humanized anti-CD40 antibody fragment, rather than an intact antibody, to increase tumor penetration, for example. It may be desirable to modify the antibody fragment in order to increase its serum half life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, covalent modifications of the humanized anti-CD40 antibody are also included. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670, 417, 4,791,192 and 4,179,337.

Humanization and Amino Acid Sequence Variants

Amino acid sequence variants of the anti-CD40 antibody can be prepared by introducing appropriate nucleotide changes into the anti-CD40 antibody DNA, or by peptide synthesis. Such variants include, for example, deletions from, and/or insertions into and/or substitutions of, residues within the amino acid sequences of the anti-CD40 antibodies of the examples herein. Any combination of deletions, insertions, and substitutions is made to arrive at the final construct, provided that the final construct possesses the desired characteristics. The amino acid changes also may alter post-translational processes of the humanized or variant anti-CD40 antibody, such as changing the number or position of glycosylation sites.

A useful method for identification of certain residues or regions of the anti-CD40 antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with CD40 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-CD40 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-CD40 antibody fused to an epitope tag. Other insertional variants of the anti-CD40 antibody molecule include a fusion to the N- or C-terminus of the anti-CD40 antibody of an enzyme or a polypeptide which increases the serum half-life of the antibody.

Another type of variant is an amino acid substitution variant. These variants have at least one amino acid residue in the anti-CD40 antibody molecule removed and a different residue inserted in its place. The sites of greatest interest for substitutional mutagenesis include the hypervariable regions, but FR alterations are also contemplated. Conservative substitutions are shown in Table 5 under the heading of "preferred substitutions". If such substitutions result in a change in biological activity, then more substantial changes, denominated "exemplary substitutions", or as further described below in reference to amino acid classes, may be introduced and the products screened.

TABLE 5

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

It protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-CD40 antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human CD40. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

In some embodiments, it may be desirable to modify the antibodies of the invention to add glycosylations sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-CD40 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-CD40 antibody.

Polynucleotides, Vectors, Host Cells, and Recombinant Methods

Other embodiments encompass isolated polynucleotides that comprise a sequence encoding a humanized anti-CD40 antibody, vectors, and host cells comprising the polynucleotides, and recombinant techniques for production of the humanized antibody. The isolated polynucleotides can encode any desired form of the anti-CD40 antibody including, for example, full length monoclonal antibodies, Fab, Fab', F(ab')$_2$, and Fv fragments, diabodies, linear antibodies, single-chain antibody molecules, and multispecific antibodies formed from antibody fragments.

Some embodiments include isolated polynucleotides comprising sequences that encode an antibody or antibody fragment having the heavy chain variable region amino acid sequence of any of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, or SEQ ID NO: 40. Some embodiments include isolated polynucleotides comprising sequences that encode an antibody or antibody fragment having the light chain variable domain amino acid sequence of SEQ ID NO:26, SEQ ID NO:31, or SEQ ID NO:36.

In one aspect, the isolated polynucleotide sequence(s) encodes an antibody or antibody fragment having a heavy chain variable domain and a light chain variable region comprising the amino acid sequences of SEQ ID NO:27 and SEQ ID NO:26, respectively; SEQ ID NO:28 and SEQ ID NO:26, respectively; SEQ ID NO:29 and SEQ ID NO:26, respectively; SEQ ID NO:30 and SEQ ID NO:26, respectively; SEQ ID NO:32 and SEQ ID NO:31, respectively; SEQ ID NO:33 and SEQ ID NO:31, respectively; SEQ ID NO:34 and SEQ ID NO:31, respectively; SEQ ID NO:35 and SEQ ID NO:31, respectively; SEQ ID NO:37 and SEQ ID NO:36, respectively; SEQ ID NO:38 and SEQ ID NO:36, respectively; SEQ ID NO:39 and SEQ ID NO:36, respectively; SEQ ID NO:40 and SEQ ID NO: 36, respectively.

The polynucleotide(s) that comprise a sequence encoding a humanized anti-CD40 antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The humanized anti-CD40 antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the humanized anti-CD40 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including Saccharomyces and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-CD40 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-CD40 antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-CD40 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-CD40 antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-CD40 antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Humanized anti-CD40 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the rous sarcoma virus long terminal repeat can be used as the promoter.

Another useful element that can be used in a recombinant expression vector is an enhancer sequence, which is used to increase the transcription of a DNA encoding a humanized anti-CD40 antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the humanized anti-CD40 antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-CD40 antibody. One useful transcription termination component is the bovine growth hormone polyadenylation region. See WO94/11026 and the expression vector disclosed therein. In some embodiments, humanized anti-CD40 antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli*

294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for humanized anti-CD40 antibody-encoding vectors. Saccharomyces cerevisiae, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated humanized anti-CD40 antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

In another aspect, expression of humanized anti-CD40 is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for humanized anti-CD40 antibody production and cultured in conventional nutrient media modified as appropriate for inducing promoters, selecting transformants, or amplifying the genes encoding the desired sequences.

The host cells used to produce a humanized anti-CD40 antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657,866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment having a heavy chain variable domain and a light chain variable region comprising the amino acid sequences of SEQ ID NO:27 and SEQ ID NO:26, respectively; SEQ ID NO:28 and SEQ ID NO:26, respectively; SEQ ID NO:29 and SEQ ID NO:26, respectively; SEQ ID NO:30 and SEQ ID NO:26, respectively; SEQ ID NO:32 and SEQ ID NO:31, respectively; SEQ ID NO:33 and SEQ ID NO:31, respectively; SEQ ID NO:34 and SEQ ID NO:31, respectively; SEQ ID NO:35 and SEQ ID NO:31, respectively; SEQ ID NO:37 and SEQ ID NO:36, respectively; SEQ ID NO:38 and SEQ ID NO:36, respectively; SEQ ID NO:39 and SEQ ID NO:36, respectively; SEQ ID NO:40 and SEQ ID NO: 36, respectively. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-CD40 polypeptide (e.g., a heavy chain or light chain variable region), or its complement. Hybridizing nucleic acids of the type described herein can be used, for example, as a cloning probe, a primer, e.g., a PCR primer, or a diagnostic probe.

Some embodiments include isolated polynucleotides including sequences that encode an antibody or antibody fragment having the heavy chain variable region amino acid sequence that is at least 80%, at least 90%, at least 95%, at least 98%, or at least 99% identical to the amino acid sequence of any of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, or SEQ ID NO: 40. Some embodiments include isolated polynucleotides including sequences that encode an antibody or antibody fragment having the light chain variable domain amino acid sequence that is at least 80%, at least 90%, at least 95%, at least 98%, or at least 99% identical to the amino acid sequence of any of SEQ ID NO: 5 to 8, SEQ ID NO:26, SEQ ID NO:31, or SEQ ID NO:36.

In one aspect, the isolated polynucleotide sequence(s) encodes an antibody or antibody fragment having a heavy chain variable domain and a light chain variable region, each including an amino acid sequence that is at least 80%, at least 90%, at least 95%, at least 98%, or at least 99% identical to the amino acid sequence of an antibody or antibody fragment having a heavy chain variable domain and a light chain variable region comprising the amino acid sequences of SEQ ID NO:27 and SEQ ID NO:26, respectively; SEQ ID NO:28 and SEQ ID NO:26, respectively; SEQ ID NO:29 and SEQ ID NO:26, respectively; SEQ ID NO:30 and SEQ ID NO:26, respectively; SEQ ID NO:32 and SEQ ID NO:31, respectively; SEQ ID NO:33 and SEQ ID NO:31, respectively; SEQ ID NO:34 and SEQ ID NO:31, respectively; SEQ ID NO:35 and SEQ ID NO:31, respectively; SEQ ID NO:37 and SEQ ID NO:36, respectively; SEQ ID NO:38 and SEQ ID NO:36, respectively; SEQ ID NO:39 and SEQ ID NO:36, respectively SEQ ID NO:40 and SEQ ID NO: 36, respectively.

In another aspect, the invention relates to a polynuceotide in the embodiment described immediately above, wherein the heavy chain variable domain and the light chain variable region of the encoded antibody or antibody fragment includes an amino acid sequence that is at least 95%, at least 98%, or at least 99% identical to the amino acid sequence of an antibody or antibody fragment having a heavy chain variable domain and a light chain variable region comprising the amino acid sequences of, in one embodiment, SEQ ID NO:27 and SEQ ID NO:26, respectively; in another embodiment, SEQ ID NO:28 and SEQ ID NO:26, respectively; in another embodiment, SEQ ID NO:29 and SEQ ID NO:26, respectively; in another embodiment, SEQ ID NO:30 and SEQ ID NO:26, respectively; in another embodiment, SEQ ID NO:32 and SEQ ID NO:31, respectively; in another embodiment, SEQ ID NO:33 and SEQ ID NO:31, respectively; in another embodiment, SEQ ID NO:34 and SEQ ID NO:31, respectively; in another embodiment, SEQ ID NO:35 and SEQ ID NO:31, respectively; in another embodiment, SEQ ID NO:37 and SEQ ID NO:36, respectively; in another embodiment, SEQ ID NO:38 and SEQ ID NO:36, respectively; in another embodiment, SEQ ID NO:39 and SEQ ID NO:36, respectively; and in another embodiment, SEQ ID NO:40 and SEQ ID NO: 36, respectively.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the CD40 protein (or fragment thereof) to be purified, and thereafter the support is washed with a suitable solvent that will remove substantially all the material in the sample except the CD40 protein, which is bound to the immobilized antibody. Finally, the support is washed with another suitable solvent that will release the CD40 protein from the antibody.

Humanized anti-CD40 antibodies are also useful in diagnostic assays to detect and/or quantify CD40 protein, for example, detecting CD40 expression in specific cells, tissues, or serum.

It will be advantageous in some embodiments, for example, for diagnostic purposes to label the antibody with a detectable detectable moiety. Numerous detectable labels are available, including radioisotopes, fluorescent labels, enzyme substrate labels and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}S$, $^{14}C$, $^{125}I$, $^{3}H$, and $^{131}I$. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, supra, for example. Fluorescence can be quantified using a fluorimeter.

There are various well-characterized enzyme-substrate labels known in the art (see, e.g., U.S. Pat. No. 4,275,149 for a review). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

In another embodiment, the humanized anti-CD40 antibody is used unlabeled and detected with a labeled antibody that binds the humanized anti-CD40 antibody.

The antibodies described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

Diagnostic Kits

A humanized anti-CD40 antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Therapeutic Uses

In another embodiment, a humanized anti-CD40 antibody disclosed herein is useful in the treatment of various disorders associated with the expression of CD40 as described herein.

The humanized anti-CD40 antibody or agent is administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). The humanized anti-CD40 antibody or agent can be administered, for example, as an infusion or as a bolus. Parenteral infusions include intramuscular, intravenous, intraarterial, intraperitoneal, or subcutaneous administration. In addition, the humanized anti-CD40 antibody is suitably administered by pulse infusion, particularly with declining doses of the antibody. In one aspect, the dosing is given by injections, most preferably intravenous or subcutaneous injections, depending in part on whether the administration is brief or chronic.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 20 mg/kg (e.g., 0.1-15 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is that disclosed in WO 94/04188.

The term "suppression" is used herein in the same context as "amelioration" and "alleviation" to mean a lessening of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with CD40 expression.

The antibody need not be, but is optionally, formulated with one or more agents currently used to prevent or treat the disorder in question. The effective amount of such other agents depends on the amount of humanized anti-CD40 antibody present in the formulation, the type of disorder or treatment, and other factors discussed above. These are generally used in the same dosages and with administration routes as used hereinbefore or about from 1 to 99% of the heretofore employed dosages.

CD40-Associated Disorders

The anti-CD40 antibodies or agents are useful for treating or preventing a CD40-expressing cancer or an immunological disorder characterized by expression of CD40, e.g., by inappropriate activation of immune cells (e.g., lymphocytes or dendritic cells). Such expression of CD40 can be due to, for example, increased CD40 protein levels on the cells surface and/or altered antigenicity of the expressed CD40. Treatment or prevention of the immunological disorder, according to the methods described herein, is achieved by administering to a subject in need of such treatment or prevention an effective amount of the anti-CD40 antibody or agent, whereby the antibody (i) binds to activated immune cells that express CD40 and that are associated with the disease state and (ii) exerts a cytotoxic, cytostatic, or immunosuppressive effect on the activated immune cells.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., Fundamental Immunology (William E. Paul ed., Raven Press, N.Y., 3rd ed. 1993).)

Specific examples of such immunological diseases include the following: rheumatoid arthritis, autoimmune demyelinative diseases (e.g., multiple sclerosis, allergic encephalomyelitis), endocrine opthalmopathy, uveoretinitis, systemic lupus erythematosus, myasthenia gravis, Grave's disease, glomerulonephritis, autoimmune hepatological disorder, inflammatory bowel disease (e.g., Crohn's disease or ulcerative colitis), anaphylaxis, allergic reaction, Sjogren's syndrome, type I diabetes mellitus, primary biliary cirrhosis, Wegener's granulomatosis, fibromyalgia, polymyositis, dermatomyositis, inflammatory myositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, acute respiratory distress syndrome, pulmonary inflammation, osteoporosis, delayed type hypersensitivity and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of $Th_1$-lymphocytes or $Th_2$-lymphocytes.

Rheumatoid arthritis (RA) is one of the most common inflammatory autoimmune diseases affecting approximately 1% of the population. While efficacious treatments (e.g. MTX and the anti-TNF agents) are available, there exists great unmet medical need, especially for those patients who do not adequately respond to anti-TNF therapies (about 30% of patients). In addition, up to 50% of patients discontinue TNF-antagonist treatment within 5 years, mainly due to adverse events but also because an increasingly recognized number of patients lose therapeutic benefit. It is thus important to establish effective therapies that target inflammation and joint destruction in RA but do not rely solely on the direct inhibition of TNF. A very attractive approach is to target co-stimulatory cell pathways. One of the key receptor-ligand pairs in costimulation is CD40/CD40L. This system allows interactions between immune cells, and between immune and non-immune cells, all of which are important in the pathogenesis of RA. Blockade of CD40 with an antagonistic antibody of the present invention may have one of more of the following effect in RA:

1) Inhibit B cell differentiation and antibody isotype switching;

2) Inhibit cytokine and chemokine production and up-regulation of adhesion molecules in T-cells and macrophages;

3) Inhibit the activation of dendritic cells and

4) Inhibit production of proinflammatory cytokines, chemokines, matrix metalloproteinases, prostaglandins, and down-regulate adhesion molecules in non-immune cells (e.g. epithelial, endothelial and mesenchymal cells).

Methods of achieving one of more of the above effects are expressly contemplated herein. In addition to RA, the compositions of the present invention will be particularly useful in methods of treatment of Multiple Sclerosis, Psoriasis (including Psoriatic Arthritis), Juvenile Rheumatoid Arthritis. Inflammatory Bowel Disease, Systemic Lupus Erythematosus, and Solid Organ Transplantation.

Rheumatoid Arthritis (RA) is a chronic, systemic autoimmune disease with a prevalence of approximately 1% in adults. The disease continues to cause significant morbidity and premature mortality (mortality is predominantly due to accelerated cardiovascular disease). It has now been identified that joint damage occurs very early in the course of the disease with up to 30% of patients showing radiographic evidence of bony erosions at the time of diagnosis, increasing to 60% after 1 year. Current guidelines recommend initiating therapy with traditional disease-modifying anti-rheumatic drugs (DMARDs) within 3 months after a definite diagnosis has been established. DMARDs have the potential to reduce or prevent joint damage and preserve joint function. Currently, rheumatologists select methotrexate (MTX) as the initial DMARD therapy for most patients.

The TNF-antagonists etanercept (Enbrel®), infliximab (Remicade®), adalimumab (Humira®), the CTLA4-antagonist abatacept (Orencia®), the anti-IL-6 receptor mAb tocilizumab and the anti-CD20 mAb rituximab (Rituxan®) are efficacious in the treatment of RA. Current guidelines generally recommend using biologic DMARDs for the treatment of active RA after an inadequate response to traditional DMARDs.

Recent studies in patients with early aggressive RA without previous MTX treatment showed that the combination of MTX with a TNF-antagonist was superior to each when used as monotherapy. The most striking result was the significant radiological benefit of the combination therapy. Thus, the combination of MTX and TNF-inhibitors should be used in patients at greatest risk for aggressive disease and aggressive phenotype (e.g. high activity score, functional impairment, seropositivity for rheumatoid factor (RF) or anti-cyclic citrullinated peptide antibody (CCP), elevated CRP, radiographic erosions). However, we anticipate that in clinical practice it will be rare that TNF-antagonists will be used as a first-line therapy. A survey of US rheumatologists conducted in April 2005 showed that the factors that most influence the decision to use a TNF-antagonist were: failure of MTX or multiple DMARDs, physician global assessment, functional impairment, and radiographic worsening or erosions. Currently, an estimated 20% of patients with RA receive TNF-inhibitor therapy in the US.

A substantial percentage of RA patients are not adequately helped with the current treatments including biologic therapies, either because of drug intolerance and toxicity or lack of response. Up to 50% of patients discontinue TNF-antagonist treatment within 5 years, mainly due to adverse events but also because an increasingly recognized number of patients lose their response.

In some embodiments, the immunological disorder is a T cell-mediated immunological disorder, such as a T cell disorder in which activated T cells associated with the disorder express CD40. Anti-CD40 antibodies or agents can be administered to deplete such CD40-expressing activated T cells. In a specific embodiment, administration of anti-CD40 antibodies or agents can deplete CD40-expressing activated T cells, while resting T cells are not substantially depleted by the anti-CD40 or agent. In this context, "not substantially depleted" means that less than about 60%, or less than about 70% or less than about 80% of resting T cells are not depleted.

The anti-CD40 antibodies and agents as described herein are also useful for treating or preventing a CD40-expressing cancer. Treatment or prevention of a CD40-expressing cancer, according to the methods described herein, is achieved by administering to a subject in need of such treatment or prevention an effective amount of the anti-CD40 antibody or agent, whereby the antibody or agent (i) binds to CD40-expressing cancer cells and (ii) exerts a cytotoxic or cytostatic effect to deplete or inhibit the proliferation of the CD40-expressing cancer cells.

CD40-expressing cancers that can be treated or prevented by the methods described herein include, for example, leukemia, such as acute leukemia, acute lymphocytic leukemia, acute myelocytic leukemia (e.g., myeloblastic, promyelocytic, myelomonocytic, monocytic, or erythroleukemia), chronic leukemia, chronic myelocytic (granulocytic) leukemia, or chronic lymphocytic leukemia; Polycythemia vera; Lymphoma (e.g., Hodgkin's disease or Non-Hodgkin's disease); multiple myeloma, Waldenstrom's macroglobulinemia; heavy chain disease; solid tumors such sarcomas and carcinomas (e.g., fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, or esophageal carcinoma).

Pharmaceutical Compositions and Administration Thereof

A composition comprising a CD40 binding agent (e.g., an anti-CD40 antibody) can be administered to a subject having or at risk of having an immunological disorder or a CD40-expressing cancer. The invention further provides for the use of a CD40 binding agent (e.g., an anti-CD40 antibody) in the manufacture of a medicament for prevention or treatment of a CD40 expressing cancer or immunological disorder. The term "subject" as used herein means any mammalian patient to which a CD40-binding agent can be administered, including, e.g., humans and non-human mammals, such as primates, rodents, and dogs. Subjects specifically intended for treatment using the methods described herein include humans. The antibodies or agents can be administered either alone or in combination with other compositions in the prevention or treatment of the immunological disorder or CD40-expressing cancer.

Preferred antibodies for use in such pharmaceutical compositions are those that comprise humanized antibody or antibody fragment having the heavy chain variable region amino acid sequence of any of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, or SEQ ID NO: 40.

Some embodiments include isolated polynucleotides comprising sequences that encode an antibody or antibody fragment having the light chain variable domain amino acid sequence of SEQ ID NO:26, SEQ ID NO:31, or SEQ ID NO:36. Particularly preferred humanized antibodies compositions comprise an antibody or antibody fragment having a heavy chain variable domain and a light chain variable region comprising the amino acid sequences of SEQ ID NO:27 and SEQ ID NO:26, respectively; SEQ ID NO:28 and SEQ ID NO:26, respectively; SEQ ID NO:29 and SEQ ID NO:26, respectively; SEQ ID NO:30 and SEQ ID NO:26, respectively; SEQ ID NO:32 and SEQ ID NO:31, respectively; SEQ ID NO:33 and SEQ ID NO:31, respectively; SEQ ID NO:34 and SEQ ID NO:31, respectively; SEQ ID NO:35 and SEQ ID NO:31, respectively; SEQ ID NO:37 and SEQ ID NO:36, respectively; SEQ ID NO:38 and SEQ ID NO:36, respectively; SEQ ID NO:39 and SEQ ID NO:36, respectively; SEQ ID NO:40 and SEQ ID NO:36, respectively. Contemplated within the present invention are isolated poilynucleotides that encode any of the heavy chain sequences of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, SEQ ID NO: 40, SEQ ID NO: 42, SEQ ID NO: 44, SEQ ID NO: 46, SEQ ID NO: 48, SEQ ID NO: 53, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73. Other embodiments are directed to isolated nucleic acids that encode a light chain sequence of any of sequences of SEQ ID NO: 5 to SEQ ID NO:8, SEQ ID NO:26, SEQ ID NO:31, SEQ ID NO:36, SEQ ID NO:41, SEQ ID NO:43, SEQ ID NO:45, SEQ ID NO:47, SEQ ID NO:49, SEQ ID NO:50, SEQ ID NO:51, SEQ ID NO:52, SEQ ID NO:54, SEQ ID NO:55, SEQ ID NO:56, SEQ ID NO:74, SEQ ID NO:75, or SEQ ID NO:76.

In certain embodiments, where the treatment of RA is contemplated, the compositions of the invention may be used in methods for reducing signs and symptoms, inducing a major clinical response and reducing the progression of structural damage in patients with moderately to severely active RA who do not respond adequately to MTX alone. A current exemplary such therapy is: Enbrel/Humira (Data with Humira and Enbrel were obtained in two different patient populations). The compositions of the present invention may be used instead of an Enbrel/Humira therapy or in combination with Enbrel/Humira therapy for subjects that do not respond to MTX alone. Preferably, in such embodiments, the compositions of the invention will have a superior efficacy to Enbrel+MTX in patients who have had an inadequate response to methotrexate as determined for example by: ACR20 at 6 months >85% for compound plus MTX (GS: Enbrel+MTX 71% vs. Placebo+MTX 27%, Humira+MTX at 12 mos 59% vs. Placebo+MTX 24%)*. Additional criteria for superior efficacy of the compositions of the invention may include: Inhibition of progression of structural damage over a period of one year similar to Enbrel (after 52 weeks mean modified Sharp score Humira+MTX 0.1 vs. Placebo+MTX 2.7)*. In still other embodiments, the compositions produce a "Major Clinical Response" superior to Enbrel in patients that have had an inadequate response to methotrexate as measured by ACR70 (20% for Humira+MTX, 4% for Placebo+MTX)*.

In other embodiments, the compositions of the invention may be indicated for reducing signs and symptoms, inducing a major clinical response and reducing the progression of structural damage in patients with moderately to severely active RA who have had an inadequate response to anti-TNF agents. The current Gold standard: non-anti-TNF biologic therapy. Preferably, in such subjects the compositions of the invention possess non-inferior efficacy compared to non-anti-TNF biological (e.g. Orencia, Rituxan) by historical comparison in patients who have had an inadequate response to an anti-TNF agent: ACR20 at 6 months >50% for compound plus DMARD (GS: Orencia+DMARD 50% vs. placebo+DMARD 20%). In still other embodiments, the compositions of the invention inhibit progression of structural damage over a period of one year assessed by accepted X-ray scoring methods for joint erosion and joint space narrowing, similar to Rituxan (after 52 weeks mean modified Sharp score Rituxan+MTX 1.0 vs. Placebo+MTX 2.31).

Various delivery systems are known and can be used to administer the CD40 binding agent. Methods of introduction include but are not limited to intradermal, intramuscular, intraperitoneal, intravenous, subcutaneous, intranasal, epidural, and oral routes. The CD40 binding agent can be administered, for example by infusion, bolus or injection, and can be administered together with other biologically active agents such as chemotherapeutic agents. Administration can be systemic or local. In preferred embodiments, the administration is by subcutaneous injection. Formulations for such injections may be prepared in for example prefilled syringes that may be administered once every other week.

The safety characteristics of the antibodies of the invention will be determined and preferably include one or more features such as: no clinically significant adverse interactions with other medications commonly used to treat Rheumatoid Arthritis (e.g. DMARDs, Steroids, NSAIDs); No greater rate of discontinuations due to safety or tolerability issues compared to Enbrel; Rate of serious infections no greater than anti-TNF agents or other commonly used biologic agents; Frequency and/or severity of injection site reactions or infusion reaction similar to Enbrel; No or minimal development of drug resistance (less than 5%) upon repeat cycles of therapy; No or minimal neutralizing antibodies; No evidence of enhanced platelet aggregation/activation that could lead to thromboembolic events in vivo or platelet/endothelial dysfunction that could lead to bleeding.

In specific embodiments, the CD40 binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-CD40 antibody or agent does not absorb are used.

In other embodiments, the anti-CD40 antibody or agent is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

A CD40 binding agent (e.g., an anti-CD40 antibody) can be administered as pharmaceutical compositions comprising a therapeutically effective amount of the binding agent and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a CD40 binding agent (e.g., an anti-CD40 antibody) in lyophilized form and (b) a second container containing a pharmaceutically acceptable diluent (e.g., sterile water) for injection. The pharmaceutically acceptable diluent can be used for reconstitution or dilution of the lyophilized anti-CD40 antibody or agent. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the CD40 binding agent (e.g., anti-CD40 antibody) that is effective in the treatment or prevention of an immunological disorder or CD40-expressing cancer can be determined by standard clinical techniques. In addition, in vitro assays may optionally be employed to help identify optimal dosage ranges. The precise dose to be employed in the formulation will also depend on the route of administration, and the stage of immunological disorder or CD40-expressing cancer, and should be decided according to the judgment of the practitioner and each patient's circumstances. Effective doses may be extrapolated from dose-response curves derived from in vitro or animal model test systems.

For example, toxicity and therapeutic efficacy of the anti-CD40 antibody or agent can be determined in cell cultures or experimental animals by standard pharmaceutical procedures for determining the ED50 (the dose therapeutically effective in 50% of the population). A CD40-binding agent (e.g., an anti-CD40 antibody) that exhibits a large therapeutic index is preferred. Where a CD40-binding agent exhibits toxic side effects, a delivery system that targets the CD40-binding agent to the site of affected tissue can be used to minimize potential damage non-CD40-expressing cells and, thereby, reduce side effects.

The data obtained from the cell culture assays and animal studies can be used in formulating a range of dosage for use in humans. The dosage of the CD40 binding agent typically lies within a range of circulating concentrations that include the $ED_{50}$ with little or no toxicity. The dosage may vary within this range depending upon the dosage form employed and the route of administration utilized. For any CD40 binding agent used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography, ELISA and the like.

Generally, the dosage of an anti-CD40 antibody or CD40 binding agent administered to a patient with an immunological disorder or CD40-expressing cancer is typically about 0.1 mg/kg to about 100 mg/kg of the subject's body weight. The dosage administered to a subject is about 0.1 mg/kg to about 50 mg/kg, about 1 mg/kg to about 30 mg/kg, about 1 mg/kg to about 20 mg/kg, about 1 mg/kg to about 15 mg/kg, or about 1 mg/kg to about 10 mg/kg of the subject's body weight.

Exemplary doses include, but are not limited to, from 1 ng/kg to 100 mg/kg. In some embodiments, a dose is about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 16 mg/kg. The dose can be administered, for example, daily, once per week (weekly), twice per week, thrice per week, four times per week, five times per week, six times per week, biweekly or monthly, every two months, or every three months. In specific embodiments, the dose is about 0.5 mg/kg/week, about 1 mg/kg/week, about 2 mg/kg/week, about 3 mg/kg/week, about 4 mg/kg/week, about 5 mg/kg/week, about 6 mg/kg/week, about 7 mg/kg/week, about 8 mg/kg/week, about 9 mg/kg/week, about 10 mg/kg/week, about 11 mg/kg/week, about 12 mg/kg/week, about 13 mg/kg/week, about 14 mg/kg/week, about 15 mg/kg/week or about 16 mg/kg/week. In some embodiments, the dose ranges from about 1 mg/kg/week to about 15 mg/kg/week.

In some embodiments, the pharmaceutical compositions comprising the CD40 binding agent can further comprise a therapeutic agent, either conjugated or unconjugated to the binding agent. The anti-CD40 antibody or CD40 binding agent can be co-administered in combination with one or more therapeutic agents for the treatment or prevention of immunological disorders or CD40-expressing cancers. For example, combination therapy can include a cytostatic, cytotoxic, or immunosuppressive agent. Combination therapy can also include, e.g., administration of an agent that targets a receptor or receptor complex other than CD40 on the surface of activated lymphocytes, dendritic cells or CD40-expressing cancer cells. An example of such an agent includes a second, non-CD40 antibody that binds to a molecule at the surface of an activated lymphocyte, dendritic cell or CD40-expressing cancer cell. Another example includes a ligand that targets such a receptor or receptor complex. Typically, such an antibody or ligand binds to a cell surface receptor on activated lymphocytes, dendritic cell or CD40-expressing cancer cell and enhances the cytotoxic or cytostatic effect of the anti-CD40 antibody by delivering a cytostatic or cytotoxic signal to the activated lymphocyte, dendritic cell or CD40-expressing cancer cell.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-CD40 antibody or CD40 binding agent is administered concurrently with a therapeutic agent. In another specific embodiment, the therapeutic agent is administered prior or subsequent to administration of the anti-CD40 antibody or CD40 binding agent, by at least an hour and up to several months, for example at least an hour, five hours, 12 hours, a day, a week, a month, or three months, prior or subsequent to administration of the anti-CD40 antibody or CD40 binding agent.

Useful classes of cytotoxic or immunosuppressive agents include, for example, antitubulin agents, auristatins (e.g., MMAE, or MMAF), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunosuppressive agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE, AEB or AEVB), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, or mitoxantrone.

In some embodiments, the cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to the anti-CD40 antibodies or agents thereof.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in, for example, U.S. Patent Application Publication Nos. 2004-0157782 A1 and 2005-0238649; International Patent Application No. PCT/US03/24209, International Patent Application No. PCT/US02/13435, and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414; the disclosures of which are incorporated by reference herein.

In specific embodiments, the cytotoxic agent is a DNA minor groove binding agent. (See, e.g., U.S. Pat. No. 6,130,237.) For example, in some embodiments, the minor groove binding agent is a CBI compound. In other embodiments, the minor groove binding agent is an enediyne (e.g., calicheamicin).

Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In some embodiments, the therapeutic agent is not a radioisotope.

In some embodiments, the cytotoxic or immunosuppressive agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscamet, or trifluridine.

In other embodiments, the cytotoxic or immunosuppressive agent is tacrolimus, cyclosporine or rapamycin. In further embodiments, the cytotoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, revlimid, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In additional embodiments, the drug is a humanized anti-HER2 monoclonal antibody; RITUXAN (rituximab; Genentech, Inc., South San Francisco, Calif.); a chimeric anti-CD20 monoclonal antibody); OVAREX (AltaRex Corporation, MA); PANOREX (Glaxo Wellcome, NC; a murine IgG2a antibody); Cetuximab Erbitux (Imclone Systems Inc., NY; an anti-EGFR IgG chimeric antibody); Vitaxin (MedImmune, Inc., MD); Campath I/H (Leukosite, MA; a humanized IgG1 antibody); Smart MI95 (Protein Design Labs, Inc., CA; a humanized anti-CD33 IgG antibody); LymphoCide (Immunomedics, Inc., NJ; a humanized anti-CD22 IgG antibody); Smart ID10 (Protein Design Labs, Inc., CA; a humanized anti-HLA-DR antibody); Oncolym (Techniclone, Inc., CA; a radiolabeled murine anti-HLA-Dr10 antibody); Allomune (BioTransplant, CA; a humanized anti-CD2 mAb); Avastin (Genentech, Inc., CA; an anti-VEGF humanized antibody); Epratuzamab (Immunomedics, Inc., NJ and Amgen, CA; an anti-CD22 antibody); and CEAcide (Immunomedics, NJ; a humanized anti-CEA antibody).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti transferrin receptor, p97, MUC1-KLH, CEA, gp100, MART1, Prostate Specific Antigen, IL-2 receptor, CD20, CD52, CD33, CD22, human chorionic gonadotropin, CD38, mucin, P21, MPG, and Neu oncogene product.

In some embodiments, the therapeutic agent is an immunosuppressive agent. The immunosuppressive agent can be, for example, gancyclovir, etanercept, tacrolimus, cyclosporine, rapamycin, cyclophosphamide, azathioprine, mycophenolate mofetil or methotrexate. Alternatively, the immunosuppressive agent can be, for example, a glucocorticoid (e.g., cortisol or aldosterone) or a glucocorticoid analogue (e.g., prednisone or dexamethasone).

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, lanopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, lonapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK and F-104493, Leo Denmark SR-2566, Tanabe T-757 and Teijin TEI-1338.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the humanized anti-CD40 antibody. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1

Production of Humanized Anti-CD40 Antibody

Murine antibodies 20E2, and 2H11 are shown in Tables 1 and 2 herein above. Humanization of the 20E2, and 2H11 clones has been completed. A library was made where human and murine residues were varied in such a way that in any given position there could be either a human or murine residue. Such a library was made for those amino acids that were different between human germline and murine antibody. Only the clones that retain the function of the parent murine antibody were selected.

In this manner, Antibody a, Antibody B and Antibody C were humanized antibodies derived from mouse antibody 20E2 (Antibody A and Antibody B) or 2H11 (Antibody C) cloned into a human IgG1-KO (KO=knock-out)/kappa backbone. IgG1-KO has two mutations in the Fc region, Leu234Ala and Leu235Ala to reduce FcγR and complement binding.

The results of such humanization resulted in various humanized heavy and light chain variable sequences shown below:

```
(variable light chain sequence):
                                                   SEQ ID NO: 41
DIVMTQSPDSLAVSLGERVTMSCKSSQSLLNSGNQKNYLTWHQQKPGQPPKLLIYWTSTRESGVPDRFSGSGSGTDF
TLTISSLQAEDVAVYYCQNDYTYPLTFGGGTKVEIK (variable heavy chain sequence):
                                                   SEQ ID NO: 42
EVQLVKSGGGLVKPGGSLRLSCAASGETFSDYGMHWVRQAPGKGLEWVAYISSGNRIIYYADTVKGRFTISRDNAKN
SLYLQMNSLRAEDTALYYCARQDGYRYAMDYWGQGTLVTVSS (variable light chain sequence)
                                                   SEQ ID NO: 43
DIVMTQSPDSLAVSLGERATMSCKSSQSLLNSGNQKNYLTWHQQKPGQPPKLLIYWTSTRESGVPDRFSGSGSGTDF
TLTISSLQAEDVAVYYCQNDYTYPLTFGGGTKVEIK (variable heavy chain sequence)
                                                   SEQ ID NO: 44
EVQLVESGGGLVKPGGSLRLSCAASGETFSDYGMHWVRQAPGKGLEWVAYISSGNRIIYYADTVKGRFTISRDNAKN
SLYLQMNSLRAEDTALYYCARQDGYRYAMDYWAQGTLVTVSS (variable light chain sequence)
                                                   SEQ ID NO: 45
DIVMTQSPDSLAVSLGEKVTMNCKSSQSLLNSGNQKNYLTWHQQKPGQPPKLLIYWTSTRESGVPDRFSGSGSGTDF
TLTISSLQAEDVAVYYCQNDYTYPLTFGAGTKVEIK
```

-continued (variable heavy chain sequence)
SEQ ID NO: 46
EVQLVESGGGLVKPGGSRRLSCAASGFTESDYGMHWVRQAPGKGLEWVAYISSGNRITYYADTVKGRETISRDNAKN
SLYLQMNSLRAEDTALYYCARQDGYRYAMDYWGQGTLVTVSS .

(variable light chain sequence)
SEQ ID NO: 47
DIVMTQSPDSLAVSLGERVTMNCKSSQSLLNSGNQKNYLTWHQQKPGQPPKLLIYWTSTRESGVPDRFSGSGSGTDF
TLTISSLQAEDVAVYYCQNDYTYPLTFGGGTKVEIK (variable heavy chain sequence)
SEQ ID NO: 48
EVQLVESGGGLVKPGGSLRLSCAASGFTESDYGMHWVRQAPGKGLEWVAYISSGNRITYYADTVKGRETISRDNAKN
SLYLQMNSLRAEDTALYYCARQDGYRYAMDYWGQGTLVTVSS (variable light chain sequence)
SEQ ID NO: 49
DIVMTQSPDSLAVSLGERVTMNCKSSQSLLNSGNQKNYLTWHQQKPGQPPKLLIYWTSTRESGVPDRFSGSGSGTDF
TLTISSLQAEDVAVYYCQNDYTYPLTFGAGTKVEIK (variable light chain sequence)
SEQ ID NO: 50
EVQLVESGGGLVKPGGSRRLSCAASGFTESDYGMHWVRQAPGKGLEWVAYISSGNRITYYADTVKGRETISRDNAKN
SLYLQMNSLRAEDTAVYYCARQDGYRYAMDYWGQGTLVTVSS (variable light chain sequence)
SEQ ID NO: 51
DIVMTQSPDSLAVSLGEKVTMNCKSSQSLLNSGNQKNYLTWHQQKPGQPPKLLIYWTSTRESGVPDRFSGSGSGTDF
TLTISSLQAEDLAVYYCQNDYTYPLTFGAGTKVEIK .

(variable light chain sequence)
SEQ ID NO: 52
DIVMTQSPDSLAVSLGEKVTINCKSSQSLLNSGNQKNYLTWHQQKPGQPPKLLIYWTSTRESGVPDRFSGSGSGTDF
TLTISSLQAEDVAVYYCQNDYTYPLTFGGGTKVEIK (variable heavy chain sequence)
SEQ ID NO: 53
EVQLVESGGGLVKPGGSLRLSCAASGFTESDYGMHWVRQAPGKGLEWVAYISSGNRITYYADTVKGRETISRDNAKN
SLYLQMNSLRAEDTAVYYCARQDGYRYAMDYWGQGTLVTVSS (variable light chain sequence)
SEQ ID NO: 54
QIQMTQSPSSLSASVGDRVTITCSASSSVSYMLWFQQKPGKAPKLWIYSTSNLASGVPARFSGSGSGTDFTLTISSL
QPEDFATYYCQQRTFYPYTEGGGTKVEIK (variable light chain sequence)
SEQ ID NO: 55
DIQMTQSPSSLSASVGDRVTITCSASSSVSYMLWFQQKPGKAPKLLIYSTSNLASGVPARFSGSGSGTDFTLTISSL
QPEDFATYYCQQRTFYPYTEGGGTKVEIK (variable light chain sequence)
SEQ ID NO: 56
DIQMTQSPSSLSASVGDRVTITCSASSSVSYMLWFQQKPGKAPKLLIYSTSNLASGVPSRFSGSGSGTDFTLTISSL
QPEDFATYYCQQRTFYPYTFGGGTKVEIK (variable heavy chain sequence)
SEQ ID NO: 57
QVQLVQSGAEVKKPGASVKVSCTASGENTTDYYVHWVKQRPGQGLEWMGRIDPEDGDSKYAPKFQGKATMTADTSTS
TVYMELSSLRSEDTAVYYCTTSYYVGTYGYWGQGTLVTVSS .

(variable heavy chain sequence)
SEQ ID NO: 58
QVQLVQSGAEVKKPGASVKVSCTASGENTKDYYVHWVKQAPGQGLEWMGRIDPEDGDSKYAPKFQGKATMTADTSTS
TVYMELSSLRSEDTAVYYCTTSYYVGTYGYWGQGTLVTVSS (variable heavy chain sequence)
SEQ ID NO: 59
QVQLVQSGAEVKKPGASVKVSCTASGENTTDYYVHWVKQRPGQGLEWMGRIDPEDGDSKYAPKFQGKVTMTADTSTS
TVYMELSSLRSEDTAVYYCTTSYYVGTYGYWGQGTLVTVSS .

(variable heavy found sequence)
SEQ ID NO: 60
QVQLVQSGAEVKKPGASVKVSCTASGENTKDYYVHWVKQAPGQGLEWIGRIDPEDGDSKYAPKFQGKATMTADTSTS
TVYMELSSLRSEDTAVYYCTTSYYVGTYGYWGQGTLVTVSS (variable heavy sequence)
SEQ ID NO: 61
QVQLVQSGAEVKKPGASVKVSCTASGENTTDYYVHWVKQAPGQGLEWMGRIDPEDGDSKYAPKFQGKATMTADTSTS
TVYMELSSLRSEDTAVYYCTTSYYVGTYGYWGQGTLVTVSS (variable heavy sequence):
SEQ ID NO: 62
QVQLVQSGAEVKKPGASVKVSCTASGENTTDYYVHWVKQRPGQGLEWMGRIDPEDGDTKFAPKFQGKATMTADTSTS
TVYMELSSLRSEDTAVYYCTTSYYVGTYGYWGQGTLVTVSS (variable heavy sequence)
SEQ ID NO: 63
QVQLVQSGAEVKKPGASVKVSCTASGENTTDYYVHWVKQRPGQGLEWMGRIDPEDGDTKFAPKFQGKVTMTADTSTS
TVYMELSSLRSEDTAVYYCTTSYYVGTYGYWGQGTLVTVSS (variable heavy sequence)
SEQ ID NO: 64
QVQLVQSGAEVKKPGASVKVSCTASGENTKDYYVHWVKQAPGQGLEWIGRIDPEDGDTKFAPKFQGKATMTADTSTS
TVYMELSSLRSEDTAVYYCTTSYYVGTYGYWGQGTLVTVSS (variable heavy sequence)
SEQ ID NO: 65
QVQLVQSGAEVKKPGASVKVSCTASGENTKDYYVHWVKQAPGQGLEWMGRIDPEDGDTKFAPKFQGKATMTADTSTS
TVYMELSSLRSEDTAVYYCTTSYYVGTYGYWGQGTLVTVSS (variable heavy sequence)
SEQ ID NO: 66
QVQLVQSGAEVKKPGASVKVSCTASGENITDYYVHWVKQAPGQGLEWMGRIDPEDGDTKFAPKFQGKATMTADTSTS
TVYMELSSLRSEDTAVYYCTTSYYVGTYGYWGQGTLVTVSS (variable heavy sequence)
SEQ ID NO: 67
EVQLVQSGAEVKKPGATVKISCKVSGENIKDYYIHWVKQRPGKGLEWMGRIDPEDGDTKYDPKFQGRVTMTADTSTD
TAYMELSSLRSEDTAVYYCTTSYYVGTYGYWGQGTTVTVSS (variable heavy sequence)
SEQ ID NO: 68
EVQLVQSGAEVKKPGATVKISCTVSGENIKDYYIHWVKQRPGKGLEWMGRIDPEDGDTKYDPKFQGRVTMTADTSTD
TAYMELSSLRSEDTAVYYCTTSYYVGTYGYWGQGTTVTVSS (variable heavy sequence)
SEQ ID NO: 69
EVQLVQSGAEVKKPGATVKISCTVSGENIKDYYIHWVKQRPGKGLEWMGRIDPEDGDTKYDPKFQGKVTMTADTSTD
TAYMELSSLRSEDTAVYYCTTSYYVGTYGYWGQGTTVTVSS (variable heavy sequence)
SEQ ID NO: 70
EVQLVQSGAEVKKPGATVKISCTVSGENIKDYYIHWVKQAPGKGLEWMGRIDPEDGDTKYDPKFQGKATMTADTSTD
TAYMELSSLRSEDTAVYYCTTSYYVGTYGYWGQGTTVTVSS (variable heavy sequence)
SEQ ID NO: 71
EVQLVQSGAEVKKPGATVKISCTVSGENIKDYYIHWVKQRPGKGLEWMGRIDPEDGDTKYDPKFQGKATMTADTSTD
TAYMELSSLRSEDTAVYYCTTSYYVGTYGYWGQGTTVTVSS (variable heavy sequence)
SEQ ID NO: 72
EVQLVQSGAEVKKPGATVKISCTVSGENIKDYYIHWVKQAPGKGLEWIGRIDPEDGDTKYDPKFQGKATMTADTSTD
TAYMELSSLRSEDTAVYYCTTSYYVGTYGYWGQGTTVTVSS (variable heavy sequence)
SEQ ID NO: 73
EVQLVQSGAEVKKPGATVKISCKVSGENIKDYYIHWVQQAPGKGLEWMGRIDPEDGDTKYDPKFQGRVTMTADTSTD
TAYMELSSLRSEDTAVYYCTTSYYVGTYGYWGQGTTVTVSS (variable light sequence) 1 from antibody 10F2Hum:
SEQ ID NO: 74
DIQMTQSPSSLSASVGDRVTITCSATSSVSYILWFQQKPGKAPKLLIYSTSNLASGVPSRFSGSGSGTDFTLTISSL
QPEDFATYYCQQRTFYPYTFGGGTKVEIK (variable light sequence) 2 from antibody 10F2Hum:
SEQ ID NO: 75
DIQMTQSPSSLSASVGDRVTITCSATSSVSYILWFQQKPGKAPKLLIYSTSNLASGVPARFSGSGSGTDFTLTISSL
QPEDFATYYCQQRTFYPYTFGGGTKVEIK (variable light sequence)
SEQ ID NO: 76
QIQMTQSPSSLSASVGDRVTITCSATSSVSYILWFQQKPGKAPKLWIYSTSNLASGVPARFSGSGSGTDFTLTISSL
QPEDFATYYCQQRTFYPYTFGGGTKVEIK Exemplary humanized antibodies of the present invention are those that have the heavy and light chain sequences set forth in the following table. The bold underlined sequences in the following table are the variable domains whereas the normal, non-underlined sequences are the constant domains:

| Identity | Sequence | SEQ ID NO: |
| --- | --- | --- |
| Antibody A (Light Chain) | DIVMTQSPDSLAVSLGERATMSCKSSQSLLNSGNQKNYLTW HQQKPGQPPKLLIYWTSTRESGVPDRFSGSGSGTDFTLTIS SLQAEDVAVYYCQNDYTYPLTFGGGTKVEIKRTVAAPSVFI FPPSDEQLKSGTASVVCLLNNFYPREAKVQWKVDNALQSGN SQESVTEQDSKDSTYSLSSTLTLSKADYEKHKVYACEVTHQ GLSSPVTKSFNRGEC | 26 |
| Antibody A (Heavy Chain, IgG1KO) | EVQLVESGGGLVKPGGSLRLSCAASGFTFSDYGMHWVRQAP GKGLEWVAYISSGNRIIYYADTVKGRFTISRDNAKNSLYLQ MNSLRAEDTALYYCARQDGYRYAMDYWAQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPGK | 27 |
| Antibody A (Heavy Chain, IgG1) | EVQLVESGGGLVKPGGSLRLSCAASGFTFSDYGMHWVRQAP GKGLEWVAYISSGNRIIYYADTVKGRFTISRDNAKNSLYLQ MNSLRAEDTALYYCARQDGYRYAMDYWAQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPGK | 28 |
| Antibody A (Heavy Chain, IgG4DM) | EVQLVESGGGLVKPGGSLRLSCAASGFTFSDYGMHWVRQAP GKGLEWVAYISSGNRIIYYADTVKGRFTISRDNAKNSLYLQ MNSLRAEDTALYYCARQDGYRYAMDYWAQGTLVTVSSASTK GPSVFPLAPCSRSTSESTAALGCLVKDYFPEPVTVSWNSGA LTSGVHTFPAVLQSSGLYSLSSVVTVPSSSLGTKTYTCNVD HKPSNTKVDKRVESKYGPPCPPCPAPEFEGGPSVFLFPPKP KDTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLTCLVK GFYPSDIAVEWESNGQPENNYKTTPPVLDSDGSFFLYSRLT VDKSRWQEGNVFSCSVMHEALHNHYTQKSLSLSLGK | 29 |
| Antibody A (Heavy, IgG1KOb) | EVQLVESGGGLVKPGGSLRLSCAASGFTFSDYGMHWVRQAP GKGLEWVAYISSGNRITYYADTVKGRFTISRDNAKNSLYLQ MNSLRAEDTALYYCARQDGYRYAMDYWAQGTLVTVSSASTK GPSVFPLAPSSKSTSGGTAALGCLVKDYFPEPVTVSWNSGA TSGVHTFPAVLQSSGLYSLSSVVTVPSSSLGTQTYICNVN HKPSNTKVDKRVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSRDELTKNQVSLTC LVKGFYPSDIAVEWESNGQPENNYKTTPPVLDSDGSFFLYS KLTVDKSRWQQGNVFSCSVMHEALHNHYTQKSLSLSPGK | 30 |
| Antibody B (Light Chain) | DIVMTQSPDSLAVSLGEKVTINCKSSQSLLNSGNQKNYL TWHQQKPGQPPKLLIYHTSTRESGVPDRFSGSGSGTDFT LTISSLQAEDVAVYYCQNDYTYPLTFGGGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC | 31 |
| Antibody B (Heavy Chain, IgG1KO) | EVQLVESGGGLVKPGGSLRLSCAASGFTFSDYGMHWVRQAP GKGLEWVAYISSGNRITYYADTVKGRFTISRDNAKNSLYLQ MNSLRAEDTAVYYCARQDGYRYAMDYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC | 32 |

| Identity | Sequence | SEQ ID NO: |
|---|---|---|
| | LVKGFYPSDIAVEWESNGQPENNYKTTPPVLDSDGSFFLYS KLTVDKSRWQQGNVFSCSVMHEALHNHYTQKSLSLSPGK | |
| Antibody B (Heavy Chain, IgG1) | EVQLVESGGGLVKPGGSLRLSCAASGFTFSDYGMHWVRQAP GKGLEWVAYISSGNRITYYADTVKGRFTISRDNAKNSLYLQ MNSLRAEDTAVYYCARQDGYRYAMDYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPGK | 33 |
| Antibody B (Heavy Chain, IgG4 DM) | EVQLVESGGGLVKPGGSLRLSCAASGFTFSDYGMHWVRQAP GKGLEWVAYISSGNRITYYADTVKGRFTISRDNAKNSLYLQ MNSLRAEDTAVYYCARQDGYRYAMDYWGQGTLVTVSSASTK GPSVFPLAPCSRSTSESTAALGCLVKDYFPEPVTVSWNSGA LTSGVHTFPAVLQSSGLYSLSSVVTVPSSSLGTKTYTCNVD HKPSNTKVDKRVESKYGPPCPPCPAPEFEGGPSVFLFPPKP KDTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLTCLVK GFYPSDIAVEWESNGQPENNYKTTPPVLDSDGSFFLYSRLT VDKSRWQEGNVFSCSVMHEALHNHYTQKSLSLSLGK | 34 |
| Antibody B (Heavy Chain, IgG1KOb) | EVQLVESGGGLVKPGGSLRLSCAASGFTESDYGMHWVRQAP GKGLEWVAYISSGNRITYYADTVKGRFTISRDNAKNSLYLQ MNSLRAEDTAVYYCARQDGYRYAMDYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAKGQPREPQVYTLPPSRDELTKNQVSLTC LVKGFYPSDIAVEWESNGQPENNYKTTPPVLDSDGSFFLYS KLTVDKSRWQQGNVFSCSVMHEALHNHYTQKSLSLSPGK | 35 |
| Antibody C (Light Chain) | DIQMTQSPSSLSASVGDRVTITCSASSSVSYMLWFQ QKPGKAPKLLIYSTSNLASGVPSRFSGSGSGTDFTL TISSLQPEDFATYYCQQRTFYPYTFGGGTKVEIKRTVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC | 36 |
| Antibody C (Heavy Chain, IgG1KO) | QVQLVQSGAEVKKPGASVKVSCTASGFNIKDYYVHWVKQAP GQGLEWMGRIDPEDGDSKYAPKFQGKATMTADTSTSTVYME LSSLRSEDTAVYYCTTSYYVGTYGYWGQGTLVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPEAAGGPSVFLFPP KPKDTLMISRTPEVTCVVVDVSHEDPEVKFNWYVDGVEVHN AKTKPREEQYNSTYRVVSVLTVLHQDWLNGKEYKCKVSNKA LPAPIEKTISKAKGQPREPQVYTLPPSREEMTKNQVSLTCL VKGFYPSDIAVEWESNGQPENNYKTTPPVLDSDGSFFLYSK LTVDKSRWQQGNVFSCSVMHEALHNHYTQKSLSLSPGK | 37 |
| Antibody C (Heavy Chain, IgG1) | QVQLVQSGAEVKKPGASVKVSCTASGFNIKDYYVHWVKQAP GQGLEWMGRIDPEDGDSKYAPKFQGKATMTADTSTSTVYME LSSLRSEDTAVYYCTTSYYVGTYGYWGQGTLVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPSVFLFPP KPKDTLMISRTPEVTCVVVDVSHEDPEVKFNWYVDGVEVHN AKTKPREEQYNSTYRVVSVLTVLHQDWLNGKEYKCKVSNKA LPAPIEKTISKAKGQPREPQVYTLPPSREEMTKNQVSLTCL VKGFYPSDIAVEWESNGQPENNYKTTPPVLDSDGSFFLYSK LTVDKSRWQQGNVFSCSVMHEALHNHYTQKSLSLSPGK | 38 |
| Antibody C (Heavy Chain, IgG4 DM) | QVQLVQSGAEVKKPGASVKVSCTASGFNIKDYYVHWVKQAP GQGLEWMGRIDPEDGDSKYAPKFQGKATMTADTSTSTVYME LSSLRSEDTAVYYCTTSYYVGTYGYWGQGTLVTVSSASTKG PSVFPLAPCSRSTSESTAALGCLVKDYFPEPVTVSWNSGAL TSGVHTFPAVLQSSGLYSLSSVVTVPSSSLGTKTYTCNVDH KPSNTKVDKRVESKYGPPCPPCPAPEFEGGPSVFLFPPKPK DTLMISRTPEVTCVVVDVSQEDPEVQFNWYVDGVEVHNAKT | 39 |

-continued

| Identity | Sequence | SEQ ID NO: |
|---|---|---|
| | KPREEQFNSTYRVVSVLTVLHQDWLNGKEYKCKVSNKGLPS<br>SIEKTISKAKGQPREPQVYTLPPSQEEMTKNQVSLTCLVKG<br>FYPSDIAVEWESNGQPENNYKTTPPVLDSDGSFFLYSRLTV<br>DKSRWQEGNVFSCSVMHEALHNHYTQKSLSLSLGK | |
| Antibody C (Heavy Chain, IgG1KOb) | QVQLVQSGAEVKKPGASVKVSCTASGFNIKDYYVHWVKQAP<br>GQGLEWMGRIDPEDGDSKYAPKFQGKATMTADTSTSTVYME<br>LSSLRSEDTAVYYCTTSYYVGTYGYWGQGTLVTVSSASTKG<br>PSVFPLAPSSKSTSGGTAALGCLVKDYFPEPVTVSWNSGAL<br>TSGVHTFPAVLQSSGLYSLSSVVTVPSSSLGTQTYICNVNH<br>KPSNTKVDKRVEPKSCDKTHTCPPCPAPEAAGGPSVFLFPP<br>KPKDTLMISRTPEVTCVVVDVSHEDPEVKFNWYVDGVEVHN<br>AKTKPREEQYNSTYRVVSVLTVLHQDWLNGKEYKCKVSNKA<br>LPAPIEKTISKAKGQPREPQVYTLPPSRDELTKNQVSLTCL<br>VKGFYPSDIAVEWESNGQPENNYKTTPPVLDSDGSFFLYSK<br>LTVDKSRWQQGNVFSCSVMHEALHNHYTQKSLSLSPGK | 40 |

The variable regions were subcloned into one or two different suitable IgG expression vectors:

A) a human IgG1-KO (knock-out)/kappa format with a Leu234Ala, Leu235Ala double mutation in the Fc region to reduce effector function such as FcγR and complement binding B) a human IgG4-DM (double mutant)/kappa format with a Ser228Pro mutation in the hinge region to reduce the occurrence of IgG4 half-molecules and a Leu235Glu mutation to further reduce FcγR binding The two candidates Antibody A and Antibody B were purified and evaluated by the following criteria:
Appearance of CCF (turbidity)
Filtration properties of CCF
Yield on rProteinA
Turbidity upon elution and neutralization
Soluble aggregates (SEC)
Purity/contamination pattern (SDS)
Charge pattern (IEF)

Example 2

In Vitro Data

Antibody A, Antibody B and Antibody C were characterized along with antibodies 4D11 (Kirin/Astellas) and PG-102 (PanGenetics) which were produced based on published sequences. Data for Antibody A, Antibody B, Antibody C and 4D11 are shown below. PG-102 displayed agonistic activity and only incomplete inhibition of B cell proliferation (not shown). Table 2.2. summarizes the data obtained. A more detailed description of the data follows the Table 2.2.

TABLE 2.2

Summary of in vitro data of Antibody A, Antibody B and Antibody C and Kirin's 4D11 anti-CD40 antibody.

| Parameter/Assay | Antibody A | Antibody B | Antibody C | 4D11 |
|---|---|---|---|---|
| Kd +/− hu. Serum | <100 pM | <100 pM | <100 pM | <100 pM |
| Cell binding (EC50/nM ± SD | 1.2 (±0.28) | 1.5 (±0.68) | 1.7 (±0.28) | 0.9 (±0.3) |
| B cell proliferation:Antagonism (IC50/nM ± SD) | 0.3 (±0.13) | 0.2 (±0.10) | 0.1 (±0.004) | 0.03 (±0.02) |
| B cell proliferation:Agonism (SI*) (IC50/nM ± SD) | No Agonism (SI < 2) | No Agonism (SI < 2) | No Agonism (SI < 2) | No Agonism (SI < 2) |
| Dendritic cells/IL-12/23p40 Antagonism (IC50/nM ± SD) | <1 nM | <1 nM | <1 nM | <1 nM |
| Dendritic cells/IL-12/23p40 Agonism | No agonism | No agonism | No agonism | No agonism |
| Species cross-react.:Hu/Cyno Binding (EC50 ratios**) | 3 | 2 | 1 | Not tested |

Figure 1B:
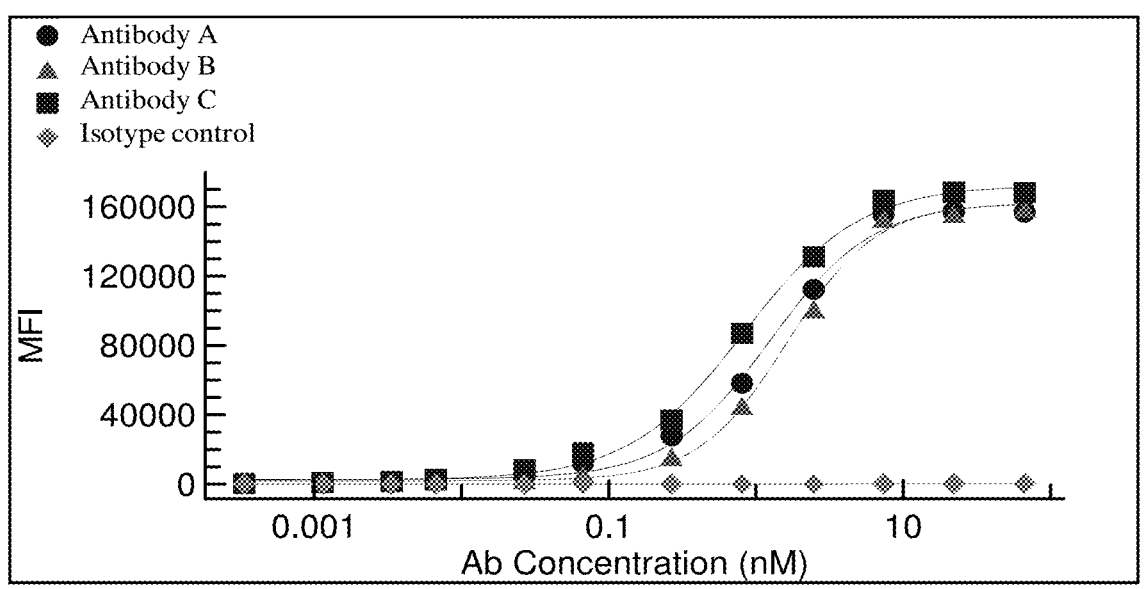
Figure 2:
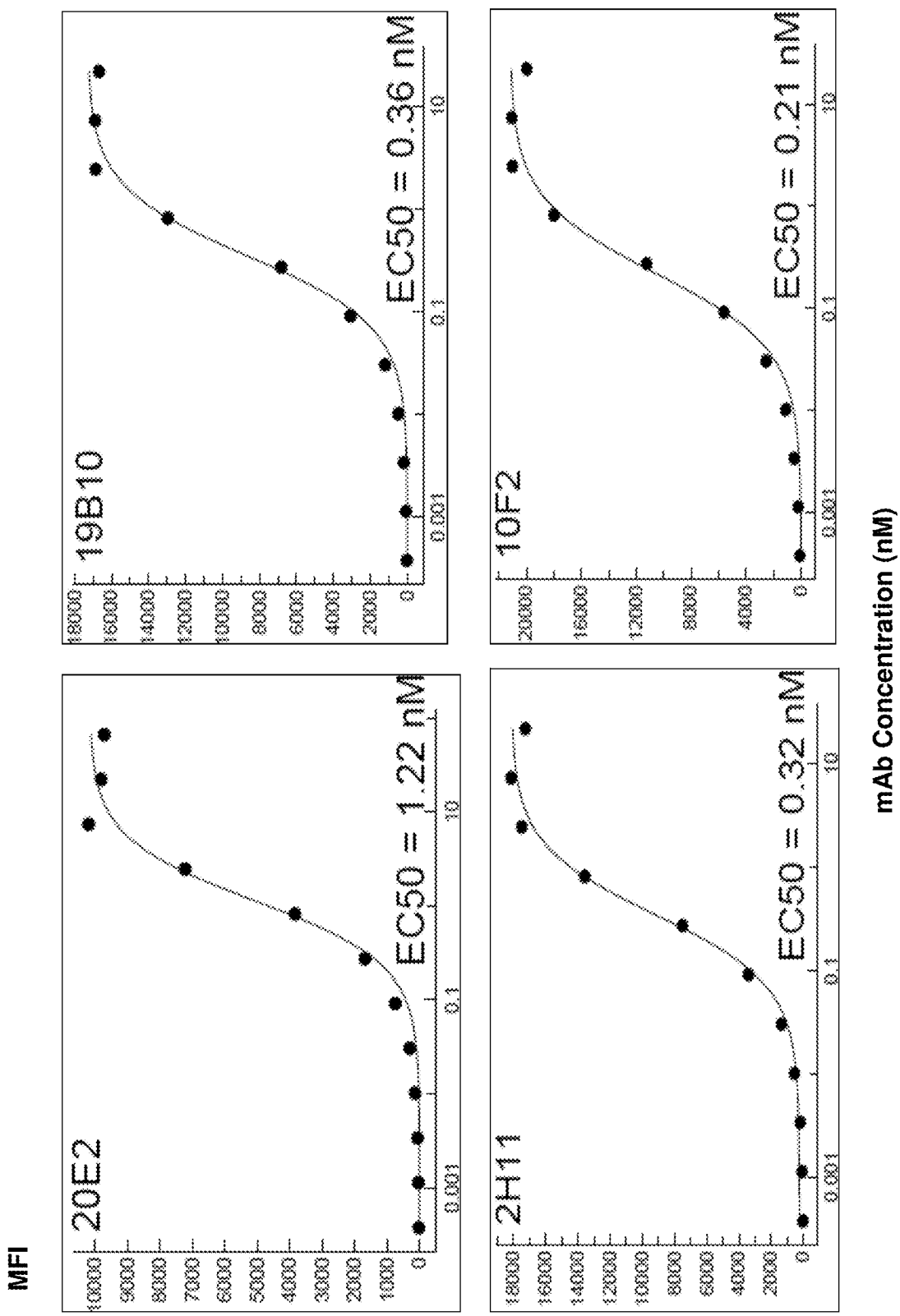
FIG. 2: Binding curves and corresponding EC50 values of humanized antibodies on RAMOS cells measured by flow cytometry. Representative data for one experiment is shown.

*SI, Stimulation Index;
**Ratio > 1 means increased binding to Cyno compared to Human A. Binding of Humanized Antibodies to Cellular CD40 and Recombinant CD40 Protein The specific binding of humanized antibodies to cellular CD40 was analyzed by flow cytometry using human CD40-transfected HEK293 cells. Concentration-dependent binding of Antibody A, Antibody B, and Antibody C was observed. The antibodies displayed a similar binding profile shown in FIG. 1B. EC50 values of the antibodies of the present invention and and Kirin's antibody 4D11 are all in the same range of ~1 nM which is most likely at the sensitivity limit of the assay due to the high levels of CD40 in the transfected cells. The specific binding of humanized antibodies to cellular CD40 on human Ramos cells also demonstrated concentration-dependent binding. The antibodies displayed a slightly different binding profiles (shown in FIG. 2) and EC50 values between 0.21-1.22 nM. No binding was detected on CD40 negative cells such as non-transfected HEK293 cells or the T cell line HSB-2 thus confirming selective binding to CD40 (data not shown).

The affinity of Antibody A, Antibody B and Antibody C binding to human CD40-Fc protein was measured via ForteBio Octet and revealed dissociation constants ($K_D$) of <100 pM. Due to antibody and CD40-Fc bivalency avidity effects prevent Kds below 100 pM from being determined accurately. In addition, the binding to CD40-Fc was analyzed in the absence and presence of 50% human serum and no significant effect of serum on binding was observed (data not shown)

B. Activity of Humanized Antibodies in B Cell Activation/Proliferation Assays

The activity of humanized antibodies was tested in a B cell proliferation assay in which human B cells derived from peripheral blood are stimulated with recombinant CD40L in the presence of IL-2 and IL-4. Antibody A, Antibody B and Antibody C showed potent inhibition of the proliferation of B cells (shown in FIGS. 3A and 3B). Comparison to inhibition curves and IC50 values of BI's antibodies and Kirin's antibody 4D11, indicates the 4D11 antibody to have higher potency (FIGS. 3B and 4) when tested across multiple donors. When tested for agonistic activity in the absence of CD40L, antibodies, Antibody B Antibody A and Antibody C did not induce any B cell proliferation above background levels at concentrations up to 10 µg/ml (67 nM) (shown in FIG. 4) similar to the 4D11 antibody.

The competitor antibody 4D11 appeared to be slightly more potent with an average IC50 of ~0.02 nM and absence of agonistic effects. Data for the three BI antibodies and 4D11 are summarized in FIG. 4 and Table 2.2 above. Another competitor antibody, PG-102 (derived from clone 5D12), also tested in this assay, displayed significant agonist effects stimulating B cell proliferation in the absence of CD40L (FIG. 4). Therefore, the lack of agonistic activity of our lead candidates clearly differentiates them from PG-102.

Figure 5:
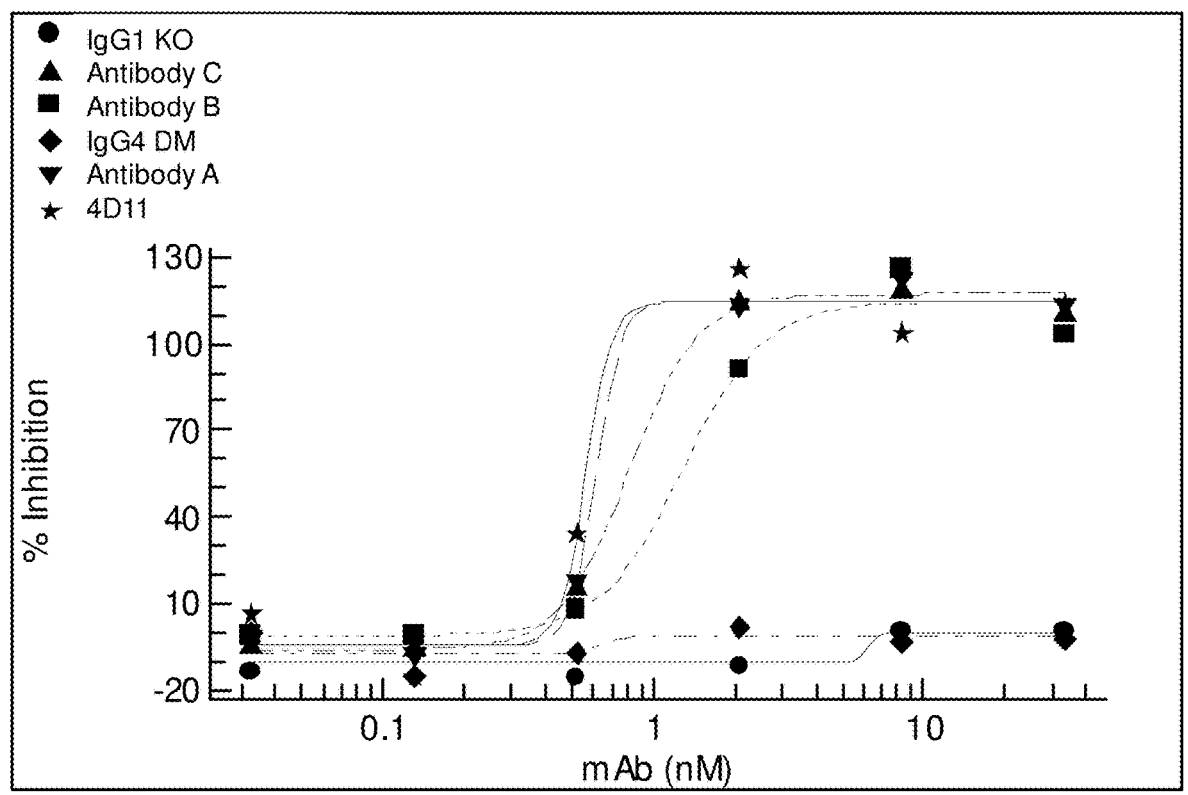
FIG. 5: Testing of Antibody B, Antibody A and Antibody C for inhibition of CD40 induced CD86-up-regulation of human whole blood assays. The 4D11 anti-CD40 antibody is shown for comparison. The IgG1 isotype control showed no effects in this assay. Representative data for one donor is shown.

In a second assay the antibodies were assessed for inhibition of CD86 up-regulation in human B cells. In this instance, the assay can be performed with human whole blood or in purified B cells, both in the presence of exogenous CD40L. In agreement with the B cell proliferation data, Antibody B Antibody A and Antibody C tested in human whole blood showed potent inhibition of CD40-mediated CD86 up-regulation as measured by flow cytometry (shown in FIG. 5). Antibody C displayed similar potency to 4D11 in this assay while the potency of Antibody B and Antibody A were somewhat weaker. Comparison of Antibody B and 4D11 on purified B cells or in whole blood, shows that the potency of Antibody B (IC50 and IC90 values) are relatively unchanged for purified B cells compared to B cells in the presence of other CD40 bearing cells or serum, while 4D11 undergoes a dramatic shift in potency in the whole blood conditions (shown in FIG. 6).

Figures 6, 7:
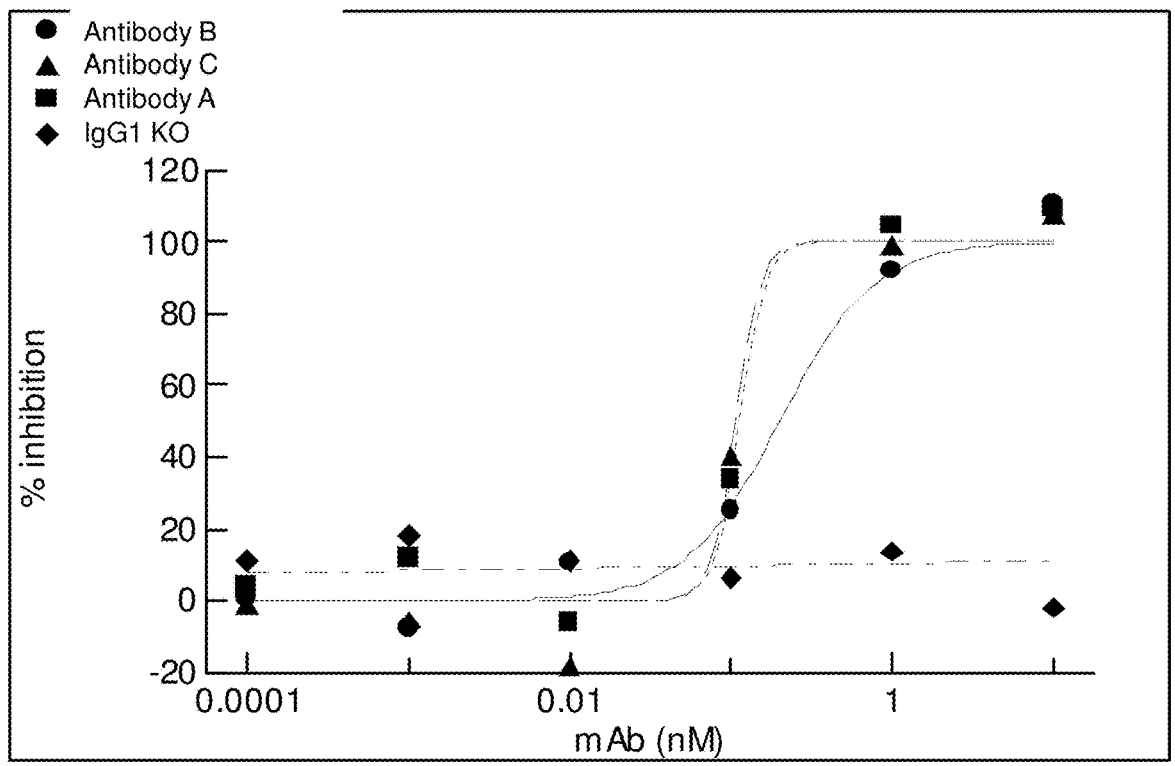
FIG. 6: Summary of the results of testing of Antibody B for inhibition of CD40 induced CD86-up-regulation on human purified B cells and human whole blood. The data at both the (A) IC50 and (B) IC90 points are depicted. The IgG1 isotype control showed no effects in either assay. Data for multiple donors (n=4-5) are summarized in the table
FIG. 7: Testing of Antibody B, Antibody A and Antibody C for inhibition of CD40 induced CD86 up-regulation in cynomolgus monkey whole blood assays. The IgG1 isotype control showed no effect in this assay. Representative data for one donor is shown.

Similar data has been developed when Antibody B Antibody A and Antibody C were assessed for inhibition of CD86 up-regulation on cynomolgus monkey B cells when performed with whole blood samples (shown in FIG. 7). Antibody B Antibody A and Antibody C tested in cynomolgus monkey whole blood showed potent inhibition of CD40-mediated CD86 up-regulation as measured by flow cytometry. These antibodies therefore all show functional cross-reactivity to cynomolgus monkey CD40 with similar potency to human CD40.

Figure 13:
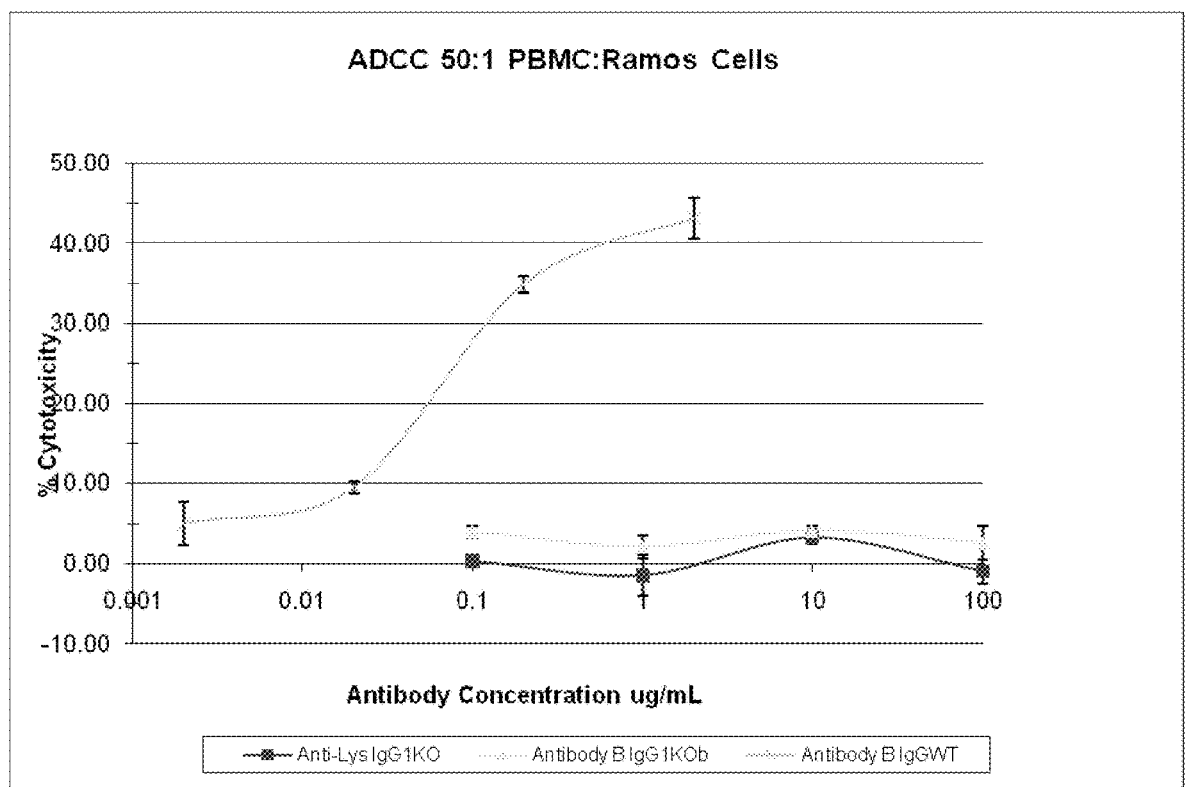
FIG. 13: ADCC activity with wild-type and knock-out IgG1 constructs

The activity of Antibody B IgG1KOb and Antibody B IgG1WT were assessed for ability to mediate antibody-dependent cellular cytotoxicity (FIG. 13). In this assay RAMOS cells were incubated with human PBMCs at an effector to target cell ratio of 50:1. Antibody B IgG1KOb and Antibody B IgG1WT were titrated from 20 ug/ml and the extent of cell death is monitored by release of LDH. The data shown are from one representative experiment. The data show that Antibody A IgG1Wt 20E2-12-RIgG1WT is an effective mediator of ADCC and that Antibody B IgG1KOb containing the mutations eliminating effector function does not have ADCC activity.

Example 3

Pharmacokinetic/Pharmacodynamic Studies

A. Single dose IV Administration of Antibody A and Antibody B at 1 or 10 mg/kg in Cynomolgus Monkeys Antibody A and Antibody B were each dosed at 1 and 10 mg/kg IV to male, cynomolgus monkeys (N=3)/dose. Blood samples were collected from 0-504 hr (3 weeks), serum was recovered, and samples were stored at −20° C. until analysis. The samples were analyzed by sandwich ELISA as described above. The serum concentration-time profiles of both antibodies in monkeys after both IV doses and the pharmacokinetic parameters are summarized in FIG. 8 and Tables 2.7.1 (Antibody A) and 2.7.2 (Antibody B) shown below. Both antibodies showed dose-dependent pharmacokinetics suggesting that at low dose, clearance is predominantly attributable to consistent with target-mediated disposition whereas at higher dose the antibody is cleared primarily by catabolism. Similar dose-dependent pharmacokinetic profiles have been observed for other MAbs targeting membrane-associated targets (e.g. CD19, CD20, EGFR, CD146 and HER2). Clearance for Antibody A was 0.8 and 0.1 mL/h/kg for the 1 and 10 mg/kg doses, respectively. Clearance for Antibody B was 0.7 and 0.1 mL/hr/kg for the 1 and 10 mg/kg doses, respectively. Similarly, Antibody A half-life was 1 and 13 days for the 1 and 10 mg/kg doses, respectively and Antibody B half-life was 2 and 13 days for the same respective doses. Although Antibody B had a marginally longer half-life at the lower dose relative to the same dose for Antibody A, this difference would not be expected to translate into more sustained exposure upon chronic administration. AUC for both compounds was supraproportional and volume of distribution (Vss) for both compounds approximated that of plasma volume (~40 mL/kg) exhibiting the limited tissue distribution typically seen for large, polar protein therapeutics. Overall, there were no appreciable differences in pharmacokinetic parameters between the two antibodies.

TABLE 2.7.1

Pharmacokinetic parameters of Antibody A in male, cynomolgus monkeys (N = 3)/dose after single 1 and 10 mg/kg IV doses.

| Dose (mg/kg) | CLp (mL/hr/kg) | Vss (mL/kg) | AUC (µM · hr) | T½ (days) | MRT (days) |
|---|---|---|---|---|---|
| 1 | 0.8 ± 0.03 | 41 ± 6 | 8.0 ± 0.3 | 0.9 ± 0.2 | 2.1 ± 0.2 |
| 10 | 0.10 ± 0.02 | 42 ± 6 | 660 ± 92 | 12.6 ± 0.5 | 17.5 ± 0.3 |

TABLE 2.7.2

Pharmacokinetic parameters of Antibody B in male, cynomolgus monkeys (N = 3)/dose after single 1 and 10 mg/kg IV doses.

| Dose (mg/kg) | CLp (mL/hr/kg) | Vss (mL/kg) | AUC (µM · hr) | T½ (days) | MRT (days) |
|---|---|---|---|---|---|
| 1 | 0.7 ± 0.16 | 40 ± 2 | 10.1 ± 2.7 | 1.5 ± 0.2 | 2.6 ± 0.8 |
| 10 | 0.09 ± 0.01 | 41 ± 6 | 744 ± 55 | 13.3 ± 3.0 | 19.3 ± 4.2 |

B. Ex Vivo Pharmacodynamic Study

As part of the PK study described above we analyzed the pharmacodynamic effects of anti-CD40 antibodies. To this end whole blood samples were incubated with recombinant CD40L overnight and the increase of CD86 expression on B cells was determined by flow cytometry. Samples were analyzed at day 0 (pre-treatment), day 2, 7 and 14 after dosing. Although the increase in CD86 expression is relatively small (~5-20-%) a dose-dependent effect was observed (shown in FIGS. 9A and 9B). In the group of animals dosed with 10 mg/kg of Antibody A and Antibody B, the CD86 induction was completely inhibited at 2, 7 and 14 days consistent with the sustained exposure at this dose. Animals dosed with 1 mg/kg showed complete inhibition at day 2, partial inhibition at day 7 and no inhibition at day 14. The loss of the pharmacodynamic effect over time correlates with the faster clearance of the antibody in the low dose group.

Example 4

Toxicology Related Studies: CD40 on Platelets

CD40 is constitutively expressed on human platelets (Henn, et al., 2001) and (Inwald, et al., 2003), while CD40L is rapidly and transiently expressed on the cell surface of activated platelets (Henn, et al., 2001). While anti-CD40 antibodies without FcγR binding would not be expected to have effects on platelets, it is important to directly demonstrate that this is the case. Flow cytometry studies were performed to demonstrate the binding of anti-CD40 lead candidates to human and cynomolgus platelets.

Previously it has been demonstrated by flow cytometry that the G28.5 and mAb 89 anti-CD40 mAb bind to resting human platelets (Henn, et al., 2001). This was confirmed using FITC-labeled G28.5 antibody. 5-fold serial dilutions of G28.5 were prepared and a range of 0.5 µg/ml to 0.32 ng/ml was incubated in a 100 µl of platelets obtained from humans (2 donors) or cynomolgus monkeys (3 donors) for 30 minutes at room temperature. In addition, APC-labeled anti-CD45 mAb was used to identify platelets bound to other $CD40^+$ cell types so as to exclude these cells from analysis. After antibody staining, the platelets were washed and fixed with Optilyse C and flow cytometry was performed. The mean fluorescence intensity (MFI) was determined as a measure of antibody binding to $CD45^-$ platelets.

Commercially available 5c3 and selected antibodies of the invention anti-CD40 mouse mAb were FITC-labeled. Binding to Ramos cells was confirmed. The number of FITC molecules per antibody molecule ranged from 2 to 4 FITC per antibody molecule. Five-fold serial dilutions of commercial and candidate annti-CD40 mAb were prepared ranging from 0.5 µg/ml to 0.32 ng/ml and incubated with human (3 donors) and cynomolgus (2 donors) platelet for 30 minutes at room temperature.

Figures 11, 12:
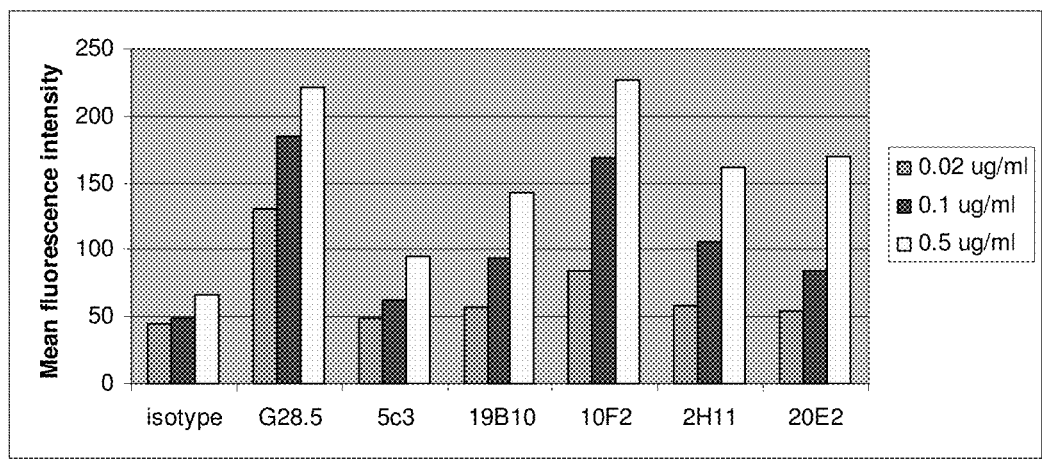
FIG. 11: Binding of various mouse anti-human CD40 antibodies to human platelets.
FIG. 12: Summary of the results of the binding comparison of Antibody B to the anti-CD40 mAb 4D11 on human B cells and platelets in whole blood

A representative graph demonstrating the binding of the mouse candidate anti-CD40 mAb to human platelets is shown in FIG. 11. The four candidate monoclonal antibodies displayed specific binding to human platelets compared to the FITC-labeled isotype control antibody. 10F2, 2H11, 19B10 and 20E2 demonstrated comparable binding to platelets. A similar trend was observed for cynomolgus platelets (data not shown).

In addition to these studies, directly labeled Antibody B and 4D11 were compared for the ability to bind platelets and B cells in human and cynomolgus monkey whole blood samples (shown in FIG. 12). 4D11 displayed similar binding (as exemplified by EC50) to both B cells and platelets in the human and cynomolgus monkey blood samples. Antibody B showed a similar pattern but with much weaker binding potency.

Example 5

In Vivo Pharmacology Studies in the NSG Mouse Model

The efficacy of the humanized antibodieis, Antibody A, was evaluated in an antibody production model where human PBMC's were injected into immunodeficient NSG mice in order to generate a graft vs. host response. Significant production of human IgM (hIgM) and IgG (hIgG) can be detected beginning 2 weeks following engraftment. Treatment with Antibody A at doses of 5 and 1 mg/kg significantly inhibited the hIgG and hIgM response at weeks 2 and 3 following engraftment. A comparator antibody (4D11) was evaluated at a single 5 mg/kg dose and also demonstrated abrogation of the response. In a second study all antibodies Antibody A, Antibody B and Antibody C were tested at a single dose of 1 mg/kg and showed complete inhibition of the IgM and IgG response at week 2 (FIG. 10).

Example 6

Biomarker Analysis

Figure 9B:
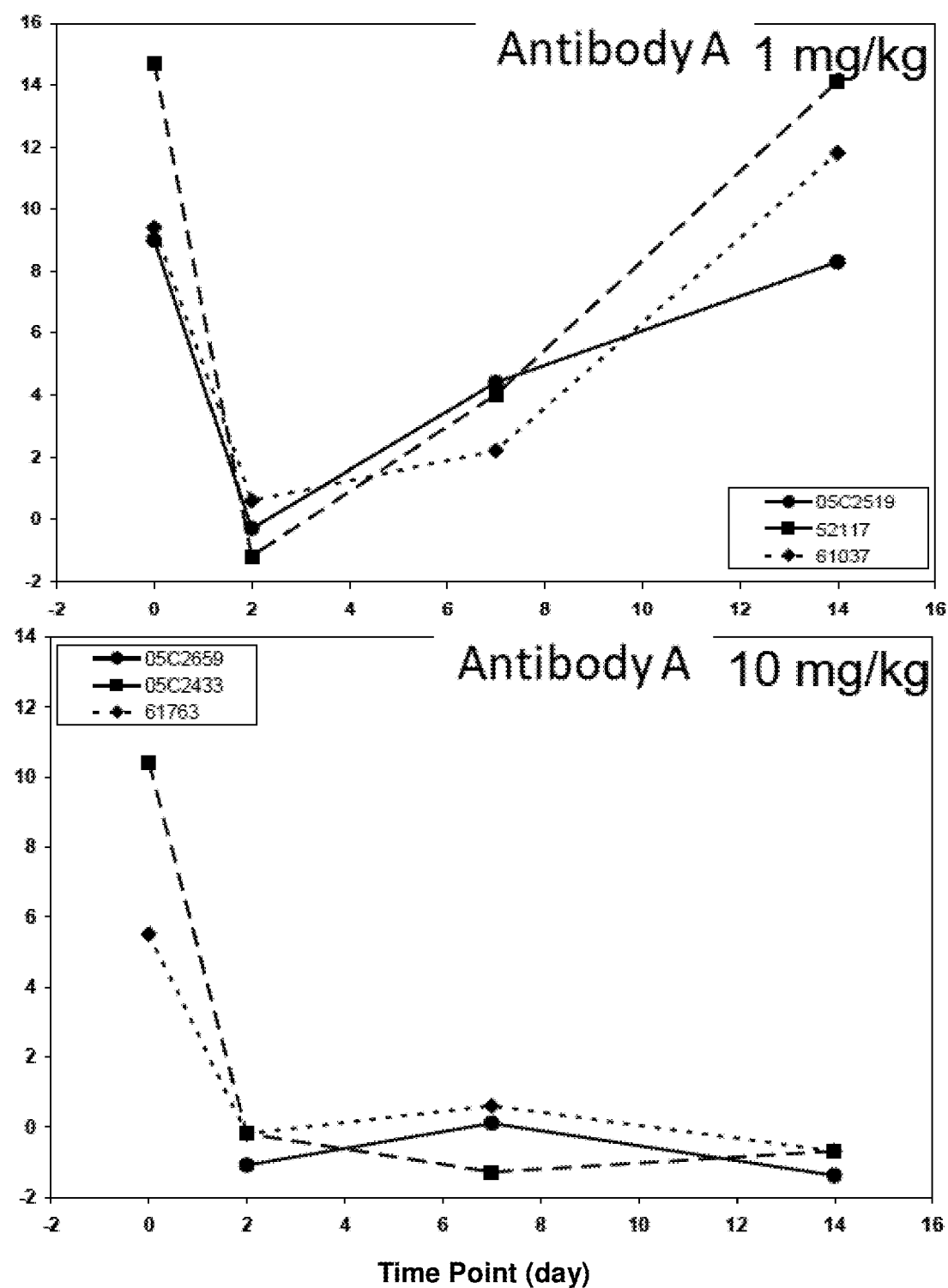

Receptor up-regulation: CD40L-induced up-regulation of receptors can be measured by flow cytometry. Human whole blood can be stimulated with optimized concentration of soluble CD40L and the full percentage of CD20+Receptor+ cells can be measured by flow cytometry. The change in percentage of CD86 expression on CD20 positive cells was measured in parallel to the cyanomologous pk study assessing Antibodies A and B (FIGS. 9A and 9B). The data shows inhibition of CD86 up regulation at time points consistent with the exposure of the antibodies.

Targeted proteomics: The increased secretion of proteins upon CD40 stimulation in whole blood can be used as potential biomarker(s). An optimized concentration of soluble CD40L and stimulation time were established using Luminex multiplex beads platform detecting MDC/CCL22 and several other secreted proteins. Clinical samples will be assessed from human whole blood in full dose range of anti-CD40 mAb.

Receptor occupancy: CD40 receptor occupancy can be determined in an in vitro or ex vivo assay based on flow cytometric analysis of B cells in human whole blood. Current candidates Antibody of the instant in invention and non-competing anti-CD40 antibody 5C3 will be used to quantitate receptor occupancy assay.

Example 7

Anti-Tumor Activity of Humanized Anti-CD40 Antibody

In some instances it may be desirable to determine the antitumor properties of the antibodies of the present invention. Such a determination may be made by assaying the antitumor activity of the humanized anti-CD40 antibody in a SCID mouse lymphoma xenograft model. Such a SCID model can be injected with cancer cells to present a tumor, e.g., $5 \times 10^6$ million tumor cells can be injected subcutaneously into SCID mice (10/group) thirteen days prior to starting drug treatment. Murine anti-CD40 antibodies of the present invention or an comparison (e.g., control or other humanized antibody) is given intra-peritoneally 3 times per week (4 mg/kg/dose) with 8 or 5 doses administered. The development and growth of tumors are monitored in the mouse and tumor volume may be measured weekly during the selected study period, e.g., 14-day study period. Preferably the results will show a 2, 3, 4, 5, 6, 7, 8, 9, 10 or more fold increase in the growth of tumors in control mice as compared to the mice treated with the antibodies of the present invention. Preferably, over the treatment period, tumor growth in mice treated with the antibodies of the invention will be negligible. Such data can corroborate that the humanized antibody being tested is effective in suppressing tumor growth in this B lymphoma xenograph model.

Example 8

Prolonged Survival by Humanized Anti-CD40 Antibody

The efficacy of the humanized anti-CD40 antibody on survival of tumor-bearing mice such as those described above can be assayed in a SCID mouse lymphoma xenograph model. SCID mice (10/group) are inoculated intravenously with $1 \times 10^6$ million tumor cells three days prior to antibody treatment. Mice are then treated with the murine or humanized anti-CD40 antibodies of the present invention or an Ig control, adminstered intraperitoneally two times per week (4 mg/kg/dose) for a total of five doses. The mouse cages can then be examined daily for mortality to determine the level of efficacy of the antibodies in prolonging survival of a subject having cancer.

Various references, including patent applications, patents, and scientific publications, are cited herein, the disclosures of which are incorporated herein by reference in their entireties. Citation or identification of any reference herein shall not be construed as an admission that such reference is available as prior art to the present invention.

Preferred aspects of the present invention may be described according the embodiments in the following paragraphs:

Paragraph 1. A humanized monoclonal antibody wherein said antibody specifically binds to human CD40 having an antagonistic activity IC50 of less than 1 nM and has no agonism up to 100 µg/ml in B cell proliferation and wherein said antibody is further characterized in that the antibody has an in vivo half life in non-human primates that is at least 10 days.

Paragraph 2. The humanized monoclonal antibody of Paragraph 1 wherein said antibody has a half-life in cynomolgus monkeys of greater than 8 days at a dose of less than 30 mg/kg.

Paragraph 3. The antibody of Paragraph 1, wherein the antibody comprises a heavy chain sequence selected from the group consisting of any of SEQ ID NO:1 to SEQ ID NO:4 and a light chain sequence selected from the group consisting of any of SEQ ID NO:5 to SEQ ID NO:8.

Paragraph 4. The antibody of Paragraph 1, wherein said antibody is a humanized antibody or antigen binding fragment of an antibody having the heavy chain variable region amino acid sequence of any of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, SEQ ID NO: 40, SEQ ID NO: 42, SEQ ID NO: 44, SEQ ID NO: 46, SEQ ID NO: 48, SEQ ID NO. 50 SEQ ID NO: 53, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

Paragraph 5. The antibody of Paragraph 1, wherein said antibody is a humanized antibody or antigen binding fragment of an antibody that comprises a light chain variable domain amino acid sequence of SEQ ID NO: 5 to SEQ ID NO:8, SEQ ID NO:26, SEQ ID NO:31, SEQ ID NO:36, SEQ ID NO:41, SEQ ID NO:43, SEQ ID NO:45, SEQ ID NO:47, SEQ ID NO:49, SEQ ID NO:50, SEQ ID NO:51, SEQ ID NO:52, SEQ ID NO:54, SEQ ID NO:55, SEQ ID NO:56, SEQ ID NO:74, SEQ ID NO:75, or SEQ ID NO:76.

Paragraph 6. The monoclonal antibody of Paragraph 1, wherein said antibody comprises a heavy chain and a light chain, wherein the heavy chain CDR1 sequence selected from the group consisting of SEQ ID NO: 9 through SEQ ID NO:11, a heavy chain CDR2 sequence selected from the group consisting of SEQ ID NO:12 through SEQ ID NO:15 and a heavy chain CDR3 sequence selected from the group consisting of SEQ ID NO:16 through SEQ ID NO:17; and wherein the light chain CDR1 sequence has a sequence selected from the group consisting of SEQ ID NO:18 through SEQ ID NO:21, a light chain CDR2 sequence of SEQ ID NO:22 through SEQ ID NO:23 and a light chain CDR3 sequence selected from the group consisting of SEQ ID NO:24 through SEQ ID NO:25.

Paragraph 7. The monoclonal antibody of Paragraph 1, wherein said antibody comprises a heavy chain CDR1 sequence of SEQ ID NO: 10, a heavy chain CDR2 sequence of SEQ ID NO:13 and a heavy chain CDR3 sequence of SEQ ID NO:16 and wherein said antibody comprises a light chain CDR1 sequence of SEQ ID NO:19, a light chain CDR2 sequence of SEQ ID NO:22 and a light chain CDR3 sequence of SEQ ID NO:24.

Paragraph 8. The monoclonal antibody of Paragraph 1, wherein said antibody comprises a heavy chain CDR1 sequence of SEQ ID NO: 9, a heavy chain CDR2 sequence of SEQ ID NO:14 and a heavy chain CDR3 sequence of SEQ ID NO:16 and wherein said antibody comprises a light chain CDR1 sequence of SEQ ID NO:20, a light chain CDR2 sequence of SEQ ID NO:22 and a light chain CDR3 sequence of SEQ ID NO:24.

Paragraph 9. An anti-CD40 antibody comprising a heavy chain variable domain sequence of any one of SEQ ID NOs:1 to 4.

Paragraph 10. An anti-CD40 antibody comprising an light chain variable domain sequence of any one of SEQ ID NOs: 5 to SEQ ID NO:8.

Paragraph 12. A humanized antibody or antibody fragment having a heavy chain variable domain and a light chain variable region comprising the amino acid sequences of SEQ ID NO:27 and SEQ ID NO:26, respectively; SEQ ID NO:28 and SEQ ID NO:26, respectively; SEQ ID NO:29 and SEQ ID NO:26, respectively; SEQ ID NO:30 and SEQ ID NO:26, respectively; SEQ ID NO:32 and SEQ ID NO:31, respectively; SEQ ID NO:33 and SEQ ID NO:31, respectively; SEQ ID NO:34 and SEQ ID NO:31, respectively; SEQ ID NO:35 and SEQ ID NO:31, respectively; SEQ ID NO:37 and SEQ ID NO:36, respectively; SEQ ID NO:38 and SEQ ID NO:36, respectively; SEQ ID NO:39 and SEQ ID NO:36, respectively; SEQ ID NO:40 and SEQ ID NO: 36, respectively.

Paragraph 13. An isolated antibody or antigen-binding fragment that specifically binds to human CD40, comprising a humanized heavy chain variable domain comprising a framework region having an amino acid sequence at least 90% identical to the amino acid sequence of the framework region of the human variable domain heavy chain amino acid sequence of SEQ ID NO: 27, SEQ ID NO:28, SEQ ID NO:29 or SEQ ID NO:30, and comprising a light chain amino acid sequence at least 90% identical to a corresponding light chain variable domain of SEQ ID NO:26.

Paragraph 14. An isolated antibody or antigen-binding fragment that specifically binds to human CD40, comprising a humanized heavy chain variable domain comprising a framework region having an amino acid sequence at least 90% identical to the amino acid sequence of the framework region of the human variable domain heavy chain amino acid sequence of SEQ ID NO:32, SEQ ID NO:33, SEQ ID NO:34 or SEQ ID NO:35, and comprising a light chain amino acid sequence at least 90% identical to a corresponding light chain variable of SEQ ID NO:31.

Paragraph 15. An isolated antibody or antigen-binding fragment that specifically binds to human CD40, comprising a humanized heavy chain variable domain comprising a framework region having an amino acid sequence at least 90% identical to the amino acid sequence of the framework region of the human variable domain heavy chain amino acid sequence of SEQ ID NO: 37, SEQ ID NO:38; SEQ ID NO:39 or SEQ ID NO: 40, and comprising a light chain amino acid sequence at least 90% identical to a corresponding light chain of SEQ ID NO:36.

Paragraph 16. The antibody of Paragraph 1, wherein said antibodies fail to stimulate production of cytokines from B cells in that absence of CD40L.

Paragraph 17. The antibody of Paragraph 1, wherein said antibodies bind to human CD40 in the presence of 50% human serum with a reduction of on rate less than two fold.

Paragraph 18. The antibody of Paragraph 1, wherein said antibody produces inhibition of IgM and IgG production in a mammal at a concentration of 1 mg/kg.

Paragraph 19. A method of blocking the function of human CD40 in a mammal comprising administering to said mammal a composition comprising an antibody of Paragraph 1 in an amount sufficient to block a CD40 mediated immune response in said mammal.

Paragraph 20. A method of treating or ameliorating graft vs host disease in a mammal comprising administering to said mammal a composition comprising an antibody of Paragraph 1 in an amount sufficient to decrease one or more of the symptoms of graft vs. host disease in said animal.

Paragraph 21. The method of Paragraph 20, wherein said mammal has an autoimmune or inflammatory disease selected from the group consisting of rheumatoid arthritis, multiple sclerosis, proliferative lupus glomerulonephritis, inflammatory bowel disease (IBD), psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

Paragraph 22. The method of Paragraph 19, wherein said mammal has rheumatoid arthritis.

Paragraph 23. The method of Paragraph 20, further comprising administering a second therapeutic agent selected from the group consisting of a TNF-antagonist, a disease-modifying antirheumatic drug, a CTLA4-antagonist, an anti-IL-6 receptor mAb and an anti-CD20 mAb.

Paragraph 24. A method according to Paragraph 20, wherein said inflammatory disease or autoimmune disease is an inflammatory disease or autoimmune disease that is associated with cells expressing both CD40 and CD20.

Paragraph 25. The method of Paragraph 19, wherein said anti-CD40 antibody is administered by a parenteral route of administration.

Paragraph 26. The method of Paragraph 19, wherein said anti-CD40 antibody is administered intravenously or subcutaneously.

Paragraph 27. A method of inhibiting antibody production by B cells in a human patient comprising administering to said human patient an effective amount of an anti-CD40 antibody of Paragraph 1.

Paragraph 28. The method of Paragraph 27, wherein said human patient has an inflammatory disease or autoimmune disease that is associated with CD40-expressing cells.

Paragraph 29. The method of Paragraph 27, wherein said human patient is suffering from an autoimmune disease selected from the group consisting of autoimmune or inflammatory disease selected from the group consisting of rheumatoid arthritis, multiple sclerosis, proliferative lupus glomerulonephritis, inflammatory bowel disease (IBD), psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

Paragraph 30. A method for inhibiting the growth of cells expressing human CD40 antigen, comprising administering the antibody or antigen-binding fragment of Paragraph 1 to the cells, which antibody or antigen-binding fragment specifically binds to the human cell surface CD40 antigen, wherein the binding of the antibody or antigen-binding fragment to the CD40 antigen inhibits the growth or differentiation of the cells.

Paragraph 31. A method for treating a subject having a CD40-associated disorder, comprising administering to the subject the antibody or antigen-binding fragment of Paragraph 1, which antibody or antigen-binding fragment specifically binds to human CD40, wherein the binding of the antibody or antigen-binding fragment to CD40 inhibits the growth or differentiation of cells of the CD40-associated disorder.

Paragraph 32. The method of Paragraph 31, wherein the cells of the CD40-associated disorder are B lymphoblastoid cells, pancreatic, lung cells, breast cells, ovarian cells, colon cells, prostate cells, skin cells, head and neck cells, bladder cells, bone cells or kidney cells.

Paragraph 33. The method of Paragraph 31, wherein the CD40-associated disorder is chronic lymphocytic leukemia, Burkitt's lymphoma, multiple myeloma, a T cell lymphoma, Non-Hodgkin's Lymphoma, Hodgkin's Disease, Waldenstrom's macroglobulinemia or Kaposi's sarcoma.

Paragraph 34. A method for inducing depletion of peripheral B cells, comprising administering to the cells the antibody or antigen-binding fragment of Paragraph 1, which antibody or antigen-binding fragment specifically binds to a human cell surface CD40 antigen, wherein the binding of the antibody or antigen-binding fragment to the CD40 antigen induces depletion of the cells.

Paragraph 35. The method of Paragraph 34, wherein the antibody or antigen-binding fragment is administered to a subject having an immune disorder.

Paragraph 36. The method of Paragraph 34, wherein the immune disorder is rheumatoid arthritis or systemic lupus erythematosus.

Paragraph 37. A method of treating rheumatoid arthritis in a subject comprising administering to said subject an antibody of Paragraph 1, wherein said antibody is an antagonistic antibody that blocks the function of CD40 in said subject.

Paragraph 38. The method of Paragraph 37, wherein said antibody is administered in an amount effective to inhibit B cell differentiation and antibody isotype switching in said subject.

Paragraph 39. The method of Paragraph 37, wherein said antibody is administered in an amount effective to inhibit cytokine and chemokine production and up-regulation of adhesion molecules in T-cells and macrophages in said subject.

Paragraph 40. The method of Paragraph 37, wherein said antibody is administered in an amount effective to inhibit activation of dendritic cells in said subject.

Paragraph 41. The method of Paragraph 37, wherein said antibody is administered in an amount effective to inhibit production of proinflammatory cytokines, chemokines, matrix metalloproteinases, prostaglandins, and down-regulate adhesion molecules in non-immune cells in said subject.

Paragraph 42. The method of Paragraph 37, wherein said antibody is administered in combination with a regimen comprising methotrexate administration and/or administration of Enbrel/Humira.

Paragraph 43. The method of Paragraph 37, wherein said subject is a subject that has rheumatoid arthritis and has been non-responsive to methotrexate treatment alone.

Paragraph 44. The method of Paragraph 43, wherein said method comprises treating said subject with a regimen comprising methotrexate administration and/or administration of Enbrel/Humira.

Paragraph 45. The method of Paragraph 37, wherein treatment of said subject with said antagonistic anti-CD40 antibody has a superior efficacy to treatment with methotrexate alone, Enbrel alone, a combination of Enbrel+methotrexate.

Paragraph 46. The method of Paragraph 43, wherein treatment of said subject with said antagonistic anti-CD40 antibody has a superior efficacy to treatment with Enbrel+MTX in patients who have had an inadequate response to methotrexate.

Paragraph 47. The method of Paragraph 37, wherein said antibody is administered in combination with a regimen comprising an anti-TNF agent.

Paragraph 48. The method of Paragraph 37, wherein said subject is a subject that has rheumatoid arthritis and has been non-responsive to treatment with an anti-TNF agent alone.

Paragraph 49. The method of Paragraph 48 wherein said method comprises treating said subject with a regimen comprising treatment with an anti-TNF agent in combination with said antagonistic anti-CD40 antibody.

Paragraph 50. The method of Paragraph 37, wherein treatment of said subject with said antagonistic anti-CD40 antibody has a superior efficacy to treatment with an anti-TNF agent.

Paragraph 51. The method of Paragraph 48, wherein treatment of said subject with said antagonistic anti-CD40 antibody has a superior efficacy to treatment with Orencia or Rituxan in patients who have had an inadequate response to an anti-TNF agent alone.

Paragraph 52. A pharmaceutical composition comprising: (i) the antibody or antigen-binding fragment of Paragraph 8; and (ii) a pharmaceutically acceptable excipient.

Paragraph 53. A pharmaceutical composition of Paragraph 52 wherein said antibody or antigen binding fragment thereof is conjugated to a second agent.

Paragraph 54. The pharmaceutical composition of Paragraph 52 wherein said second agent is a cytotoxic agent, a PEG-carrier, an enzyme or a marker.

Paragraph 55. An isolated polynucleotide encoding a heavy chain variable region amino acid sequence of any of SEQ ID NO: 1 to 4, SEQ ID NO:27, SEQ ID NO:28, SEQ ID NO: 29, SEQ ID NO:30, SEQ ID NO:32, SEQ ID NO:33, SEQ ID NO:34, SEQ ID NO:35, SEQ ID NO:37, SEQ ID NO:38, SEQ ID NO:39, SEQ ID NO: 40, SEQ ID NO: 42, SEQ ID NO: 44, SEQ ID NO: 46, SEQ ID NO: 48, SEQ ID. NO. 50, SEQ ID NO: 53, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73.

Paragraph 56. An isolated polynucleotide encoding a light chain variable region amino acid sequence of any of SEQ ID NO: 5 to SEQ ID NO:8, SEQ ID NO:26, SEQ ID NO:31, SEQ ID NO:36, SEQ ID NO:41, SEQ ID NO:43, SEQ ID NO:45, SEQ ID NO:47, SEQ ID NO:49, SEQ ID NO:50, SEQ ID NO:51, SEQ ID NO:52, SEQ ID NO:54, SEQ ID NO:55, SEQ ID NO:56, SEQ ID NO:74, SEQ ID NO:75, or SEQ ID NO:76.

Paragraph 57. A use of an antibody of Paragraph 1 in the manufacture of a medicament for blocking the function of human CD40 in a mammal wherein the medicament blocks a CD40 mediated immune response in said mammal.

Paragraph 58. A use of an antibody of Paragraph 1 for the manufacture of a medicament for treating or ameliorating graft vs host disease in a mammal.

Paragraph 59. The use of Paragraph 58, wherein said medicament is manufactured for the treatment of an autoimmune or inflammatory disease selected from the group consisting of rheumatoid arthritis, multiple sclerosis, proliferative lupus glomerulonephritis, inflammatory bowel disease (IBD), psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

Paragraph 60. A use according to Paragraph 58 wherein said medicament further comprises a second therapeutic agent selected from the group consisting of a TNF-antagonist, a disease-modifying antirheumatic drug, a CTLA4-antagonist, an anti-IL-6 receptor mAb and an anti-CD20 mAb.

Paragraph 61. A use according to Paragraph 57 wherein said medicament is manufactured for use a parenteral route of administration.

Paragraph 62. A use according to Paragraph 57 wherein said medicament is manufactured for use intravenously or subcutaneously.

Paragraph 63. A use of an antibody of Paragraph 1 in the manufacture of a medicament for the inhibition of antibody production by B cells in a human patient.

Paragraph 64. A use of an antibody of Paragraph 1 for the manufacture of a medicament for inhibiting the growth and/or differentiation of cells expressing human CD40 antigen.

Paragraph 65. A use of an antibody of Paragraph 1 for the manufacture of a medicament for the treatment of a subject having a CD40-associated disorder wherein the binding of the antibody or antigen-binding fragment in said medicament to CD40 inhibits the growth or differentiation of cells of the CD40-associated disorder.

Paragraph 66. A use according to Paragraph 65, wherein the medicament is used for the treatment of cells of a CD40-associated disorder selected from B lymphoblastoid cells, pancreatic, lung cells, breast cells, ovarian cells, colon cells, prostate cells, skin cells, head and neck cells, bladder cells, bone cells or kidney cells.

Paragraph 67. The use according of Paragraph 65, wherein the medicament is used for the treatment of chronic lymphocytic leukemia, Burkitt's lymphoma, multiple myeloma, a T cell lymphoma, Non-Hodgkin's Lymphoma, Hodgkin's Disease, Waldenstrom's macroglobulinemia or Kaposi's sarcoma.

Paragraph 68. A use of an antibody of Paragraph 1 in the manufacture of a medicament for inducing depletion of peripheral B cells wherein the antibody or antigen-binding fragment of the medicament specifically binds to a human cell surface CD40 antigen, wherein the binding of the antibody or antigen-binding fragment to the CD40 antigen induces depletion of the cells.

Paragraph 69. The use according to Paragraph 68, wherein the medicament is for the treatment of a subject having an immune disorder.

Paragraph 70. The use according to Paragraph 68, wherein the medicament is for the treatment of rheumatoid arthritis or systemic lupus erythematosus.

Paragraph 71. A use of an antibody of Paragraph 1 for the manufacture of a medicament for the treatment of rheumatoid arthritis in a subject.

Paragraph 72. The use according to Paragraph 71, wherein the medicament is for the inhibition of B cell differentiation and antibody isotype switching in said subject.

Paragraph 73. The use according to Paragraph 71, wherein the medicament is for the inhibition of cytokine and chemokine production and up-regulation of adhesion molecules in T-cells and macrophages in said subject.

Paragraph 74. The use according to Paragraph 71 wherein the medicament is for the inhibition of activation of dendritic cells in said subject.

Paragraph 75. The use according to Paragraph 71 wherein the medicament is for the inhibition of production of proinflammatory cytokines, chemokines, matrix metalloproteinases, prostaglandins, and down-regulation of adhesion molecules in non-immune cells in said subject.

Paragraph 76. The use according to Paragraph 71, wherein the medicament is a combination medicament to be administered in combination with a regimen comprising methotrexate administration and/or administration of Enbrel/Humira.

Paragraph 77. The use according to Paragraph 71, wherein the medicament further comprises an anti-TNF agent.

The application of the teachings disclosed herein is not to be limited in scope by the specific embodiments described herein. Indeed, various modifications will be within the capabilities of one having ordinary skill in the art in light of the teachings contained herein and accompanying examples. Such modifications are intended to fall within the scope of the appended claims.

What is claimed is:

1. An isolated antibody or antigen-binding fragment that specifically binds to human CD40, comprising:
a humanized heavy chain variable domain comprising a heavy chain CDR1 comprising SEQ ID NO: 11 or a variant thereof comprising one amino acid substitution, a heavy chain CDR2 comprising SEQ ID NO: 15 or a variant thereof comprising one to three amino acid substitutions, a heavy chain CDR3 comprising SEQ ID NO: 17 or a variant thereof comprising consecutive amino acids glycine (G) and tyrosine (Y) of SEQ ID NO: 17, and comprising a light chain variable domain comprising a light chain CDR1 comprising SEQ ID NO: 21 or a variant thereof comprising one amino acid substitution, a light chain CDR2 comprising SEQ ID NO: 23 or a variant thereof comprising one amino acid substitution, and a light chain CDR3 comprising SEQ ID NO: 25.

2. A humanized monoclonal antibody or antigen-binding fragment of an antibody comprising a heavy chain CDR1 comprising SEQ ID NO: 11 or a variant thereof comprising one amino acid substitution, a heavy chain CDR2 comprising SEQ ID NO: 15 or a variant thereof comprising one to three amino acid substitutions, a heavy chain CDR3 comprising SEQ ID NO: 17 or a variant thereof comprising consecutive amino acids glycine (G) and tyrosine (Y) of SEQ ID NO: 17, a light chain CDR1 comprising SEQ ID NO: 21 or a variant thereof comprising one amino acid substitution, a light chain CDR2 comprising SEQ ID NO: 23 or a variant thereof comprising one amino acid substitution, and a light chain CDR3 comprising SEQ ID NO: 25;
wherein said antibody or antigen binding fragment of the antibody specifically binds to human CD40 having an antagonistic activity IC50 of less than 1 nM and has no agonism up to 100 μg/ml in B cell proliferation.

3. A method of blocking the function of human CD40 in a mammal comprising administering to said mammal a composition comprising an antibody of claim 1 in an amount sufficient to block a CD40 mediated immune response in said mammal.

4. The method of claim 3, wherein the mammal is a human subject with a disease or disorder selected from the group consisting of: graft versus host disease and autoimmune or inflammatory disease.

5. The method of claim 4, wherein the autoimmune or inflammatory disease is selected from the group consisting of rheumatoid arthritis, multiple sclerosis, proliferative lupus glomerulonephritis, inflammatory bowel disease (IBD), ulcerative colitis, psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

6. The method of claim 3, wherein said antibody is administered by a parenteral route, intravenous route or subcutaneous route of administration.

7. A pharmaceutical composition comprising: (i) the antibody of claim 1; and (ii) a pharmaceutically acceptable excipient.

8. A humanized monoclonal antibody or antigen binding fragment comprising
(i) a heavy chain domain comprising SEQ ID NO:27, SEQ ID NO:28, SEQ ID NO:29, SEQ ID NO:30, or a variant thereof, and a light chain domain comprising SEQ ID NO: 26 or a variant thereof comprising up to 7 amino acid substitutions; or
(ii) a heavy chain domain comprising SEQ ID NO:32, SEQ ID NO:33, SEQ ID NO:34, SEQ ID NO:35, or a variant thereof, and a light chain domain comprising SEQ ID NO: 31 or a variant thereof comprising up to 7 amino acid substitutions; or
(iii) a heavy chain domain comprising SEQ ID NO:37, SEQ ID NO:38, SEQ ID NO:39, SEQ ID NO:40, or a variant thereof, and a light chain domain comprising SEQ ID NO:36 or a variant thereof comprising up to 7 amino acid substitutions.

9. A humanized monoclonal antibody or antigen binding fragment comprising:
(i) a heavy chain variable domain comprising any one of SEQ ID NOs: 1 and 57-60, and a light chain variable domain comprising any one of SEQ ID NOs: 5, 54, 55, and 56; or
(ii) a heavy chain variable domain comprising any one of SEQ ID NOs: 2 and 67-73, and a light chain variable domain comprising any one of SEQ ID NOs: 6 and 74-76; or (iii) a heavy chain variable domain comprising any one of SEQ ID NOs: 3 and 62-66, and a light chain variable domain comprising any one of SEQ ID NOs: 7, 54, 55, and 56; or (iv) a heavy chain variable domain comprising any one of SEQ ID NOs: 4, 42, 44, 46, 48, 50, and 53 or a variant thereof, and a light chain variable domain comprising any one of SEQ ID NOs: 8, 41, 43, 45, 47, 49, 51, and 52 or a variant thereof comprising up to 7 amino acid substitutions.

10. The antibody or antigen binding fragment of claim 8, wherein the antibody or antigen binding fragment of the antibody specifically binds to human CD40; has an antagonistic activity IC50 of less than 1 nM; or has no agonism up to 100 µg/ml in B cell proliferation.

11. The antibody or antigen binding fragment of claim 8, wherein the antibody or antigen binding fragment of the antibody has an in vivo half-life in non-human primates that is at least 10 days or has a half-life in cynomolgus monkeys of greater than 8 days at a dose of less than 30 mg/kg.

12. The antibody or antigen binding fragment of claim 8, wherein the antibody or antigen binding fragment does not stimulate production of cytokines from B cells in the absence of CD40L.

13. The antibody or antigen binding fragment of claim 8, wherein the antibody or antigen binding fragment inhibits production of cytokines from B cells in the absence of CD40L.

14. The antibody or antigen binding fragment of claim 8, wherein the antibody or antigen binding fragment binds to human CD40 in the presence of 50% human serum with a reduction of on rate less than two fold.

15. A method of blocking the function of human CD40 in a mammal comprising administering to said mammal a composition comprising an antibody according to claim 8 in an amount sufficient to block a CD40 mediated immune response in said mammal.

16. The method of claim 15, wherein the mammal is a human subject with a disease or disorder selected from the group consisting of: graft versus host disease and autoimmune or inflammatory disease.

17. The method of claim 16, wherein the autoimmune or inflammatory disease is selected from the group consisting of lupus nephritis, rheumatoid arthritis, multiple sclerosis, proliferative lupus glomerulonephritis, inflammatory bowel disease (IBD), ulcerative colitis, psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

18. An isolated antibody or antigen-binding fragment that specifically binds to human CD40, comprising a humanized heavy chain variable domain comprising SEQ ID NO: 37, SEQ ID NO:38; SEQ ID NO:39, SEQ ID NO: 40, or a variant thereof comprising up to 7 amino acid substitutions, and comprising a light chain sequence of SEQ ID NO:36 or a variant thereof comprising up to 7 amino acid substitutions.

19. The method of claim 5, wherein the autoimmune or inflammatory disease is ulcerative colitis.

20. A method of blocking the function of human CD40 in a mammal comprising administering to said mammal a composition comprising an antibody of claim 2 in an amount sufficient to block a CD40 mediated immune response in said mammal.

21. The method of claim 20, wherein the mammal is a human subject with a disease or disorder selected from the group consisting of: graft versus host disease and autoimmune or inflammatory disease.

22. The method of claim 21, wherein the autoimmune or inflammatory disease is selected from the group consisting of rheumatoid arthritis, multiple sclerosis, proliferative lupus glomerulonephritis, inflammatory bowel disease (IBD), ulcerative colitis, psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

23. The method of claim 22, wherein the autoimmune or inflammatory disease is ulcerative colitis.

24. The method of claim 20, wherein said antibody is administered by a parenteral route, intravenous route or subcutaneous route of administration.

25. A pharmaceutical composition comprising: (i) the antibody of claim 2; and (ii) a pharmaceutically acceptable excipient.

26. A humanized monoclonal antibody of claim 8, wherein the antibody comprises a heavy chain domain comprising SEQ ID NO:27, SEQ ID NO:28, SEQ ID NO:29, SEQ ID NO:30, or a variant thereof, and a light chain domain comprising SEQ ID NO: 26 or a variant thereof comprising up to 7 amino acid substitutions.

27. A humanized monoclonal antibody of claim 8, wherein the antibody comprises a heavy chain domain comprising SEQ ID NO:35 or a variant thereof, and a light chain domain comprising SEQ ID NO: 31 or a variant thereof comprising up to 7 amino acid substitutions.

28. A method of blocking the function of human CD40 in a mammal comprising administering to said mammal a composition comprising an antibody of claim 27 in an amount sufficient to block a CD40 mediated immune response in said mammal.

29. The method of claim 28, wherein the mammal is a human subject with a disease or disorder selected from the group consisting of: graft versus host disease and autoimmune or inflammatory disease.

30. The method of claim 29, wherein the autoimmune or inflammatory disease is selected from the group consisting of rheumatoid arthritis, multiple sclerosis, proliferative lupus glomerulonephritis, inflammatory bowel disease (IBD), ulcerative colitis, psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

31. The method of claim 30, wherein the autoimmune or inflammatory disease is ulcerative colitis.

32. A humanized monoclonal antibody of claim 8, wherein the antibody comprises a heavy chain domain comprising SEQ ID NO:37, SEQ ID NO:38, SEQ ID NO:39, SEQ ID NO:40, or a variant thereof, and a light chain domain comprising SEQ ID NO:36 or a variant thereof comprising up to 7 amino acid substitutions.

33. The humanized monoclonal antibody or antigen binding fragment according to claim 9, wherein the heavy chain variable domain comprises SEQ ID NO: 53 or a variant thereof, and the light chain variable domain comprises SEQ ID NO: 52 or a variant thereof comprising up to 7 amino acid substitutions.

34. The antibody or antigen binding fragment of claim 33, wherein the antibody or antigen binding fragment of the antibody specifically binds to human CD40; has an antagonistic activity IC50 of less than 1 nM; or has no agonism up to 100 μg/ml in B cell proliferation.

35. The antibody or antigen binding fragment of claim 33, wherein the antibody or antigen binding fragment of the antibody has an in vivo half-life in non-human primates that is at least 10 days or has a half-life in cynomolgus monkeys of greater than 8 days at a dose of less than 30 mg/kg.

36. The antibody or antigen binding fragment of claim 33, wherein the antibody or antigen binding fragment does not stimulate production of cytokines from B cells in the absence of CD40L.

37. The antibody or antigen binding fragment of claim 33, wherein the antibody or antigen binding fragment inhibits production of cytokines from B cells in the absence of CD40L.

38. The antibody or antigen binding fragment of claim 33, wherein the antibody or antigen binding fragment binds to human CD40 in the presence of 50% human serum with a reduction of on rate less than two fold.

39. A method of blocking the function of human CD40 in a mammal comprising administering to said mammal a composition comprising an antibody of claim 33 in an amount sufficient to block a CD40 mediated immune response in said mammal.

40. The method of claim 39, wherein the mammal is a human subject with a disease or disorder selected from the group consisting of: graft versus host disease and autoimmune or inflammatory disease.

41. The method of claim 40, wherein the autoimmune or inflammatory disease is selected from the group consisting of rheumatoid arthritis, multiple sclerosis, proliferative lupus glomerulonephritis, inflammatory bowel disease (IBD), ulcerative colitis, psoriasis, idiopathic thrombocytopenic purpura (ITP), Crohn's Disease and systemic lupus erythematosus (SLE), Hashimoto's thyroiditis, primary myxoedema, thyrotoxicosis/Graves disease, pernicious anaemia, autoimmune atrophic gastritis, autoimmune carditis, Addison's disease, premature menopause, type 1-diabetes mellitus, Good pasture's syndrome, myasthenia gravis, autoimmune haemolytic anaemia, idiopathic leucopenia, primary biliary cirrhosis, active chronic hepatitis (HBs Ag negative), cryptogenic cirrhosis, Sjogren's syndrome, dermatomyositis, scleroderma, mixed tissues connective disease, discoid lupus erythematosus, and systemic vasculitis.

42. The method of claim 41, wherein the autoimmune or inflammatory disease is ulcerative colitis.

43. The method of claim 17, wherein the autoimmune or inflammatory disease is ulcerative colitis.

\* \* \* \* \*

SEQUENCE LISTING

```
<160> NUMBER OF SEQ ID NOS: 78

<210> SEQ ID NO 1
<211> LENGTH: 118
<212> TYPE: PRT
<213> ORGANISM: Artificial Sequence
<220> FEATURE:
<223> OTHER INFORMATION: CD40 Murine Lead VH Sequence of 2H11

<400> SEQUENCE: 1

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Val His Trp Val Lys Gln Arg Pro Glu Lys Gly Leu Glu Trp Ile
        35                  40                  45

Gly Arg Ile Asp Pro Glu Asp Gly Asp Ser Lys Tyr Ala Pro Lys Phe
    50                  55                  60

Gln Gly Lys Ala Thr Met Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95
```

```
Thr Thr Ser Tyr Tyr Val Gly Thr Tyr Gly Tyr Trp Gly Gln Gly Thr
            100                 105                 110

Thr Leu Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: CD40 Murine Lead VH Sequence of 10F2

<400> SEQUENCE: 2

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Pro Glu Lys Gly Leu Glu Trp Ile
            35                  40                  45

Gly Arg Ile Asp Pro Glu Asp Gly Asp Thr Lys Tyr Asp Pro Lys Phe
    50                  55                  60

Gln Gly Lys Ala Thr Met Thr Ala Asp Thr Ser Asn Thr Ala Tyr
65                  70                  75                  80

Leu His Leu Ser Ser Leu Thr Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Thr Leu Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: CD40 Murine Lead VH Sequence of 19B10

<400> SEQUENCE: 3

Glu Val Gln Leu Gln Gln Ser Gly Ala Glu Leu Val Arg Pro Gly Ala
1               5                   10                  15

Ser Val Gln Leu Ser Cys Thr Ala Ser Gly Phe Asn Ile Lys Asp Tyr
            20                  25                  30

Tyr Val His Trp Val Lys Gln Arg Pro Glu Lys Gly Leu Glu Trp Ile
            35                  40                  45

Gly Arg Ile Asp Pro Glu Asp Gly Asp Thr Lys Phe Ala Pro Lys Phe
    50                  55                  60

Gln Gly Lys Ala Thr Met Thr Ala Asp Thr Ser Ser Asn Thr Val Tyr
65                  70                  75                  80

Leu His Leu Ser Ser Leu Thr Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Thr Leu Thr Val Ser Ser
        115

<210> SEQ ID NO 4
<211> LENGTH: 119
<212> TYPE: PRT
```

<213> ORGANISM: Artificial Sequence
<220> FEATURE:
<223> OTHER INFORMATION: CD40 Murine Lead VH Sequence of 20E2

<400> SEQUENCE: 4

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Leu Tyr Tyr Cys
                85                  90                  95

Ala Arg Gln Asp Gly Tyr Arg Tyr Ala Met Asp Tyr Trp Gly Gln Gly
            100                 105                 110

Thr Ser Val Thr Val Ser Ser
        115

<210> SEQ ID NO 5
<211> LENGTH: 106
<212> TYPE: PRT
<213> ORGANISM: Artificial Sequence
<220> FEATURE:
<223> OTHER INFORMATION: CD40 Murine Lead VK Sequence of 2H11

<400> SEQUENCE: 5

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

Leu Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Gly Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Thr Phe Tyr Pro Tyr Thr
                85                  90                  95

Phe Gly Gly Gly Thr Lys Leu Glu Ile Lys
            100                 105

<210> SEQ ID NO 6
<211> LENGTH: 106
<212> TYPE: PRT
<213> ORGANISM: Artificial Sequence
<220> FEATURE:
<223> OTHER INFORMATION: CD40 Murine Lead VK Sequence of 10F2

<400> SEQUENCE: 6

Gln Ile Val Leu Thr Gln Ser Pro Thr Ile Met Ser Ala Ser Pro Gly
1               5                   10                  15

Glu Lys Val Ile Ile Thr Cys Ser Ala Thr Ser Ser Val Ser Tyr Ile
            20                  25                  30

Leu Trp Phe Gln Gln Lys Pro Gly Thr Ser Pro Lys Leu Trp Ile Tyr
        35                  40                  45

```
Ser Thr Ser Asn Leu Ala Ser Gly Val Pro Ala Arg Phe Ser Gly Ser
        50                  55                  60

Gly Ser Gly Ala Ser Tyr Ser Leu Thr Ile Ser Arg Met Glu Ala Glu
 65                  70                  75                  80

Asp Ala Ala Thr Tyr Tyr Cys Gln Gln Arg Thr Phe Tyr Pro Tyr Thr
                 85                  90                  95

Phe Gly Gly Gly Thr Lys Leu Glu Ile Lys
            100                 105

<210> SEQ ID NO 7
<211> LENGTH: 106
<212> TYPE: PRT
<213> ORGANISM: Artificial Sequence
<220> FEATURE:
<223> OTHER INFORMATION: CD40 Murine Lead VK Sequence of 19B10

<400> SEQUENCE: 7

Gln Ile Val Leu Thr Gln Ser Pro Ala Ile Met Ser Ala Ser Pro Gly
 1               5                  10                  15

Glu Lys Val Thr Ile Thr Cys Ser Ala Ser Ser Val Ser Tyr Met
                 20                  25                  30

Leu Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Thr Phe Tyr Pro Tyr Thr
                 85                  90                  95

Phe Gly Gly Gly Thr Lys Leu Glu Ile Lys
            100                 105

<210> SEQ ID NO 8
<211> LENGTH: 113
<212> TYPE: PRT
<213> ORGANISM: Artificial Sequence
<220> FEATURE:
<223> OTHER INFORMATION: CD40 Murine Lead VK Sequence of 20E2

<400> SEQUENCE: 8

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp His Gln Gln Lys Pro Gly Gln
            35                  40                  45

Pro Pro Lys Leu Leu Ile Tyr Trp Thr Ser Thr Arg Glu Ser Gly Val
        50                  55                  60

Pro Asp Arg Phe Thr Gly Ser Gly Ser Gly Thr Asp Phe Thr Leu Thr
 65                  70                  75                  80

Ile Ser Asn Leu Gln Ala Glu Asp Leu Ala Val Tyr Tyr Cys Gln Asn
                 85                  90                  95

Asp Tyr Thr Tyr Pro Leu Thr Phe Gly Ala Gly Thr Lys Leu Glu Leu
            100                 105                 110

Lys

<210> SEQ ID NO 9
```

```
<211> LENGTH: 10
<212> TYPE: PRT
<213> ORGANISM: Artificial Sequence
<220> FEATURE:
<223> OTHER INFORMATION: CDR1 Heavy Chain of 2H11 and 19B10

<400> SEQUENCE: 9

Gly Phe Asn Ile Lys Asp Tyr Tyr Val His
1               5                   10

<210> SEQ ID NO 10
<211> LENGTH: 10
<212> TYPE: PRT
<213> ORGANISM: Artificial Sequence
<220> FEATURE:
<223> OTHER INFORMATION: CDR1 Heavy Chain of 10F2

<400> SEQUENCE: 10

Gly Phe Asn Ile Lys Asp Tyr Tyr Ile His
1               5                   10

<210> SEQ ID NO 11
<211> LENGTH: 10
<212> TYPE: PRT
<213> ORGANISM: Artificial Sequence
<220> FEATURE:
<223> OTHER INFORMATION: CDR1 Heavy Chain of 20E2

<400> SEQUENCE: 11

Gly Phe Thr Phe Ser Asp Tyr Gly Met His
1               5                   10

<210> SEQ ID NO 12
<211> LENGTH: 17
<212> TYPE: PRT
<213> ORGANISM: Artificial Sequence
<220> FEATURE:
<223> OTHER INFORMATION: CDR2 Heavy Chain of 2H11

<400> SEQUENCE: 12

Arg Ile Asp Pro Glu Asp Gly Asp Ser Lys Tyr Ala Pro Lys Phe Gln
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: CDR2 Heavy Chain of 10F2

<400> SEQUENCE: 13

Arg Ile Asp Pro Glu Asp Gly Asp Thr Lys Tyr Asp Pro Lys Phe Gln
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: CDR2 Heavy Chain of 19B10

<400> SEQUENCE: 14

Arg Ile Asp Pro Glu Asp Gly Asp Thr Lys Phe Ala Pro Lys Phe Gln
1               5                   10                  15
```

Gly

<210> SEQ ID NO 15
<211> LENGTH: 17
<212> TYPE: PRT
<213> ORGANISM: Artificial Sequence
<220> FEATURE:
<223> OTHER INFORMATION: CDR2 Heavy Chain of 20E2

<400> SEQUENCE: 15

```
Tyr Ile Ser Ser Gly Asn Arg Ile Ile Tyr Tyr Ala Asp Thr Val Lys
1               5                   10                  15

Gly
```

<210> SEQ ID NO 16
<211> LENGTH: 9
<212> TYPE: PRT
<213> ORGANISM: Artificial Sequence
<220> FEATURE:
<223> OTHER INFORMATION: CDR3 Heavy Chain of 2H11, 10F2 and 19B10

<400> SEQUENCE: 16

```
Ser Tyr Tyr Val Gly Thr Tyr Gly Tyr
1               5
```

<210> SEQ ID NO 17
<211> LENGTH: 10
<212> TYPE: PRT
<213> ORGANISM: Artificial Sequence
<220> FEATURE:
<223> OTHER INFORMATION: CDR3 Heavy Chain of 20E2

<400> SEQUENCE: 17

```
Gln Asp Gly Tyr Arg Tyr Ala Met Asp Tyr
1               5                   10
```

<210> SEQ ID NO 18
<211> LENGTH: 10
<212> TYPE: PRT
<213> ORGANISM: Artificial Sequence
<220> FEATURE:
<223> OTHER INFORMATION: CDR1 Light Chain of 2H11

<400> SEQUENCE: 18

```
Ser Ala Ser Ser Ser Val Ser Tyr Met Leu
1               5                   10
```

<210> SEQ ID NO 19
<211> LENGTH: 10
<212> TYPE: PRT
<213> ORGANISM: Artificial Sequence
<220> FEATURE:
<223> OTHER INFORMATION: CDR1 Light Chain of 10F2

<400> SEQUENCE: 19

```
Ser Ala Thr Ser Ser Val Ser Tyr Ile Leu
1               5                   10
```

<210> SEQ ID NO 20
<211> LENGTH: 10
<212> TYPE: PRT
<213> ORGANISM: Artificial Sequence
<220> FEATURE:
<223> OTHER INFORMATION: CDR1 Light Chain of 19B10

<400> SEQUENCE: 20

```
Ser Ala Ser Ser Ser Val Ser Tyr Met Leu
1               5                   10
```

<210> SEQ ID NO 21
<211> LENGTH: 17
<212> TYPE: PRT
<213> ORGANISM: Artificial Sequence
<220> FEATURE:
<223> OTHER INFORMATION: CDR1 Light Chain of 20E2

<400> SEQUENCE: 21

```
Lys Ser Ser Gln Ser Leu Leu Asn Ser Gly Asn Gln Lys Asn Tyr Leu
1               5                   10                  15

Thr
```

<210> SEQ ID NO 22
<211> LENGTH: 7
<212> TYPE: PRT
<213> ORGANISM: Artificial Sequence
<220> FEATURE:
<223> OTHER INFORMATION: CDR2 Light Chain of 2H11, 10F2 and 19B10

<400> SEQUENCE: 22

```
Ser Thr Ser Asn Leu Ala Ser
1               5
```

<210> SEQ ID NO 23
<211> LENGTH: 7
<212> TYPE: PRT
<213> ORGANISM: Artificial Sequence
<220> FEATURE:
<223> OTHER INFORMATION: CDR2 Light Chain of 20E2

<400> SEQUENCE: 23

```
Trp Thr Ser Thr Arg Glu Ser
1               5
```

<210> SEQ ID NO 24
<211> LENGTH: 9
<212> TYPE: PRT
<213> ORGANISM: Artificial Sequence
<220> FEATURE:
<223> OTHER INFORMATION: CDR3 Light Chain of 2H11, 10F2, and 19B10

<400> SEQUENCE: 24

```
Gln Gln Arg Thr Phe Tyr Pro Tyr Thr
1               5
```

<210> SEQ ID NO 25
<211> LENGTH: 9
<212> TYPE: PRT
<213> ORGANISM: Artificial Sequence
<220> FEATURE:
<223> OTHER INFORMATION: CDR3 Light Chain of 20E2

<400> SEQUENCE: 25

```
Gln Asn Asp Tyr Thr Tyr Pro Leu Thr
1               5
```

<210> SEQ ID NO 26
<211> LENGTH: 220
<212> TYPE: PRT
<213> ORGANISM: Artificial Sequence
<220> FEATURE:
<223> OTHER INFORMATION: Light Chain of Antibody A

<400> SEQUENCE: 26

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Leu Asn Ser
            20                  25                  30

Gly Asn Gln Lys Asn Tyr Leu Thr Trp His Gln Gln Lys Pro Gly Gln
        35                  40                  45

Pro Pro Lys Leu Leu Ile Tyr Trp Thr Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 27
<211> LENGTH: 449
<212> TYPE: PRT
<213> ORGANISM: Artificial Sequence
<220> FEATURE:
<223> OTHER INFORMATION: Heavy Chain IgG1K0 of Antibody A

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gln Asp Gly Tyr Arg Tyr Ala Met Asp Tyr Trp Ala Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 28
<211> LENGTH: 449
<212> TYPE: PRT
<213> ORGANISM: Artificial Sequence
<220> FEATURE:
<223> OTHER INFORMATION: Heavy Chain IgG1 of Antibody A

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
                35                  40                  45
```

```
Ala Tyr Ile Ser Ser Gly Asn Arg Ile Ile Tyr Tyr Ala Asp Thr Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gln Asp Gly Tyr Arg Tyr Ala Met Asp Tyr Trp Ala Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

-continued

<210> SEQ ID NO 29
<211> LENGTH: 446
<212> TYPE: PRT
<213> ORGANISM: Artificial Sequence
<220> FEATURE:
<223> OTHER INFORMATION: Heavy Chain IgG4DM of Antibody A

<400> SEQUENCE: 29

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gln Asp Gly Tyr Arg Tyr Ala Met Asp Tyr Trp Ala Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
            370                 375                 380
Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 30
<211> LENGTH: 449
<212> TYPE: PRT
<213> ORGANISM: Artificial Sequence
<220> FEATURE:
<223> OTHER INFORMATION: Heavy Chain IgG1K0b of Antibody A

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Tyr Ile Ser Ser Gly Asn Arg Ile Ile Tyr Tyr Ala Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gln Asp Gly Tyr Arg Tyr Ala Met Asp Tyr Trp Ala Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 31
<211> LENGTH: 220
<212> TYPE: PRT
<213> ORGANISM: Artificial Sequence
<220> FEATURE:
<223> OTHER INFORMATION: Light Chain of Antibody B

<400> SEQUENCE: 31

Asp Ile Val Met Thr Gln Ser Pro Asp Ser Leu Ala Val Ser Leu Gly
1               5                   10                  15

Glu Lys Val Thr Ile Asn Cys Lys Ser Ser Gln Ser Leu Leu Asn Ser
                20                  25                  30

Gly Asn Gln Lys Asn Tyr Leu Thr Trp His Gln Gln Lys Pro Gly Gln
                35                  40                  45

Pro Pro Lys Leu Leu Ile Tyr Trp Thr Ser Thr Arg Glu Ser Gly Val
                50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205
```

```
Ser Pro Val Thr Lys Ser Phe Asn Arg Gly Glu Cys
    210                 215                 220
```

<210> SEQ ID NO 32
<211> LENGTH: 449
<212> TYPE: PRT
<213> ORGANISM: Artificial Sequence
<220> FEATURE:
<223> OTHER INFORMATION: Heavy Chain IgG1K0 of Antibody B

<400> SEQUENCE: 32

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Tyr Arg Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

-continued

```
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 33
<211> LENGTH: 449
<212> TYPE: PRT
<213> ORGANISM: Artificial Sequence
<220> FEATURE:
<223> OTHER INFORMATION: Heavy Chain IgG1 of Antibody B

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Tyr Arg Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 34
<211> LENGTH: 446
<212> TYPE: PRT
<213> ORGANISM: Artificial Sequence
<220> FEATURE:
<223> OTHER INFORMATION: Heavy Chain IgG4DM of Antibody B

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Tyr Arg Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

-continued

```
                165                 170                 175
Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 35
<211> LENGTH: 449
<212> TYPE: PRT
<213> ORGANISM: Artificial Sequence
<220> FEATURE:
<223> OTHER INFORMATION: Heavy Chain IgG1K0b of Antibody B

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                    85                  90                  95
Ala Arg Gln Asp Gly Tyr Arg Tyr Ala Met Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys

<210> SEQ ID NO 36
<211> LENGTH: 213
<212> TYPE: PRT
<213> ORGANISM: Artificial Sequence
<220> FEATURE:
<223> OTHER INFORMATION: Light Chain of Antibody C

<400> SEQUENCE: 36
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Leu Trp Phe Gln Gln Lys Pro Gly Lys Ala Pro Lys Leu Leu Ile Tyr
            35                  40                  45

Ser Thr Ser Asn Leu Ala Ser Gly Val Pro Ser Arg Phe Ser Gly Ser
50                      55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Thr Phe Tyr Pro Tyr Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 37
<211> LENGTH: 448
<212> TYPE: PRT
<213> ORGANISM: Artificial Sequence
<220> FEATURE:
<223> OTHER INFORMATION: Heavy Chain IgG1K0 of Antibody C

<400> SEQUENCE: 37

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Tyr
            20                  25                  30

Tyr Val His Trp Val Lys Gln Ala Pro Gly Gln Gly Leu Glu Trp Met
            35                  40                  45

Gly Arg Ile Asp Pro Glu Asp Gly Asp Ser Lys Tyr Ala Pro Lys Phe
        50                  55                  60

Gln Gly Lys Ala Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 38
<211> LENGTH: 448
<212> TYPE: PRT
<213> ORGANISM: Artificial Sequence
<220> FEATURE:
<223> OTHER INFORMATION: Heavy Chain IgG1 of Antibody C

<400> SEQUENCE: 38

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Tyr
            20                  25                  30

Tyr Val His Trp Val Lys Gln Ala Pro Gly Gln Gly Leu Glu Trp Met
        35                  40                  45

Gly Arg Ile Asp Pro Glu Asp Gly Asp Ser Lys Tyr Ala Pro Lys Phe
    50                  55                  60
```

Gln Gly Lys Ala Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Thr Thr Ser Tyr Tyr Val Gly Thr Tyr Gly Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 39
<211> LENGTH: 445
<212> TYPE: PRT
<213> ORGANISM: Artificial Sequence
<220> FEATURE:

<223> OTHER INFORMATION: Heavy Chain IgG4DM of Antibody C

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Tyr
            20                  25                  30

Tyr Val His Trp Val Lys Gln Ala Pro Gly Gln Gly Leu Glu Trp Met
        35                  40                  45

Gly Arg Ile Asp Pro Glu Asp Gly Asp Ser Lys Tyr Ala Pro Lys Phe
    50                  55                  60

Gln Gly Lys Ala Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

```
Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 40
<211> LENGTH: 448
<212> TYPE: PRT
<213> ORGANISM: Artificial Sequence
<220> FEATURE:
<223> OTHER INFORMATION: Heavy Chain IgG1K0b of Antibody C

<400> SEQUENCE: 40

Gln Val Gln Leu Val Gln Ser Gly Ala Glu Val Lys Lys Pro Gly Ala
1               5                  10                  15

Ser Val Lys Val Ser Cys Thr Ala Ser Gly Phe Asn Ile Lys Asp Tyr
            20                  25                  30

Tyr Val His Trp Val Lys Gln Ala Pro Gly Gln Gly Leu Glu Trp Met
        35                  40                  45

Gly Arg Ile Asp Pro Glu Asp Gly Asp Ser Lys Tyr Ala Pro Lys Phe
    50                  55                  60

Gln Gly Lys Ala Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Gly Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 41
<211> LENGTH: 113
<212> TYPE: PRT
<213> ORGANISM: Artificial Sequence
<220> FEATURE:
<223> OTHER INFORMATION: Variable Light Chain in both BI 655034 and BI 655035

<400> SEQUENCE: 41

```
Asp Ile Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp His Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gly Gly Thr Lys Val Glu Ile
            100                 105                 110

Lys
```

<210> SEQ ID NO 42
<211> LENGTH: 119
<212> TYPE: PRT
<213> ORGANISM: Artificial Sequence
<220> FEATURE:
<223> OTHER INFORMATION: Variable Heavy Chain in both BI 655034 and BI 655035

<400> SEQUENCE: 42

```
Glu Val Gln Leu Val Lys Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
```

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gln Asp Gly Tyr Arg Tyr Ala Met Asp Tyr Trp Gly Gln Gly
                100                 105                 110

Thr Leu Val Thr Val Ser Ser
            115

<210> SEQ ID NO 43
<211> LENGTH: 113
<212> TYPE: PRT
<213> ORGANISM: Artificial Sequence
<220> FEATURE:
<223> OTHER INFORMATION: Variable Light Chain in both BI 655036 and
      Antibody A

<400> SEQUENCE: 43

Asp Ile Val Met Thr Gln Ser Pro Asp Ser Leu Ala Val Ser Leu Gly
 1               5                  10                  15

Glu Arg Ala Thr Met Ser Cys Lys Ser Ser Gln Ser Leu Leu Asn Ser
                20                  25                  30

Gly Asn Gln Lys Asn Tyr Leu Thr Trp His Gln Gln Lys Pro Gly Gln
            35                  40                  45

Pro Pro Lys Leu Leu Ile Tyr Trp Thr Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Thr Tyr Pro Leu Thr Phe Gly Gly Gly Thr Lys Val Glu Ile
                100                 105                 110

Lys

<210> SEQ ID NO 44
<211> LENGTH: 119
<212> TYPE: PRT
<213> ORGANISM: Artificial Sequence
<220> FEATURE:
<223> OTHER INFORMATION: Variable Heavy Chain in both BI 655036 and
      Antibody A

<400> SEQUENCE: 44

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Tyr Ile Ser Ser Gly Asn Arg Ile Ile Tyr Tyr Ala Asp Thr Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gln Asp Gly Tyr Arg Tyr Ala Met Asp Tyr Trp Ala Gln Gly
                100                 105                 110
```

Thr Leu Val Thr Val Ser Ser
         115

<210> SEQ ID NO 45
<211> LENGTH: 113
<212> TYPE: PRT
<213> ORGANISM: Artificial Sequence
<220> FEATURE:
<223> OTHER INFORMATION: Variable Light Chain in both BI 655038 and BI
      655039

<400> SEQUENCE: 45

Asp Ile Val Met Thr Gln Ser Pro Asp Ser Leu Ala Val Ser Leu Gly
1               5                   10                  15

Glu Lys Val Thr Met Asn Cys Lys Ser Gln Ser Leu Leu Asn Ser
            20                  25                  30

Gly Asn Gln Lys Asn Tyr Leu Thr Trp His Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Ala Gly Thr Lys Val Glu Ile
            100                 105                 110

Lys

<210> SEQ ID NO 46
<211> LENGTH: 119
<212> TYPE: PRT
<213> ORGANISM: Artificial Sequence
<220> FEATURE:
<223> OTHER INFORMATION: Variable Heavy Chain in both BI 655038 and BI
      655039

<400> SEQUENCE: 46

Glu Val Gln Leu Val Glu Ser Gly Gly Gly Leu Val Lys Pro Gly Gly
1               5                   10                  15

Ser Arg Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gln Asp Gly Tyr Arg Tyr Ala Met Asp Tyr Trp Gly Gln Gly
            100                 105                 110

Thr Leu Val Thr Val Ser Ser
        115

<210> SEQ ID NO 47
<211> LENGTH: 113
<212> TYPE: PRT
<213> ORGANISM: Artificial Sequence
<220> FEATURE:

<223> OTHER INFORMATION: Variable Light Chain in both BI 655040 and BI
      655041

<400> SEQUENCE: 47

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Asn Gln Lys Asn Tyr Leu Thr Trp His Gln Gln Lys Pro Gly Gln
        35                  40                  45

Pro Pro Lys Leu Leu Ile Tyr Trp Thr Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gly Gly Thr Lys Val Glu Ile
            100                 105                 110

Lys

<210> SEQ ID NO 48
<211> LENGTH: 119
<212> TYPE: PRT
<213> ORGANISM: Artificial Sequence
<220> FEATURE:
<223> OTHER INFORMATION: Variable Heavy Chain in both BI 655040 and BI
      655041

<400> SEQUENCE: 48

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gln Asp Gly Tyr Arg Tyr Ala Met Asp Tyr Trp Gly Gln Gly
            100                 105                 110

Thr Leu Val Thr Val Ser Ser
        115

<210> SEQ ID NO 49
<211> LENGTH: 113
<212> TYPE: PRT
<213> ORGANISM: Artificial Sequence
<220> FEATURE:
<223> OTHER INFORMATION: Variable Light Chain in both BI 655042 and BI
      655043

<400> SEQUENCE: 49

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Asn Gln Lys Asn Tyr Leu Thr Trp His Gln Gln Lys Pro Gly Gln
            35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Ala Gly Thr Lys Val Glu Ile
            100                 105                 110

Lys

<210> SEQ ID NO 50
<211> LENGTH: 119
<212> TYPE: PRT
<213> ORGANISM: Artificial Sequence
<220> FEATURE:
<223> OTHER INFORMATION: Variable Light Chain in both BI 655042 and BI
      655043

<400> SEQUENCE: 50

Glu Val Gln Leu Val Glu Ser Gly Gly Gly Leu Val Lys Pro Gly Gly
1               5                   10                  15

Ser Arg Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
            35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Tyr Arg Tyr Ala Met Asp Tyr Trp Gly Gln Gly
            100                 105                 110

Thr Leu Val Thr Val Ser Ser
        115

<210> SEQ ID NO 51
<211> LENGTH: 113
<212> TYPE: PRT
<213> ORGANISM: Artificial Sequence
<220> FEATURE:
<223> OTHER INFORMATION: Variable Light Chain in both BI 655044 and BI
      655045

<400> SEQUENCE: 51

Asp Ile Val Met Thr Gln Ser Pro Asp Ser Leu Ala Val Ser Leu Gly
1               5                   10                  15

Glu Lys Val Thr Met Asn Cys Lys Ser Ser Gln Ser Leu Leu Asn Ser
            20                  25                  30

Gly Asn Gln Lys Asn Tyr Leu Thr Trp His Gln Gln Lys Pro Gly Gln
            35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Leu Ala Val Tyr Tyr Cys Gln Asn
                85                  90                  95

Asp Tyr Thr Tyr Pro Leu Thr Phe Gly Ala Gly Thr Lys Val Glu Ile
            100                 105                 110

Lys

<210> SEQ ID NO 52
<211> LENGTH: 113
<212> TYPE: PRT
<213> ORGANISM: Artificial Sequence
<220> FEATURE:
<223> OTHER INFORMATION: Variable Light Chain in both BI 655046 and
      Antibody B

<400> SEQUENCE: 52

Asp Ile Val Met Thr Gln Ser Pro Asp Ser Leu Ala Val Ser Leu Gly
1               5                   10                  15

Glu Lys Val Thr Ile Asn Cys Lys Ser Ser Gln Ser Leu Leu Asn Ser
            20                  25                  30

Gly Asn Gln Lys Asn Tyr Leu Thr Trp His Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gly Gly Thr Lys Val Glu Ile
            100                 105                 110

Lys

<210> SEQ ID NO 53
<211> LENGTH: 119
<212> TYPE: PRT
<213> ORGANISM: Artificial Sequence
<220> FEATURE:
<223> OTHER INFORMATION: Variable Heavy Chain in each of BI 655044, BI
      655045, BI 655046 and Antibody B

<400> SEQUENCE: 53

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Asn Arg Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Tyr Arg Tyr Ala Met Asp Tyr Trp Gly Gln Gly
            100                 105                 110

Thr Leu Val Thr Val Ser Ser
        115

<210> SEQ ID NO 54
```

```
<211> LENGTH: 106
<212> TYPE: PRT
<213> ORGANISM: Artificial Sequence
<220> FEATURE:
<223> OTHER INFORMATION: Variable Light Chain in BI 655052

<400> SEQUENCE: 54

Gln Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Leu Trp Phe Gln Gln Lys Pro Gly Lys Ala Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Thr Phe Tyr Pro Tyr Thr
                85                  90                  95

Phe Gly Gly Gly Thr Lys Val Glu Ile Lys
            100                 105

<210> SEQ ID NO 55
<211> LENGTH: 106
<212> TYPE: PRT
<213> ORGANISM: Artificial Sequence
<220> FEATURE:
<223> OTHER INFORMATION: Variable Light Chain in each of BI 655053, BI
      655055, BI 655057, BI 655059 and BI 655061

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Leu Trp Phe Gln Gln Lys Pro Gly Lys Ala Pro Lys Leu Leu Ile Tyr
        35                  40                  45

Ser Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Thr Phe Tyr Pro Tyr Thr
                85                  90                  95

Phe Gly Gly Gly Thr Lys Val Glu Ile Lys
            100                 105

<210> SEQ ID NO 56
<211> LENGTH: 106
<212> TYPE: PRT
<213> ORGANISM: Artificial Sequence
<220> FEATURE:
<223> OTHER INFORMATION: Variable Light Chain in each of BI 655054,
      Antibody B, BI 655058, BI 655060 and BI 655062

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Leu Trp Phe Gln Gln Lys Pro Gly Lys Ala Pro Lys Leu Leu Ile Tyr
```

```
                35                  40                  45
Ser Thr Ser Asn Leu Ala Ser Gly Val Pro Ser Arg Phe Ser Gly Ser
         50                  55                  60
Gly Ser Gly Thr Asp Phe Thr Leu Thr Ile Ser Ser Leu Gln Pro Glu
 65                  70                  75                  80
Asp Phe Ala Thr Tyr Tyr Cys Gln Gln Arg Thr Phe Tyr Pro Tyr Thr
                 85                  90                  95
Phe Gly Gly Gly Thr Lys Val Glu Ile Lys
            100                 105

<210> SEQ ID NO 57
<211> LENGTH: 118
<212> TYPE: PRT
<213> ORGANISM: Artificial Sequence
<220> FEATURE:
<223> OTHER INFORMATION: Variable Heavy Chain in each of BI 655052, BI
      655053 and BI 655054

<400> SEQUENCE: 57

Gln Val Gln Leu Val Gln Ser Gly Ala Glu Val Lys Lys Pro Gly Ala
  1               5                  10                  15
Ser Val Lys Val Ser Cys Thr Ala Ser Gly Phe Asn Ile Thr Asp Tyr
             20                  25                  30
Tyr Val His Trp Val Lys Gln Arg Pro Gly Gln Gly Leu Glu Trp Met
         35                  40                  45
Gly Arg Ile Asp Pro Glu Asp Gly Asp Ser Lys Tyr Ala Pro Lys Phe
     50                  55                  60
Gln Gly Lys Ala Thr Met Thr Ala Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Thr Thr Ser Tyr Tyr Val Gly Thr Tyr Gly Tyr Trp Gly Gln Gly Thr
            100                 105                 110
Leu Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Variable Heavy Chain in both BI 655055 and
      Antibody C

<400> SEQUENCE: 58

Gln Val Gln Leu Val Gln Ser Gly Ala Glu Val Lys Lys Pro Gly Ala
  1               5                  10                  15
Ser Val Lys Val Ser Cys Thr Ala Ser Gly Phe Asn Ile Lys Asp Tyr
             20                  25                  30
Tyr Val His Trp Val Lys Gln Ala Pro Gly Gln Gly Leu Glu Trp Met
         35                  40                  45
Gly Arg Ile Asp Pro Glu Asp Gly Asp Ser Lys Tyr Ala Pro Lys Phe
     50                  55                  60
Gln Gly Lys Ala Thr Met Thr Ala Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Thr Thr Ser Tyr Tyr Val Gly Thr Tyr Gly Tyr Trp Gly Gln Gly Thr
```

-continued

```
                100                 105                 110
Leu Val Thr Val Ser Ser
        115

<210> SEQ ID NO 59
<211> LENGTH: 118
<212> TYPE: PRT
<213> ORGANISM: Artificial Sequence
<220> FEATURE:
<223> OTHER INFORMATION: Variable Heavy Chain in both BI 655057 and BI
      655058

<400> SEQUENCE: 59

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Thr Asp Tyr
            20                  25                  30

Tyr Val His Trp Val Lys Gln Arg Pro Gly Gln Gly Leu Glu Trp Met
        35                  40                  45

Gly Arg Ile Asp Pro Glu Asp Gly Asp Ser Lys Tyr Ala Pro Lys Phe
    50                  55                  60

Gln Gly Lys Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
                100                 105                 110

Leu Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Variable Heavy Chain in both BI 655059 and BI
      655060

<400> SEQUENCE: 60

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Tyr
            20                  25                  30

Tyr Val His Trp Val Lys Gln Ala Pro Gly Gln Gly Leu Glu Trp Ile
        35                  40                  45

Gly Arg Ile Asp Pro Glu Asp Gly Asp Ser Lys Tyr Ala Pro Lys Phe
    50                  55                  60

Gln Gly Lys Ala Thr Met Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
                100                 105                 110

Leu Val Thr Val Ser Ser
        115

<210> SEQ ID NO 61
<211> LENGTH: 118
<212> TYPE: PRT
```

<213> ORGANISM: Artificial Sequence
<220> FEATURE:
<223> OTHER INFORMATION: Variable Heavy Chain in both BI 655061 and BI
      655062

<400> SEQUENCE: 61

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Thr Asp Tyr
            20                  25                  30

Tyr Val His Trp Val Lys Gln Ala Pro Gly Gln Gly Leu Glu Trp Met
        35                  40                  45

Gly Arg Ile Asp Pro Glu Asp Gly Asp Ser Lys Tyr Ala Pro Lys Phe
    50                  55                  60

Gln Gly Lys Ala Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Gly Tyr Trp Gly Gln Gly Thr
            100                 105                 110

Leu Val Thr Val Ser Ser
        115

<210> SEQ ID NO 62
<211> LENGTH: 118
<212> TYPE: PRT
<213> ORGANISM: Artificial Sequence
<220> FEATURE:
<223> OTHER INFORMATION: Variable Heavy Sequence Version 1 from Antibody
      19B10-Hum

<400> SEQUENCE: 62

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Thr Asp Tyr
            20                  25                  30

Tyr Val His Trp Val Lys Gln Arg Pro Gly Gln Gly Leu Glu Trp Met
        35                  40                  45

Gly Arg Ile Asp Pro Glu Asp Gly Asp Thr Lys Phe Ala Pro Lys Phe
    50                  55                  60

Gln Gly Lys Ala Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Gly Tyr Trp Gly Gln Gly Thr
            100                 105                 110

Leu Val Thr Val Ser Ser
        115

<210> SEQ ID NO 63
<211> LENGTH: 118
<212> TYPE: PRT
<213> ORGANISM: Artificial Sequence
<220> FEATURE:
<223> OTHER INFORMATION: Variable Heavy Sequence Version 2 from Antibody
      19B10-Hum

<400> SEQUENCE: 63

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Thr Asp Tyr
            20                  25                  30

Tyr Val His Trp Val Lys Gln Arg Pro Gly Gln Gly Leu Glu Trp Met
            35                  40                  45

Gly Arg Ile Asp Pro Glu Asp Gly Asp Thr Lys Phe Ala Pro Lys Phe
 50                  55                  60

Gln Gly Lys Val Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Gly Tyr Trp Gly Gln Gly Thr
            100                 105                 110

Leu Val Thr Val Ser Ser
        115

<210> SEQ ID NO 64
<211> LENGTH: 118
<212> TYPE: PRT
<213> ORGANISM: Artificial Sequence
<220> FEATURE:
<223> OTHER INFORMATION: Variable Heavy Sequence Version 3 from Antibody
      19B10-Hum

<400> SEQUENCE: 64

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Tyr
            20                  25                  30

Tyr Val His Trp Val Lys Gln Ala Pro Gly Gln Gly Leu Glu Trp Ile
            35                  40                  45

Gly Arg Ile Asp Pro Glu Asp Gly Asp Thr Lys Phe Ala Pro Lys Phe
 50                  55                  60

Gln Gly Lys Ala Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Gly Tyr Trp Gly Gln Gly Thr
            100                 105                 110

Leu Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: Variable Heavy Sequence Version 4 from Antibody
      19B10-Hum

<400> SEQUENCE: 65

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Tyr
            20                  25                  30

Tyr Val His Trp Val Lys Gln Ala Pro Gly Gln Gly Leu Glu Trp Met
            35                  40                  45

Gly Arg Ile Asp Pro Glu Asp Gly Asp Thr Lys Phe Ala Pro Lys Phe
 50                  55                  60

Gln Gly Lys Ala Thr Met Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Leu Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: Variable Heavy Sequence Version 5 from Antibody
      19B10-Hum

<400> SEQUENCE: 66

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Thr Asp Tyr
                20                  25                  30

Tyr Val His Trp Val Lys Gln Ala Pro Gly Gln Gly Leu Glu Trp Met
            35                  40                  45

Gly Arg Ile Asp Pro Glu Asp Gly Asp Thr Lys Phe Ala Pro Lys Phe
        50                  55                  60

Gln Gly Lys Ala Thr Met Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Leu Val Thr Val Ser Ser
        115

<210> SEQ ID NO 67
<211> LENGTH: 118
<212> TYPE: PRT
<213> ORGANISM: Artificial Sequence
<220> FEATURE:
<223> OTHER INFORMATION: Variable Heavy Sequence Version 1 from Antibody
      10F2Hum

<400> SEQUENCE: 67

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
                20                  25                  30

Tyr Ile His Trp Val Lys Gln Arg Pro Gly Lys Gly Leu Glu Trp Met
            35                  40                  45

Gly Arg Ile Asp Pro Glu Asp Gly Asp Thr Lys Tyr Asp Pro Lys Phe
        50                  55                  60

Gln Gly Arg Val Thr Met Thr Ala Asp Thr Ser Thr Ala Thr Ala Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Thr Val Thr Val Ser Ser
        115

<210> SEQ ID NO 68
<211> LENGTH: 118
<212> TYPE: PRT
<213> ORGANISM: Artificial Sequence
<220> FEATURE:
<223> OTHER INFORMATION: Variable Heavy Sequence Version 2 from Antibody
      10F2Hum

<400> SEQUENCE: 68

Glu Val Gln Leu Val Gln Ser Gly Ala Glu Val Lys Lys Pro Gly Ala
1               5                   10                  15

Thr Val Lys Ile Ser Cys Thr Val Ser Gly Phe Asn Ile Lys Asp Tyr
            20                  25                  30

Tyr Ile His Trp Val Lys Gln Arg Pro Gly Lys Gly Leu Glu Trp Met
        35                  40                  45

Gly Arg Ile Asp Pro Glu Asp Gly Asp Thr Lys Tyr Asp Pro Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Thr Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: Variable Heavy Sequence Version 3 from Antibody
      10F2Hum

<400> SEQUENCE: 69

Glu Val Gln Leu Val Gln Ser Gly Ala Glu Val Lys Lys Pro Gly Ala
1               5                   10                  15

Thr Val Lys Ile Ser Cys Thr Val Ser Gly Phe Asn Ile Lys Asp Tyr
            20                  25                  30

Tyr Ile His Trp Val Lys Gln Arg Pro Gly Lys Gly Leu Glu Trp Met
        35                  40                  45

Gly Arg Ile Asp Pro Glu Asp Gly Asp Thr Lys Tyr Asp Pro Lys Phe
    50                  55                  60

Gln Gly Lys Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Thr Val Thr Val Ser Ser
        115

<210> SEQ ID NO 70
<211> LENGTH: 118
<212> TYPE: PRT
<213> ORGANISM: Artificial Sequence

```
<220> FEATURE:
<223> OTHER INFORMATION: Variable Heavy Sequence Version 4 from Antibody
      10F2Hum

<400> SEQUENCE: 70

Glu Val Gln Leu Val Gln Ser Gly Ala Glu Val Lys Lys Pro Gly Ala
1               5                   10                  15

Thr Val Lys Ile Ser Cys Thr Val Ser Gly Phe Asn Ile Lys Asp Tyr
            20                  25                  30

Tyr Ile His Trp Val Lys Gln Ala Pro Gly Lys Gly Leu Glu Trp Met
        35                  40                  45

Gly Arg Ile Asp Pro Glu Asp Gly Asp Thr Lys Tyr Asp Pro Lys Phe
50                  55                  60

Gln Gly Lys Ala Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Thr Val Thr Val Ser Ser
            115

<210> SEQ ID NO 71
<211> LENGTH: 118
<212> TYPE: PRT
<213> ORGANISM: Artificial Sequence
<220> FEATURE:
<223> OTHER INFORMATION: Variable Heavy Sequence Version 5 from Antibody
      10F2Hum

<400> SEQUENCE: 71

Glu Val Gln Leu Val Gln Ser Gly Ala Glu Val Lys Lys Pro Gly Ala
1               5                   10                  15

Thr Val Lys Ile Ser Cys Thr Val Ser Gly Phe Asn Ile Lys Asp Tyr
            20                  25                  30

Tyr Ile His Trp Val Lys Gln Arg Pro Gly Lys Gly Leu Glu Trp Met
        35                  40                  45

Gly Arg Ile Asp Pro Glu Asp Gly Asp Thr Lys Tyr Asp Pro Lys Phe
50                  55                  60

Gln Gly Lys Ala Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Ser Tyr Tyr Val Gly Thr Tyr Gly Tyr Trp Gly Gln Gly Thr
            100                 105                 110

Thr Val Thr Val Ser Ser
            115

<210> SEQ ID NO 72
<211> LENGTH: 118
<212> TYPE: PRT
<213> ORGANISM: Artificial Sequence
<220> FEATURE:
<223> OTHER INFORMATION: Variable Heavy Sequence Version 6 from Antibody
      10F2Hum

<400> SEQUENCE: 72

Glu Val Gln Leu Val Gln Ser Gly Ala Glu Val Lys Lys Pro Gly Ala
1               5                   10                  15
```

```
Thr Val Lys Ile Ser Cys Thr Val Ser Gly Phe Asn Ile Lys Asp Tyr
            20                  25                  30

Tyr Ile His Trp Val Lys Gln Ala Pro Gly Lys Gly Leu Glu Trp Ile
            35                  40                  45

Gly Arg Ile Asp Pro Glu Asp Gly Asp Thr Lys Tyr Asp Pro Lys Phe
 50                  55                  60

Gln Gly Lys Ala Thr Met Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Thr Ser Tyr Tyr Val Gly Thr Tyr Gly Tyr Trp Gly Gln Gly Thr
                100                 105                 110

Thr Val Thr Val Ser Ser
        115

<210> SEQ ID NO 73
<211> LENGTH: 118
<212> TYPE: PRT
<213> ORGANISM: Artificial Sequence
<220> FEATURE:
<223> OTHER INFORMATION: Variable Heavy Sequence Version 7 from Antibody
      10F2Hum

<400> SEQUENCE: 73

Glu Val Gln Leu Val Gln Ser Gly Ala Glu Val Lys Lys Pro Gly Ala
 1               5                  10                  15

Thr Val Lys Ile Ser Cys Lys Val Ser Gly Phe Asn Ile Lys Asp Tyr
            20                  25                  30

Tyr Ile His Trp Val Gln Gln Ala Pro Gly Lys Gly Leu Glu Trp Met
            35                  40                  45

Gly Arg Ile Asp Pro Glu Asp Gly Asp Thr Lys Tyr Asp Pro Lys Phe
 50                  55                  60

Gln Gly Arg Val Thr Met Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Thr Ser Tyr Tyr Val Gly Thr Tyr Gly Tyr Trp Gly Gln Gly Thr
                100                 105                 110

Thr Val Thr Val Ser Ser
        115

<210> SEQ ID NO 74
<211> LENGTH: 106
<212> TYPE: PRT
<213> ORGANISM: Artificial Sequence
<220> FEATURE:
<223> OTHER INFORMATION: Variable Light Sequence Version 1 from Antibody
      10F2Hum

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys Ser Ala Thr Ser Ser Val Ser Tyr Ile
            20                  25                  30

Leu Trp Phe Gln Gln Lys Pro Gly Lys Ala Pro Lys Leu Leu Ile Tyr
            35                  40                  45

Ser Thr Ser Asn Leu Ala Ser Gly Val Pro Ser Arg Phe Ser Gly Ser
 50                  55                  60
```

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Thr Phe Tyr Pro Tyr Thr
                85                  90                  95

Phe Gly Gly Gly Thr Lys Val Glu Ile Lys
            100                 105

<210> SEQ ID NO 75
<211> LENGTH: 106
<212> TYPE: PRT
<213> ORGANISM: Artificial Sequence
<220> FEATURE:
<223> OTHER INFORMATION: Variable Light Sequence Version 2 from Antibody
      10F2Hum

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Ile
                20                  25                  30

Leu Trp Phe Gln Gln Lys Pro Gly Lys Ala Pro Lys Leu Leu Ile Tyr
            35                  40                  45

Ser Thr Ser Asn Leu Ala Ser Gly Val Pro Ala Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Thr Phe Tyr Pro Tyr Thr
                85                  90                  95

Phe Gly Gly Gly Thr Lys Val Glu Ile Lys
            100                 105

<210> SEQ ID NO 76
<211> LENGTH: 106
<212> TYPE: PRT
<213> ORGANISM: Artificial Sequence
<220> FEATURE:
<223> OTHER INFORMATION: Variable Light Sequence Version 3 from Antibody
      10F2Hum

<400> SEQUENCE: 76

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Ile
                20                  25                  30

Leu Trp Phe Gln Gln Lys Pro Gly Lys Ala Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Thr Phe Tyr Pro Tyr Thr
                85                  90                  95

Phe Gly Gly Gly Thr Lys Val Glu Ile Lys
            100                 105

<210> SEQ ID NO 77
<211> LENGTH: 11
<212> TYPE: PRT
<213> ORGANISM: Artificial Sequence
<220> FEATURE:

```
<223> OTHER INFORMATION: Heavy Chain CDR3 for 2H11, 10F2 and 19B10

<400> SEQUENCE: 77

Thr Thr Ser Tyr Tyr Val Gly Thr Tyr Gly Tyr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Heavy Chain CDR3 for 20E2

<400> SEQUENCE: 78

Ala Arg Gln Asp Gly Tyr Arg Tyr Ala Met Asp Tyr
1               5                   10
```